United States Patent
Michiwaki et al.

(10) Patent No.: US 10,049,602 B2
(45) Date of Patent: Aug. 14, 2018

(54) SWALLOWING SIMULATION APPARATUS AND METHOD

(71) Applicants: Meiji Co., Ltd., Koto-ku, Tokyo (JP); Yukihiro Michiwaki, Chuo-ku, Tokyo (JP)

(72) Inventors: Yukihiro Michiwaki, Tokyo (JP); Keigo Hanyuu, Odawara (JP); Tetsu Kamiya, Odawara (JP); Yoshio Toyama, Odawara (JP); Rika Murakami, Odawara (JP)

(73) Assignee: MEIJI CO., LTD, Tokyo (JP)

(*) Notice: Subject to any disclaimer, the term of this patent is extended or adjusted under 35 U.S.C. 154(b) by 755 days.

(21) Appl. No.: 14/387,531

(22) PCT Filed: Mar. 18, 2013

(86) PCT No.: PCT/JP2013/057718
§ 371 (c)(1),
(2) Date: Sep. 23, 2014

(87) PCT Pub. No.: WO2013/146436
PCT Pub. Date: Oct. 3, 2013

(65) Prior Publication Data
US 2015/0079570 A1    Mar. 19, 2015

(30) Foreign Application Priority Data

Mar. 27, 2012 (JP) ................... 2012-072178

(51) Int. Cl.
*G09B 23/32* (2006.01)
*G09B 23/28* (2006.01)
(Continued)

(52) U.S. Cl.
CPC ............ *G09B 23/32* (2013.01); *G09B 23/28* (2013.01); *G09B 23/30* (2013.01); *A61B 5/4205* (2013.01);
(Continued)

(58) Field of Classification Search
CPC ..... A61C 19/045; A61C 11/00; A61B 5/4205; G06F 19/3437; G06T 17/00; G09B 23/30; G09B 23/32
(Continued)

(56) References Cited

U.S. PATENT DOCUMENTS 6,192,329 B1 * 2/2001 Rider ..................... B44C 3/042
703/6
2002/0150859 A1 * 10/2002 Imgrund ................. A61C 7/00
433/24
(Continued)

FOREIGN PATENT DOCUMENTS

CN    103596498 A    2/2014
CN    103597510 A    2/2014

OTHER PUBLICATIONS

Lloyd et al., "ArtiSynth: A Fast Interactive Biomechanical Modeling Toolkit Combining Multibody and Finite Element Simulation", Mar. 12, 2012, Stud Mechanobiol Tissue Eng Biomater (2012) 11: 355-394.*
(Continued)

*Primary Examiner* — Jack Yip
(74) *Attorney, Agent, or Firm* — Squire Patton Boggs (US) LLP

(57) ABSTRACT

A swallowing simulation apparatus that facilitate approximately reproducing an actual phenomenon of swallowing and allows quantifying a physical quantity related to a behavior and a physical property of an orally-ingested
(Continued)

CONVENTIONAL CALCULATIONAL METHOD (LATTICE METHOD)    NEW CALCULATIONAL METHOD (PARTICLE METHOD)

product is provided. The swallowing simulation apparatus 100A comprises a head-and-neck modeling unit 10 configured to form a dynamic three-dimensional model of the head-and-neck 10a that includes head-and-neck organs, an organ movement setting unit 30 configured to set movements of the respective head-and-neck organs in the dynamic three-dimensional model of the head-and-neck, an orally-ingested-product physical-property setting unit 40 configured to set an orally-ingested product as an analysis target and a physical property of the orally-ingested product, an input unit 81 configured to input a pseudo-orally-ingested product 20 formed by modeling the orally-ingested product to an oral cavity, a movement analysis unit 50 configured to analyze the movements of the respective head-and-neck organs in the dynamic three-dimensional model of the head-and-neck 10a and a behavior of the pseudo-orally-ingested product 20 during swallowed in a three-dimensional space using a particle method, and a display unit 82 configured to display an analysis result of the movements of the respective head-and-neck organs and the behavior of the pseudo-orally-ingested product during swallowed that are analyzed by the movement analysis unit 50 on a movement screen.

21 Claims, 30 Drawing Sheets

(51) Int. Cl.
*G09B 23/30* (2006.01)
*G06T 17/00* (2006.01)
*A61C 19/045* (2006.01)
*A61C 11/00* (2006.01)
*A61B 5/00* (2006.01)

(52) U.S. Cl.
CPC ............ *A61C 11/00* (2013.01); *A61C 19/045* (2013.01); *G06T 17/00* (2013.01)

(58) Field of Classification Search
USPC .......................................... 434/270
See application file for complete search history.

(56) References Cited

U.S. PATENT DOCUMENTS

| | | | |
|---|---|---|---|
| 2010/0015589 A1* | 1/2010 | Lehavi ................. | G09B 23/283 434/263 |
| 2011/0276159 A1* | 11/2011 | Chun ..................... | A61C 11/00 700/98 |
| 2012/0015316 A1* | 1/2012 | Sachdeva ................ | G06T 17/00 433/24 |
| 2013/0066598 A1* | 3/2013 | Fisker .................... | A61C 11/00 703/1 |
| 2014/0120224 A1 | 5/2014 | Kamiya | |
| 2014/0120509 A1 | 5/2014 | Kamiya et al. | |

OTHER PUBLICATIONS

Mizunuma et al., "Numerical Modeling and Simulation on the Swallowing of Jelly", J. of Texture Studies, 2009, vol. 40, No. 4, pp. 406-426.*
Supplementary European Search Report for application EP 13767280.4, dated Sep. 28, 2015, 8 pgs.
Mizunuma et al., "Numerical Modeling and Simulation on the Swallowing of Jelly", Journal of Texture Studies vol. 40, No. 4, pp. 406-426, Aug. 1, 2009.
Kamizu, et al., The Society of Chemical Engineers 41st Autumn Meeting Presentation Abstracts, 2009, P09, p. 43.
Mizunuma et al., The Japan Society of Mechanical Engineers Annual Conference Proceedings, 2005 pp. 83-84.
Hiroshi Mizunuma et al., "Ekijo Shokkai no Enge no Simulation", Dai 34 Kai Japanese Society of Biorheology Nenkai Program Shorokushu, Jun. 3, 2011, pg. 99.
Shun'ichi Ishida et al.,"Numerical simulation of swallowing based on videofluorography", Dai 23 Kai Bioengineering Koen Ronbunshu, Jan. 7, 2011, No. 10-74, pp. 559-560.
International Search Report for PCT/JP2013/057718, dated Apr. 16, 2013, 1 pg.

* cited by examiner

CONVENTIONAL CALCULATIONAL METHOD (LATTICE METHOD)

NEW CALCULATIONAL METHOD (PARTICLE METHOD)

Time:0.080000

Time:0.600100

Time:0.000000

Time:0.200100

Time:0.400100

Time:0.500100

Time:0.600100

Time:0.700100

Time:0.800000

Time:0.900100

Time:1.000100

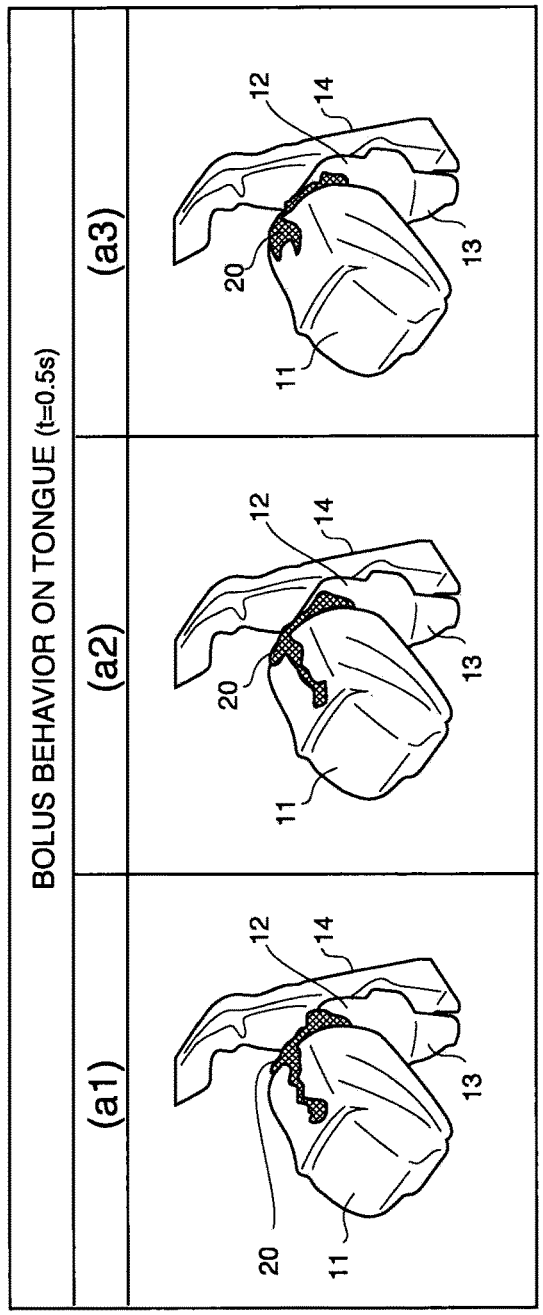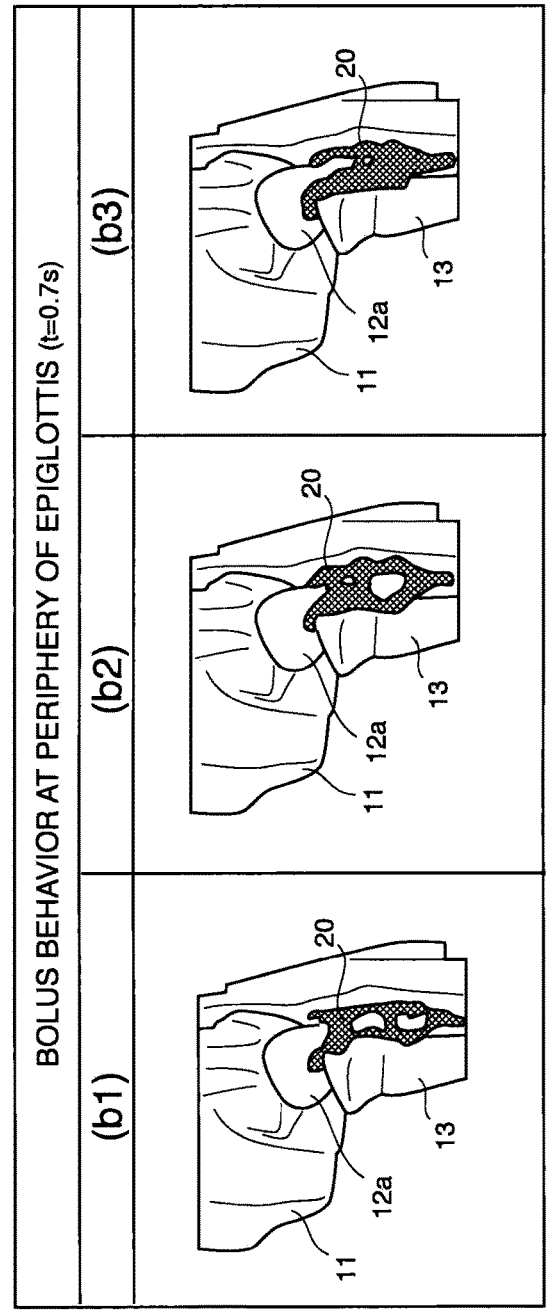
FIG. 13A
FIG. 13B (AREA A) AREA ON TONGUE IN ORAL CAVITY ($0.035 \leq Y \leq 0.050$)
($0.000 \leq Z \leq 0.020$)

(AREA B) AREA OF ESOPHAGEAL ENTRANCE IN PHARYNX SPACE ($-0.04 \leq Y \leq 0.000$)
($-0.04 \leq Z \leq -0.020$)

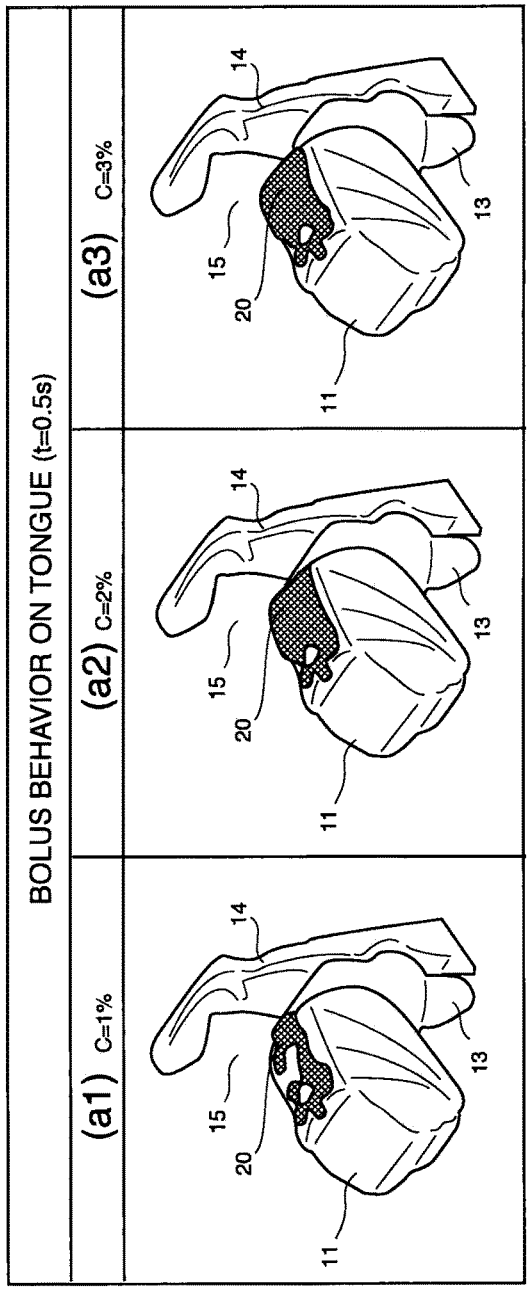
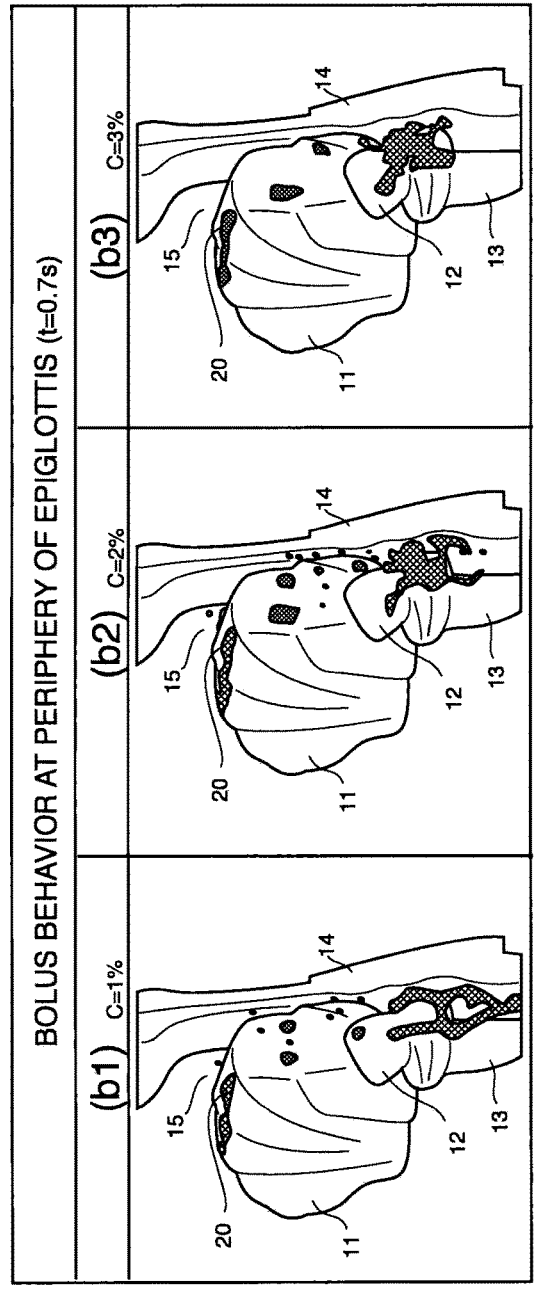
FIG. 21A
FIG. 21B

SWALLOWING SIMULATION APPARATUS AND METHOD

BACKGROUND OF THE INVENTION

Field of the Invention

The present invention relates to a swallowing simulation apparatus and method. More specifically, the present invention relates to a swallowing simulation apparatus, a dynamic three-dimensional model of a head-and-neck, a swallowing simulation method, a program readable by a computer, an orally-ingested-product development assistance apparatus, an orally-ingested-product development method, an orally-ingested-product production method, a dietary education assistance apparatus, a dietary education method and a diagnosis assistance apparatus that analyze behaviors of a fluid and a bolus passing through an oral cavity or a throat using a particle method.

Description of Related Art

The swallowing action, in particular, the relationship between the physical property of the food product and the movements of the head-and-neck organ during swallowed, is complicated. Therefore, it is extremely difficult to grasp the phenomenon itself accurately. However, in the fields of medical treatment and nursing, to prevent accidental swallowing and accidental ingestion by an old person or a handicapped person, reductions in risks of accidental swallowing and accidental ingestion have been strived through repetition of various trials and errors. Given that recently there have been accident of incidents of choking on konjac jelly, in general food products, it is required to assure safety of a food/drink product using an objective value or index.

Two methods are available for solution of the swallowing phenomenon: a method that directly obtains biological information such as a videofluoroscopic swallowing and a myoelectric potential measurement and a method that indirectly obtains information using, for example, a swallowing robot and a numerical value simulation. These methods have a lot of problems such as a heavy burden imposed on the examinee and occurrence of extensive change of the behavior or the structure for the head-and-neck organ of the robot.

Up to the present, numerical analyses on a behavior of a bolus, such as a fluid and/or a solid material in a living body, have been performed. For the fluid, an inside of an analysis target region is separated by a grid referred to as a mesh. Calculations have been performed using a lattice method that analyzes physical quantities (speed, temperature, pressure) at the grid point and the inside of the grid (see Non-Patent Literature 1). In the case of treating the bolus as a semisolid, calculations have been performed using a structural analysis method for machine components such as a finite element method (see Non-Patent Literature 2).

Non Patent Literature 1: Kamizu, et al., The Society of Chemical Engineers 41st Autumn Meeting Presentation Abstracts, 2009, P09

Non Patent Literature 2: Mizunuma, et al., The Japan Society of Mechanical Engineers Annual Conference Proceedings, 2005(2), 83-84

However, with the lattice method, which is a mainstream of the conventional numerical analysis, phenomena such as a large deformation of a surface and a spray seen at the fluid and the bolus while actually being swallowed is difficult to be caught. Accordingly, reproduction of the actual phenomenon has been difficult.

Firstly, an object of the present invention is to provide a swallowing simulation apparatus, a dynamic three-dimensional model of a head-and-neck, a swallowing simulation method, a program readable by the computer, an orally-ingested-product development assistance apparatus, an orally-ingested-product development method, an orally-ingested-product production method, a dietary education assistance apparatus, a dietary education method, and a diagnosis assistance apparatus that facilitate approximately reproducing an actual phenomenon of swallowing, that is, behaviors of a head-and-neck organ and an orally-ingested product including a food/drink product, a medicinal product, and a nonmedicinal product.

The inventors of this application proposed a swallowing simulation apparatus and a swallowing simulation method (in Japanese patent applications No. 2011-146780 and No. 2011-146781 that are both unpublished) that set a movement of an oral cavity organ and a physical property of a food/drink product or the like to two-dimensionally analyze behaviors of the oral cavity organ and the food/drink product using a particle method. These apparatus and method have allowed approximately reproducing an actual phenomenon of swallowing and have allowed visualizing a swallowing phenomenon, compared with the conventional technique. However, there has been a further request for three-dimensionally and accurately expressing the behaviors of an oral cavity organ and a food/drink product during swallowed compared with a simulation in a two-dimensional space. Additionally, the limitation on the program to be used causes a problem that it is difficult to quantify the physical quantity related to the behavior and the physical property of the orally-ingested product.

Secondly, an object of the present invention is to provide a swallowing simulation apparatus, a dynamic three-dimensional model of a head-and-neck, a swallowing simulation method, a program readable by a computer, an orally-ingested-product development assistance apparatus, an orally-ingested-product development method, an orally-ingested-product production method, a dietary education assistance apparatus, a dietary education method, and a diagnosis assistance apparatus that allows accurately expressing behaviors of a head-and-neck organ and a food/drink product during swallowed and that allows quantifying a physical quantity related to a behavior and a physical property of an orally-ingested product including a food/drink product, a medicinal product, and a nonmedicinal product.

BRIEF SUMMARY OF THE INVENTION

To solve the above-described problem, a swallowing simulation apparatus 100A according to a first aspect of the present invention, for example, as illustrated in FIG. 2 (see FIGS. 3A to 3D for specific organs as needed), comprises a head-and-neck modeling unit 10 configured to form a dynamic three-dimensional model of a head-and-neck 10a that includes head-and-neck organs, an organ movement setting unit 30 configured to set a movement of each of the head-and-neck organs in the dynamic three-dimensional model of the head-and-neck 10a, an orally-ingested-product physical-property setting unit 40 configured to set an orally-ingested product including a food/drink product, a medicinal product, and a nonmedicinal product as an analysis target and a physical property of the orally-ingested product, an input unit 81 configured to input a pseudo-orally-ingested product 20 formed by modeling the orally-ingested product including a food/drink product, a medicinal product, and a nonmedicinal product to an oral cavity, a movement analysis unit 50 configured to analyze the movement of each of the head-and-neck organs in the dynamic three-dimensional model of the head-and-neck 10a and a behavior of the pseudo-orally-ingested product 20 during swallowed, in a three-dimensional space using a particle method, and a display unit 82 configured to display an analysis result of the movement of each of the head-and-neck organs and the behavior of the pseudo-orally-ingested product during swallowed that are analyzed by the movement analysis unit 50, on a movement screen.

Here, "dynamic three-dimensional" of the model of a head-and-neck means a change with time in a three-dimensional space. The three-dimensional space may be formed as a virtual three-dimensional space in a computer. Head-and-neck organs include a tongue 11, a larynx 12, an epiglottis 12a, a trachea 13, a pharynx 14, a palate 15 (formed of a hard palate 15a and a soft palate 15b), a jaw 16, a gullet 18, and the like (see FIGS. 3A to 3D). Respective organs related to an oral cavity 17, the pharynx 14, and a larynx portion 12c (formed of the epiglottis 12a and the larynx 12) are also included. The dynamic three-dimensional model of the head-and-neck 10a includes the above-described respective head-and-neck organs. It is only necessary to include the entrance portions for the gullet 18 and the trachea 13. The dynamic three-dimensional model of the head-and-neck 10a is preferred to be formed in accordance with the actual movement of the oral cavity organs. However, when the number of particles is increased, the load on a computer PC that performs analysis in the three-dimensional space is increased. Accordingly, the movable portions may be limited to simplify and facilitate the analysis. For each head-and-neck organ, a polygon (that is a wall boundary made by a polygon distance function, and that is a boundary in which a wall that is not moved by receiving an external force from fluid or the like is arranged in the space as the distance function) may be defined so as to eliminate calculation of the head-and-neck organ as particles. For more detailed examination, it is possible to define each head-and-neck organ as particles (a rigid substance, an elastic body, a plastic body, or an elasto-plastic body) for calculation (see Koshizuka Seiichi, Computational Mechanics Lecture Series 5, Particle Method, Edited by Japan Society for Computational Engineering and Science, pp. 51-68).

Since the dynamic three-dimensional model of the head-and-neck 10a is formed in the virtual space, if there is no problem with the analysis, a possible structure is that each of the head-and-neck organs overlaps with one another in the three-dimensional space. The movements for each head-and-neck organ include moving, rotating, a periodic movement, and the like. The orally-ingested product may be any of a liquid, a semisolid (with plasticity but without fluidity), or a solid. Physical properties of the orally-ingested product include a density, a viscosity, a surface tension, a contact angle, a heat capacity, a thermal conductivity, a dynamic friction coefficient, and the like. However, it is not necessary to set all of these physical properties, and it is only necessary to set any of the physical properties. The behavior of the pseudo-orally-ingested product 20 during swallowed typically means a behavior of movement from the oral cavity through the pharynx 14 to the gullet 18. The case of returning to the oral cavity 17 without reaching the pharynx 14 or the gullet 18 or the case of entering the larynx 12 or the nasal cavity is also possible. The physical quantities related to the behavior of the pseudo-orally-ingested product 20 during swallowed include a period of time, a position coordinate, a speed, a pressure, a temperature, a shear rate, a normal stress, a shear stress, and the like. However, it is not necessary to use all of these physical quantities for analysis, and it is only necessary to use any of the physical quantities for analysis. Although it is preferred to quantify these physical properties and physical quantities, relative values may be used.

The input unit 81 includes, for example, a computer mouse and a keyboard. A cursor is dragged and dropped into the oral cavity of the dynamic three-dimensional model of the head-and-neck 10a using a computer mouse to input the pseudo-orally-ingested product (including the pseudo-food/drink product, the pseudo-medicinal product or the pseudo-nonmedicinal product) 20. By dragging and dropping with the computer mouse, the position of the pseudo-orally-ingested product 20 to be injected is specified. An orally-ingested-product input setting unit 45 (see FIG. 24) may be disposed to preliminarily set a pseudo-orally-ingested product and an injection position and injection timing of the pseudo-orally-ingested product so as to automatically inject the pseudo-orally-ingested product 20. The movement analysis unit 50 performs analysis using the particle method, and can employ, for example, a moving particle-semi-implicit (MPS) method. For "display on a movement screen" of the display unit 82, a display on the movement screen such as a liquid crystal display is typically used.

Here, the case where the simulation is performed by a doctor or a dentist in a checkup or a medical practice to evaluate the analysis result is referred to as diagnosis that is distinguished from evaluation made by an ordinary person. That is, in this description, the evaluation does not include diagnosis. Displaying the movement screen is useful for an evaluator or a person to diagnose to observe the movement screen for evaluation or diagnosis. However, for automatic evaluation or diagnosis, a pseudo-screen display unit 82A (see FIG. 24) is disposed in a computer and an evaluation/diagnosis condition storage unit 83A (see FIG. 24) is disposed in a storage unit 83. Analysis results are dynamically displayed on a virtual movement screen of the pseudo-screen display unit 82A. Then, the analysis results are collated with the evaluation condition or the diagnosis condition of the evaluation/diagnosis condition storage unit 83A, and evaluated or diagnosed in an evaluation/diagnosis unit 60 (see FIG. 24) in the computer. Here, the "display on a movement screen" also includes the case where the analysis results are thus dynamically displayed on the virtual movement screen of the pseudo-screen display unit 82A. The pseudo-screen display unit 82A is included in both the personal computer PC and the display unit 82. In the display of the dynamic three-dimensional model of the head-and-neck 10a, each of the head-and-neck organs is preferred to be displayed to be translucent in mutually different colors because the motion of each of the head-and-neck organs becomes easy to see.

With the configuration of this aspect, for the dynamic three-dimensional model of the head-and-neck 10a, the movements of the head-and-neck organs and the physical properties of the orally-ingested product are set to analyze the behavior of the orally-ingested product using the particle method. This allows providing the swallowing simulation apparatus that facilitates approximately reproducing the actual phenomenon of swallowing. Additionally, quantitatively setting the physical properties of the orally-ingested product and the physical quantities related to the behavior of the orally-ingested product to numerical values with dimensions for analysis allows providing the swallowing simulation apparatus that can accurately express the behaviors of the head-and-neck organs and the orally-ingested product during swallowed and that can hourly quantify the physical quantities related to the behavior during swallowed.

According to the swallowing simulation apparatus 100A of a second aspect of the present invention, in the first aspect, the head-and-neck modeling unit 10 is configured to set the head-and-neck organ as a polygon or particles (a rigid substance, powder, an elastic body, a plastic body, or an elasto-plastic body), and the movement analysis unit 50 is configured to treat the pseudo-orally-ingested product 20 as particles.

Here, the dynamic three-dimensional model of the head-and-neck 10a is preferred to be formed in accordance with the actual movements of the oral cavity, the pharynx, the larynx, and the gullet and to be temporally deformed for performing accurate analysis. Therefore, the entire model is preferred to be treated as particles. However, when the number of particles is increased, the load on the computer PC that performs analysis in the three-dimensional space is increased. Accordingly, it is efficient to perform analysis while the head-and-neck organ is set as a polygon so as to simplify and facilitate the analysis.

With the configuration of this aspect, when the three-dimensional analysis is performed, the head-and-neck organ is set as a polygon or particles (a rigid substance, an elastic body, a plastic body, and an elasto-plastic body) and the pseudo-orally-ingested product 20 is treated as particles (a fluid, a rigid substance, an elastic body, a plastic body, and an elasto-plastic body). Accordingly, setting the head-and-neck organ and the pseudo-orally-ingested product 20 optionally allows various analyses depending on a purpose and a condition.

According to the swallowing simulation apparatus 100A of a third aspect of the present invention, for example, as illustrated in FIGS. 4A and 4B (see FIG. 2 for configuration), in the second aspect, the head-and-neck modeling unit 10 is configured to set a model of a tongue 11 as one of head-and-neck organs to have a structure divided into n pieces of sector portions 11a to 11e in a near-far direction, wherein n is an integer equal to or more than 2, while a mental region 16a of a mandible as an origin of a genio-glossus 11f is set to a pivot of sector, and the organ movement setting unit 30 is configured to set movements of organs such that each of the sector portions 11a to 11e is configured to vibrate in cooperation with one another while vibrations of different sector portions have predetermined phase differences in a radial direction so as to perform a traveling wave movement by movements of organs to transport the pseudo-orally-ingested product 20 toward a far-side direction.

Here, as the division number n of the tongue 11, a number equal to or more than 3 allows expressing a smooth traveling wave movement while a number exceeding 7 increases a computational load. Thus, the number is preferred to be from 4 to 6. This allows approximately reproducing a traveling wave action of the tongue during swallowing.

With the configuration of this aspect, the tongue is divided into n pieces of sector portions in the near-far direction and the above-described cooperative vibration is generated. This allows approximately reproducing the behavior of the tongue during swallowing, thus ensuring efficient analysis similar to the actual phenomenon. Here, the shape of the tongue 11 may be formed as particles in association with the actual movement and a temporally deformed shape may be read for each calculation.

According to the swallowing simulation apparatus 100A of a forth aspect of the present invention, for example, as illustrated in FIGS. 6A to 6C and FIGS. 7A to 7B, in the third aspect, the head-and-neck modeling unit 10 is configured to form the model of the tongue 10b having a structure where dome shape portions of each of the sector portions 11a to 11e overlaps with a dome shape portion of another such that gap is not formed between the sector portions 11a to 11e when each of the sector portions vibrates, and the dome shape portion is for forming a surface of the tongue, further the head-and-neck modeling unit 10 is configured to form the model of the tongue having the structure where a tongue surface portion 19 that has both right and left sides extending in the radial direction and each of the sector portions and each of the dome shape portions has a depression in a central portion between the right and left sides is overlapped with each of the sector portions 11a to 11e and each of the sector portions 11a to 11e vibrates in radial direction in the depression of the tongue surface portion 19 in a static condition; and the organ movement setting unit 30 is configured to set a movements of organs such that each of the sector portions 11a to 11e rotates by a predetermined angle toward a far side in a circumferential direction during swallowing and then the pseudo-orally-ingested product 20 is pushed toward a far side by the sector portion 11e at a farthest side of the tongue 11 at an end of swallowing.

Here, the predetermined angle is preferred to be 15°. This, however, should not be construed in a limiting sense. The predetermined angle may be 10 to 20°. The overlap portion is preferred to have 5 mm. This, however, should not be construed in a limiting sense. The overlap portion may have 3 to 7 mm. With the configuration of this aspect, the flow passage of the orally-ingested product 20 is formed in the depression without forming gaps between the respective sector portions 11a to 11e. Then, the orally-ingested product 20 is smoothly transported to the far side of the oral cavity. This allows further approximately reproducing the behavior of the tongue 11 during swallowing.

According to the swallowing simulation apparatus 100A of a fifth aspect of the present invention, for example, as illustrated in FIGS. 9A to 9C and FIGS. 10A to 10B, in the third or the forth aspect, the head-and-neck modeling unit 10 is configured to set the model of the dynamic three-dimensional head-and-neck 10a having a structure where the head-and-neck includes a tongue 11, a palate 15, a pharynx 14, a larynx portion 12c, a trachea 13 and a gullet 18, the larynx portion 12c is divided into an epiglottis 12a and a larynx 12, an esophageal entrance 18a of the gullet 18 is configured to be closed before swallowing is started, and the esophageal entrance 18 is configured to extend and the pharynx 14 is configured to contract during swallowing; and the organ movement setting unit 30 is configured to set movements of organs such that the larynx 12 is configured to be moved in a direction to the mental region 16a of the mandible 16 to open the esophageal entrance 18a, the pharynx 14 is configured to contract, and then the epiglottis 12a is configured to be rotated by a predetermined angle toward the far side during swallowing so as to close an entrance of the larynx 12.

Here, the rotation by the predetermined angle is most preferred to employ 135 degrees that is similar to the actual phenomenon. An angle (for example, within ±15 degrees) at the proximity of this angle is also preferred. Additionally, "the pharynx is configured to contract" specifically means that the pharynx is shortened in the upper direction and the lumen of the pharynx contracts, or includes this content. This configuration allows approximately reproducing the behavior of the larynx portion 12c during swallowing and opening and closing of the gullet 18. Here, the motions of these organs can be achieved by giving numerical values from the organ movement setting unit 30 for forcible movement, or also by movement interlocking with the motion of the muscle in association with these organs. Furthermore, models of the respective organs changing with time may be read for each analysis so as to provide a smoother movement.

According to the swallowing simulation apparatus 100A of a sixth aspect of the present invention, for example, as illustrated in FIGS. 22A1 to 22B3 (see FIG. 2 for configuration), in any one of the first aspect to the fifth aspect, the orally-ingested-product physical-property setting unit 40 is configured to set a plurality of pseudo-orally-ingested products 20 of liquid, semisolid, or solid as the analysis target, where the pseudo-orally-ingested products 20 have different physical properties; and the movement analysis unit 50 is configured to determine free surfaces of the plurality of pseudo-orally-ingested products 20 and boundaries between the plurality of pseudo-orally-ingested products 20 so as to analyze an interlocking behavior of the plurality of pseudo-orally-ingested products 20.

This configuration allows reproducing the interlocking behavior of the orally-ingested product similar to the actual phenomenon regarding the plurality of pseudo-orally-ingested products 20, and is effective for analyzing the interlocking behavior.

A swallowing simulation apparatus 100B of a seventh aspect of the present invention, for example, as illustrated in FIG. 24, in any one of the first aspect to the sixth aspect, further comprises an evaluation/diagnosis unit 60 configured to evaluate or diagnose easiness of eating and/or easiness of drinking of the orally-ingested product based on the behavior of the pseudo-orally-ingested product 20 during swallowed on the movement screen, wherein the movement screen is a virtual movement screen formed in a virtual space by the swallowing simulation apparatus to simulatively display the analysis result of the movements of each of the head-and-neck organs and the behaviors of the pseudo-orally-ingested product 20 during swallowed that are analyzed by the movement analysis unit 50, and the evaluation/diagnosis unit 60 is configured to make evaluation or diagnosis based on whether or not a behavior of the pseudo-orally-ingested product 20 in the virtual movement screen satisfies a predetermined condition.

Here, the virtual movement screen is referred to as a virtual movement screen formed at a virtual space formed by the personal computer PC. However, the virtual movement screen is a movement screen that includes contents same as contents of the movement screen when displayed on the display unit 82. For automatic evaluation or diagnosis, the pseudo-screen display unit 82A is disposed in the computer and the evaluation/diagnosis condition storage unit 83A is disposed in the storage unit 83. Analysis results are dynamically displayed on the virtual movement screen of the pseudo-screen display unit 82A. Then, the analysis results are collated with the evaluation condition or the diagnosis condition of the evaluation/diagnosis condition storage unit 83A for evaluation or diagnosis. The "display on a movement screen" also includes the case where the analysis results are thus dynamically displayed on the virtual movement screen. Predetermined conditions include, for example, the following. An object does not enter the larynx 12, not get stuck to the pharynx 14, and not stick to the tongue 11 or the pharynx 14; a period from introduction in the oral cavity to passing through the esophageal entrance 18a is within a predetermined range; shear stress at the wall surface of the oral cavity is equal to or less than a predetermined value; and shear stress at the periphery of the epiglottis 12a is within a predetermined range. As the predetermined range, for example, the period from the introduction in the oral cavity 17 to passing through the esophageal entrance 18a is 0.8 to 1.0 sec, and the shear stress at the periphery of the epiglottis 12a at 0.8 sec is 0.25 to 0.45 N/m$^2$.

With the configuration of this aspect, the virtual movement screen and the evaluation condition or the diagnosis condition stored in the evaluation/diagnosis condition storage unit 83A are collated. Thus, easiness of eating and/or easiness of drinking of the orally-ingested product can be automatically evaluated or diagnosed.

The swallowing simulation apparatus 100B of a eighth aspect of the present invention, for example, as illustrated in FIG. 2, in the first aspect or the seventh aspect, further comprises an evaluation/diagnosis-result recording unit 83B configured to record an evaluation result or a diagnosis result related to easiness of eating and/or easiness of drinking of the orally-ingested product based on the analysis result of the behavior of the pseudo-orally-ingested product 20 during swallowed, and a physical property determiner 70 configured to determine a physical property of the orally-ingested product regarded as appropriate based on the evaluation or diagnosis result recorded in the evaluation/diagnosis-result recording unit 83B.

Here, the swallowing simulation apparatus 100B automatically determines the physical property based on the evaluation result or the diagnosis result. An aspect of determination by a human (for example, an evaluator or a person to diagnose) is also possible. However, the physical property determiner 70 may be absent here. The physical property determiner 70 is not used even if provided, or the determination result is displayed by the display unit 82 and is provided to the evaluator or the person to diagnose as a reference.

To solve the above-described problem, a dynamic three-dimensional model of a head-and-neck 10a including a head-and-neck organ according to a ninth aspect of the present invention, for example, as illustrated in FIGS. 4A and 4B, comprises a model of a tongue 11 as one of head-and-neck organs, where the model of the tongue 11 has a structure divided into n pieces of sector portions 11a to 11e in a near-far direction, wherein n is an integer equal to or more than 2, while a mental region 16a of a mandible as an origin of a genioglossus 11f is set to a pivot of sector; wherein each of the sector portions is configured to vibrate in cooperation with one another while having predetermined phase differences in a radial direction so as to perform a traveling wave movement by movements of organs to transport the pseudo-orally-ingested product 20 toward a far-side direction.

This configuration allows providing the dynamic three-dimensional model of the head-and-neck 10a that can approximately reproduce the behaviors of the tongue 11 and the throat during swallowing.

The dynamic three-dimensional model of the head-and-neck 10a according to a tenth aspect of the present invention, for example, as illustrated in FIGS. 6A to 6C and FIGS. 7A to 7B, in the ninth aspect, the model of the tongue has a structure where a dome shape portion of each of the sector portions 11a to 11e overlaps with a dome shape portion of another such that a gap is not formed between the sector portions 11a to 11e when each of the sector portions 11a to 11e vibrates and the dome shape portion is for forming a surface of the tongue, the model of the tongue further has a structure where a tongue surface portion 11g that has both right and left sides extending in the radial direction and has a depression in a central portion between the right and left sides is overlapped with each of the sector portions 11a to 11e and each of the sector portions 11a to 11e vibrates in a circumferential direction in the depression of the tongue surface portion 19 in a static state, the model of the tongue is configured to be set such that the sector portions 11a to 11e rotate by a predetermined angle toward a far side in a circumferential direction during swallowing and then the pseudo-orally-ingested product 20 is pushed toward the far side by the sector portion 11e at a farthest side of the tongue 11;

the dynamic three-dimensional model of the head-and-neck 10a has a structure where the head-and-neck includes a tongue 11, a palate 15, a pharynx 14, a larynx portion 12c, trachea 13 and a gullet 18, the larynx portion 12c is divided into an epiglottis 12a and a larynx 12, an esophageal entrance 18a of the gullet 18 is configured to be closed before swallowing is started, and the esophageal entrance 18a is configured to extend and the pharynx 14 is configured to contract during swallowing; and the dynamic three-dimensional model of the head-and-neck is configured to be set such that the larynx 12 is configured to be moved in a direction to the mental region 16a of the mandible to open the esophageal entrance 18a, the pharynx is configured to contract, and then the epiglottis 12a is configured to be rotated by a predetermined angle toward the far side so as to close an esophageal entrance 18a during swallowing.

With this configuration, the flow passage of the pseudo-orally-ingested product 20 is formed in the depression without forming gaps between the respective sector portions 11a to 11e. Then, the pseudo-orally-ingested product 20 is smoothly transported to the far side. This allows providing the dynamic three-dimensional model of the head-and-neck that can approximately reproduce the behavior of the tongue 11, the pharynx 14, the larynx 12, and the gullet 18 during swallowing.

To solve the above-described problem, a swallowing simulation method according to an eleventh aspect of the present invention, for example, as illustrated in FIG. 23 (see FIG. 2 for configuration), comprises, a head-and-neck modeling step (S010) of forming a dynamic three-dimensional model of a head-and-neck 10a that includes head-and-neck organs, an organ-movement setting step (S030) of setting a movement of each of the head-and-neck organs in the dynamic three-dimensional model of the head-and-neck 10a, an orally-ingested-product physical-property setting step (S040) of setting an orally-ingested product as an analysis target and a physical property of the orally-ingested product, an input step (S050) of inputting a pseudo-orally-ingested product 20 formed by modeling the orally-ingested product to an oral cavity, a movement analyzing step (S060) of analyzing the movement of each of the head-and-neck organs in the dynamic three-dimensional model of the head-and-neck 10a and a behavior of the pseudo-orally-ingested product 20 during swallowed using a particle method, and a display step (S070) of displaying an analysis result of the movement of each of the head-and-neck organs and the behavior of the pseudo-orally-ingested product 20 during swallowed that are analyzed in a three-dimensional space in the movement analyzing step (S060), on a movement screen.

With this configuration, for the dynamic three-dimensional model of the head-and-neck 10a, the movements of the head-and-neck organs and the physical properties of the orally-ingested product are set to analyze the behavior of the orally-ingested product using the particle method. This allows providing the swallowing simulation method that facilitates approximately reproducing the actual phenomenon of swallowing.

A swallowing simulation method according to a twelfth aspect of the present invention, for example, as illustrated in FIG. 25, in the eleventh aspect, further comprises, an evaluation step (S080) of evaluating easiness of eating and/or easiness of drinking of the orally-ingested product based on the analysis result of the behavior of the pseudo-orally-ingested product 20 during swallowed, and a physical property determination step (S090) of determining a physical property of the orally-ingested product regarded as appropriate based on an evaluation result evaluated in the evaluation step (S080).

With the configuration of this aspect, a physical property of the orally-ingested product with appropriate easiness of eating and/or easiness of drinking of the orally-ingested product can be efficiently derived with high accuracy through the simulation that facilitates the approximate reproduction of the actual phenomenon of swallowing.

A program according to the thirteenth aspect of the present invention is a program readable by a computer, wherein the program is configured to make the computer execute the swallowing simulation method according to the eleventh or the twelfth aspect.

Here, the program may be stored in a storage unit built into the computer. The program may be downloaded from the Internet. The program may be stored in a memory medium readable by the computer. The computer according to this aspect includes a computer of an apparatus configured including the computer (for example, the personal computer PC) like the swallowing simulation apparatus.

An orally-ingested-product development assistance apparatus 200A according to a fourteenth aspect of the present invention, for example, as illustrated in FIG. 26, comprises the swallowing simulation apparatus 100B according to the eighth aspect, an orally-ingested-product prototype result recording unit 83C configured to record a result of an experimental production performed under an appropriately-set production condition to have the physical property determined as appropriate by the physical property determiner 70, and a production condition determiner 84 configured to determine a production condition that sets a physical property of the orally-ingested product to the physical property determined as appropriate by the physical property determiner 70 based on a prototype result recorded in the orally-ingested-product prototype result recording unit 83C.

With this configuration, the orally-ingested-product development assistance apparatus 200A sets the movement of the head-and-neck organ and the physical property of the orally-ingested product regarding the dynamic three-dimensional model of the head-and-neck 10a so as to analyze the behavior of the orally-ingested product using the particle method. This facilitates reproducing the actual phenomenon of swallowing. Additionally, this swallowing simulation apparatus that facilitates reproducing the actual phenomenon of swallowing is used for evaluation or diagnosis of the orally-ingested product. This allows reliably developing an orally-ingested product excellent in easiness of eating and easiness of drinking.

The orally-ingested-product development assistance apparatus 200A according to a fifteenth aspect of the present invention, for example, as illustrated in FIG. 26, in the fourteenth aspect, further comprises, an evaluation/diagnosis unit 60 configured to evaluate or diagnose easiness of eating and/or easiness of drinking of the orally-ingested product based on the behavior of the pseudo-orally-ingested product 20 during swallowed, on the movement screen, wherein the movement screen is a virtual movement screen formed in a virtual space by the swallowing simulation apparatus 100B to simulatively display the analysis result of the movement of each of the head-and-neck organs and the behavior of the pseudo-orally-ingested product 20 during swallowed that are analyzed by the movement analysis unit 50, and the evaluation/diagnosis unit 60 is configured to make evaluation or diagnosis based on whether or not a behavior of the pseudo-orally-ingested product in the virtual movement screen satisfies a predetermined condition.

With the configuration of this aspect, the orally-ingested-product development assistance apparatus 200A collates the virtual movement screen and the evaluation condition or the diagnosis condition stored in the evaluation/diagnosis condition storage unit 83A to automatically evaluate or diagnose easiness of eating and/or easiness of drinking, so as to associate the evaluation result or the diagnosis result with the development of an orally-ingested product. This allows efficiently developing an easy-to-eat or easy-to-drink orally-ingested product.

An orally-ingested-product development method according to a sixteenth aspect of the present invention comprises, for example, as illustrated in FIG. 27, the swallowing simulation method according to the twelfth aspect, wherein the orally-ingested-product physical-property setting step (S040) includes a step of changing the physical property of the orally-ingested product to set, and a step of repeatedly performing a subsequent process up to the physical property determination step (S090), or a step of changing the physical property of the orally-ingested product to set, a step of repeatedly performing a subsequent process up to the evaluation/diagnosis step (S080), and then collectively performing the physical property determination step (S090), the orally-ingested-product development method further comprises an orally-ingested-product prototype production step (S110) of performing an experimental production under an appropriately-set production condition to have the physical property determined as appropriate in the physical property determination step (S090), and a production condition determination step (S120) of determining a production condition that gives a physical property of the orally-ingested product to the physical property determined as appropriate in the physical property determination step (S090) based on the result in the orally-ingested-product prototype production step (S110).

With the configuration of this aspect, the orally-ingested-product development method sets the movement of the head-and-neck organ and the physical property of the orally-ingested product regarding the dynamic three-dimensional model of the head-and-neck 10a so as to analyze the behavior of the orally-ingested product using the particle method. This facilitates reproducing the actual phenomenon of swallowing. Additionally, this swallowing simulation method that facilitates reproducing the actual phenomenon of swallowing is used for evaluating the orally-ingested product. This allows reliably developing an orally-ingested product excellent in easiness of eating and/or easiness of drinking.

According to an orally-ingested-product development method according to a seventeenth aspect of the present invention, for example, as illustrated in FIG. 27, in the sixteenth aspect, the movement screen is a virtual movement screen formed at a virtual space by a swallowing simulation apparatus 100B to simulatively display an analysis result of a movement of each of the head-and-neck organs and a behavior of the pseudo-orally-ingested product 20 during swallowed, the analysis result is analyzed in the movement analysis step (S060), the display step (S070) is a virtual display step to simulatively display the analysis result on the virtual movement screen, and the evaluation/diagnosis step (S080) evaluates or diagnoses whether the behavior of the pseudo-orally-ingested product 20 on the virtual movement screen simulatively displayed in the virtual display step meets a predetermined condition or not.

With the configuration of this aspect, the orally-ingested-product development assistance apparatus 200A collates the virtual movement screen and the evaluation condition or the diagnosis condition stored in the evaluation/diagnosis condition storage unit 83A to automatically evaluate or diagnose easiness of eating and easiness of drinking of the orally-ingested product, so as to associate the evaluation result or the diagnosis result with the development of an orally-ingested product. This allows efficiently developing an easy-to-eat or easy-to-drink orally-ingested product.

An orally-ingested-product production method according to an eighteenth aspect of the present invention, for example, as illustrated in FIG. 28, comprises a step of producing the orally-ingested product using a production condition determined in the production condition determination step (S120) of the orally-ingested-product development method according to the sixteenth aspect or the seventeenth aspect.

Typically, the orally-ingested-product development method repeatedly performs simulation to check for an appropriate physical property. Then, the orally-ingested product is developed by determining the production condition such that the physical property of the orally-ingested product becomes appropriate. In the orally-ingested-product production method, when an orally-ingested product is produced using the production condition determined in the production condition determination step (S120) of the orally-ingested-product development method in any of step in the production process (for example, a raw material combination step and a baking step), this corresponds to the aspect.

This configuration allows reliably developing an orally-ingested product excellent in easiness of eating and easiness of drinking.

To solve the above-described problem, a dietary education assistance apparatus 300A according to a nineteenth aspect of the present invention, for example, as illustrated in FIG. 29, comprises, the swallowing simulation apparatus 100A (or 100B) according to the first aspect or the seventh aspect of the present invention, an evaluation/diagnosis-result recording unit 83B configured to record an evaluation result or a diagnosis result of easiness of eating and easiness of drinking of the orally-ingested product based on the analysis result of the behavior of the pseudo-orally-ingested product during swallowed, and a teaching unit 85 configured to explain the behavior of the pseudo-orally-ingested product 20 during swallowed displayed on the movement screen by the display unit 82 associating with the evaluation result or the diagnosis result of the orally-ingested product recorded in the evaluation/diagnosis-result recording unit 83B.

This aspect is the dietary education assistance apparatus 300A applying the swallowing simulation apparatus 100A according to the first aspect. Here, teaching may be performed by a teacher using the movement screen or/and a teaching material. The content to be taught may be installed in the dietary education assistance apparatus to allow audio output in conjunction with the moving image, and the dietary education assistance apparatus 300A may automatically perform teaching through audio output. The teaching unit 85 may automatically create the teaching contents based on the evaluation result or the diagnosis result. However, it is preferred that the teaching contents be edited and supplemented for easier understanding by an educator. Here, the swallowing simulation apparatus 100B according to the seventh aspect may be applied instead of the swallowing simulation apparatus 100A according to the first aspect.

With this configuration, the swallowing phenomenon is displayed using the swallowing simulation apparatus, which facilitates the reproduction of actual phenomenon of swallowing. Accordingly, easiness of eating or easiness of drinking of the orally-ingested product is easily understood, effective in dietary education.

To solve the above-described problem, a dietary education method according to a twentieth aspect of the present invention, for example as illustrated in FIG. 30, comprises the swallowing simulation method according to the eleventh aspect, an evaluation step (S080) of evaluating easiness of eating and/or easiness of drinking of the orally-ingested product based on the analysis result of the behavior of the pseudo-orally-ingested product 20 during swallowed, and a teaching step (S082) of explaining the behavior of the pseudo-orally-ingested product 20 during swallowed displayed on the movement screen in the display step (S070) associating with the evaluation result of the orally-ingested product evaluated in the evaluation step (S080).

This aspect is a dietary education method corresponding to the dietary education assistance apparatus 300A according to the nineteenth aspect. With this configuration, the swallowing phenomenon is displayed using the swallowing simulation method, which facilitates the reproduction of actual phenomenon of swallowing. Accordingly, easiness of eating or easiness of drinking of the orally-ingested product is easily understood by a person to be taught, effective in dietary education.

A swallowing simulation apparatus 400A according to a twenty-first aspect of the present invention, for example as illustrated in FIG. 31, in the swallowing simulation apparatus 100A, 100B according to any one of the first aspect to the eighth aspect, further comprises, an organ movement determiner 75 configured to determine an organ movement parameter fitting to a symptom of a diagnosed person based on the analysis result analyzed in the movement analysis unit 50 in the organ movement parameters set in the organ movement setting unit 30.

This configuration allows finding a functionally-deteriorated portion of each head-and-neck organ to make use of diagnosis.

A diagnosis assistance apparatus according to a twenty-second aspect of the present invention comprises the swallowing simulation apparatus according to the twenty-first aspect.

This configuration allows quick diagnosis taking into consideration the swallowing phenomenon using the swallowing simulation apparatus.

Firstly, the present invention can provide a swallowing simulation apparatus, a dynamic three-dimensional model of a head-and-neck, a swallowing simulation method, a program readable by the computer, an orally-ingested-product development assistance apparatus, an orally-ingested-product development method, an orally-ingested-product production method, a dietary education assistance apparatus, a dietary education method, and a diagnosis assistance apparatus that facilitate approximately reproducing an actual phenomenon of swallowing, that is, behaviors of a head-and-neck organ and an orally-ingested product.

Secondly, the present invention can provide a swallowing simulation apparatus, a dynamic three-dimensional model of a head-and-neck, a swallowing simulation method, a program readable by a computer, an orally-ingested-product development assistance apparatus, an orally-ingested-product development method, an orally-ingested-product production method, a dietary education assistance apparatus, a dietary education method, and a diagnosis assistance apparatus that allows accurately expressing behaviors of a head-and-neck organ and an orally-ingested product during swallowed and that allows quantifying a physical quantity related to a behavior and a physical property of the orally-ingested product.

BRIEF DESCRIPTION OF DRAWINGS

FIG. 13A is a drawing illustrating behaviors of water, milk A and milk B on the tongue at t=0.5 sec (the same time) in analysis results of the three-dimensional simulation.

FIG. 13B is a drawing illustrating behaviors of water, milk A and milk B at the periphery of the epiglottis 12a at t=0.7 sec (the same time) in analysis results of the three-dimensional simulation.

FIG. 21A is a drawing illustrating behaviors of the bolus at a concentration (concentration of a thickness adjusting food product in a water solution) of C=1% to 3% on a tongue at t=0.5 sec in analysis results of the three-dimensional simulation in the case where the bolus is a non-Newtonian fluid.

FIG. 21B is a drawing describing behaviors of the bolus at a concentration (concentration of a thickness adjusting food product in a water solution) of C=1% at a periphery of an epiglottis at t=0.7 sec in analysis results of the three-dimensional simulation in the case where the bolus is the non-Newtonian fluid.

DETAILED DESCRIPTION OF THE INVENTION

Figure 1A:
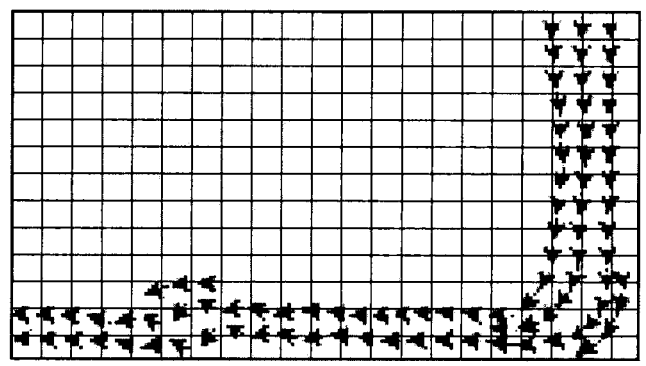
FIG. 1A is a drawing illustrating a conceptual diagram of a lattice method for illustrating a difference between the lattice method and a particle method.

The present application is based on Japanese Patent Application No. 2012-072178 filed on Mar. 27, 2012 in Japan. The content forms part thereof as the content of the present application. The present invention will be more completely understood by the detailed description provided hereinafter. Further areas of applicability of the invention will become more apparent from the detailed description provided hereinafter. However, it should be understood that the detailed description and specific examples indicate desired embodiments of the invention, and are provided for the purpose of illustration only because it will be apparent to those skilled in the art that various modifications and variations can be made without departing from the spirit or scope of the present invention from the detailed description. Applicants have no intention to present any described embodiments to the public, and among modifications and variations, the subject matter that may not be fallen within the scope of claims should also be part of the invention under the doctrine of equivalents.

Embodiments of the present invention will be described below by referring to the accompanying diagrams. Like reference numerals designate corresponding or identical elements throughout the drawings, and therefore such elements will not be further elaborated here.

(Particle Method)

According to the embodiment, as an analysis method that allows expressing, for example, a large deformation of a liquid surface and a spray, the particle method that treats liquid and solid analysis targets as particles is employed for simulations. First, the particle method will be described.

Figure 1B:
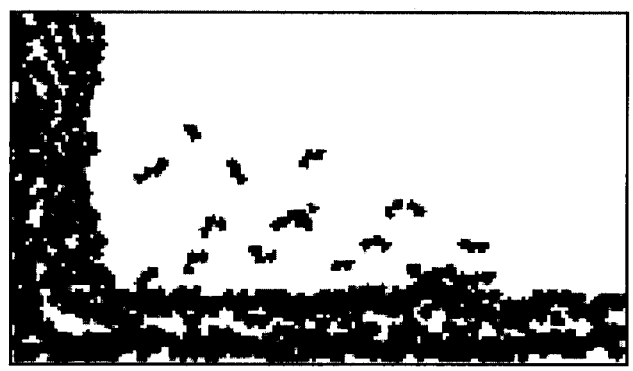
FIG. 1B is a drawing illustrating a conceptual diagram of the particle method for illustrating the difference between the lattice method and the particle method.

FIGS. 1A and 1B illustrate a difference between a lattice method, which is the conventional analysis method, and the particle method, which is a new analysis method. FIG. 1A illustrates a conceptual diagram of the lattice method while FIG. 1B illustrates a conceptual diagram of the particle method. The lattice method divides an analysis region by grid and calculates physical quantities of each grid. That is, a change in the liquid surface goes along a shape of the grid. Accordingly, analyses of when the spray occurs and the liquid surface is largely deformed is difficult. In contrast to this, the particle method, especially an Moving Particle-Semi-implicit (MPS) method is comparatively new analysis method, which was developed in 1995 (Koshizuka et al, Comput. Fluid Dynamics J, 4, 29-46, 1995). The particle method replaces a fluid with particles and calculates physical quantities of each particle. As a result, a subtle change in the liquid surface can be analyzed, allowing analyses when the spray occurs and the liquid surface is largely deformed. However, analyses of fluids and boluses in a living body using the particle method have not been found up to the present. Therefore, the inventors have developed the simulation apparatus and the simulation method where the particle method is applied to estimation of behaviors of the fluid and the bolus in the living body.

In the two-dimensional swallowing simulator (Japanese patent application No. 2011-146780 and Japanese patent application No. 2011-146781) by the particle method proposed by the inventors, as an analysis method, the particle method can be used to reproduce a large deformation of a bolus surface and a spray that have been difficult with the conventional technique.

However, there has been a further request for three-dimensionally and accurately expressing a behavior of a head-and-neck organ such as an oral cavity organ or a throat organ, and a behavior of a food/drink product, or the like during swallowed compared with a simulation in a two-dimensional space. Additionally, the limitation on the program to be used causes a problem that it is difficult to quantify the physical quantity related to the behavior and the physical property of the orally-ingested product.

To solve the above-described problem, the inventors have developed a three-dimensional swallowing simulator. The two-dimensional swallowing simulator has been able to perform analysis using a simplified structure on a single plane. The three-dimensional simulator has further reproduced accurate structure and accurate behavior of the oral cavity, the pharynx, and the larynx portion based on medical knowledge. Additionally, the three-dimensional swallowing simulator has allowed quantitative evaluation or diagnosis by improvement so that the physical properties (such as a density, a viscosity, a surface tension, a contact angle, a heat capacity, a thermal conductivity, and a dynamic friction coefficient) of the orally-ingested product (the bolus) set as non-dimensional relative values in the two-dimensional swallowing simulator can be set as numerical values with dimensions and also the physical quantities (such as a period of time, a position coordinate, a speed, a pressure, a temperature, a shear rate, a normal stress, and a shear stress) of the bolus during swallowed can be extracted as numerical values with dimensions.

First Embodiment (Apparatus Configuration)

Figure 2:
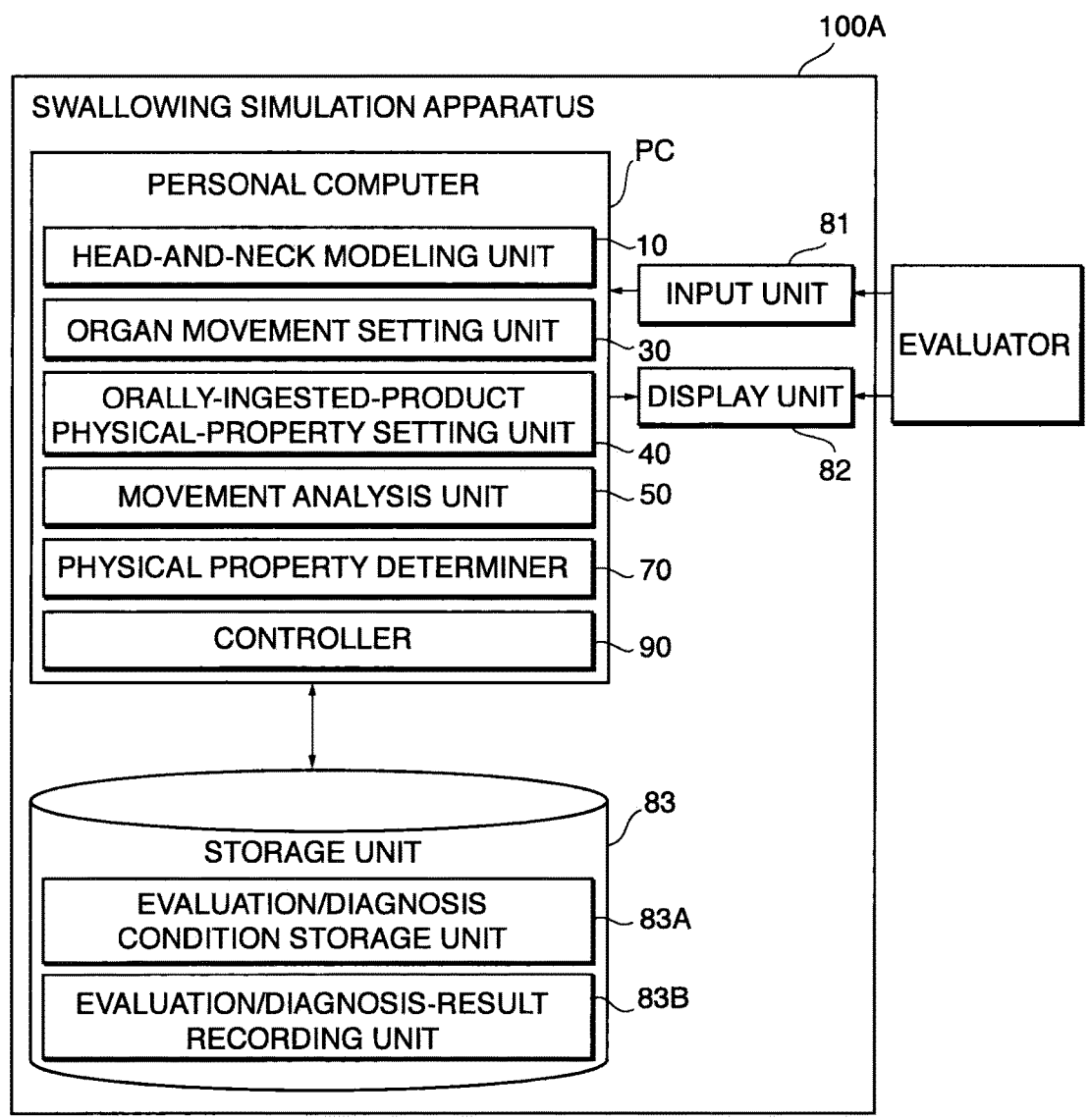
FIG. 2 is a drawing illustrating an exemplary configuration of a swallowing simulation apparatus according to Embodiment 1.

FIG. 2 illustrates an exemplary configuration of a swallowing simulation apparatus 100A according to Embodiment 1. Embodiment 1 describes an exemplary swallowing evaluation or swallowing diagnosis made by inputting the orally-ingested product and by viewing the moving image by the evaluator or the person to diagnose. Refer to FIG. 3 for the exemplary configuration of a dynamic three-dimensional model of a head-and-neck 10a.

The swallowing simulation apparatus 100A includes a head-and-neck modeling unit 10, an organ movement setting unit 30, an orally-ingested-product physical-property setting unit 40, an input unit 81, a movement analysis unit 50, a display unit 82, a physical property determiner 70, a controller 90, and a storage unit 83.

The head-and-neck modeling unit 10 forms the dynamic three-dimensional model of the head-and-neck 10a that includes the head-and-neck organs. The organ movement setting unit 30 sets the movement of each of the head-and-neck organs in the dynamic three-dimensional model of the head-and-neck 10a (hereinafter also referred to simply as a model of the head-and-neck). The orally-ingested-product physical-property setting unit 40 sets an orally-ingested product as an analysis target and the physical property of the orally-ingested product. The input unit 81 inputs a pseudo-orally-ingested product (including a pseudo-food/drink product, a pseudo-medicinal product, or a pseudo-nonmedicinal product) 20 formed by modeling the orally-ingested product to the oral cavity. The movement analysis unit 50 analyzes the movement of each of the head-and-neck organs in the model of the head-and-neck 10a and the behavior of the pseudo-orally-ingested product 20 during swallowed in a three-dimensional space using the particle method.

The display unit 82 displays the analysis result on the movement of each of the head-and-neck organs and the behavior of the pseudo-orally-ingested product 20 during swallowed that are analyzed by the movement analysis unit 50 on a movement screen. The physical property determiner 70 determines the physical property of the orally-ingested product regarded as appropriate based on the evaluation result or the diagnosis result obtained such that the evaluator or the person to diagnose makes evaluation or diagnosis of the orally-ingested product viewing the movement screen. The controller 90 controls the swallowing simulation apparatus 100A and the respective units of the swallowing simulation apparatus 100A, and make the swallowing simulation apparatus 100A and the respective units execute various functions of the swallowing simulation apparatus 100A. The storage unit 83 stores the dynamic three-dimensional model of the head-and-neck 10a, the setting conditions (such as an organ movement and the physical property of the orally-ingested product), the analysis result, and the evaluation result or the diagnosis result. The display unit 82 also displays the model of the head-and-neck 10a, the setting condition (such as the organ movement, and the physical property of the orally-ingested product), the evaluation result or the diagnosis result, and the like on the screen.

In these members, the head-and-neck modeling unit 10, the organ movement setting unit 30, the orally-ingested-product physical-property setting unit 40, the movement analysis unit 50, the physical property determiner 70, and the controller 90 can be achieved in the personal computer PC and disposed inside of the personal computer PC. The evaluator or the person to diagnose makes evaluations or diagnoses observing the movement screen on the display unit 82 and inputs the evaluation results or the diagnosis results from the input unit 81. The evaluation results input or the diagnosis results input are recorded in an evaluation/diagnosis-result recording unit 83B of the storage unit 83. Here, the case where the simulation is performed by a doctor or a dentist in a checkup or a medical practice to evaluate the analysis result is referred to as diagnosis that is distinguished from evaluation made by an ordinary person. That is, in this description, the evaluation does not include diagnosis.

As the target for the swallowing simulation, an orally-ingested product including a medicinal product and a non-medicinal product other than the food/drink product can be used. In some cases, a material that is not orally ingested (for example, a marble) can be also treated as a target of the swallowing simulation for validation of accidental ingestion and choking. When the orally-ingested product is liquid, the orally-ingested-product physical-property setting unit 40 sets physical properties of for example, a fluid volume, a degree of viscosity, a surface tension, a specific gravity, a thermal conductivity, and a specific heat. When the orally-ingested product is a solid, the orally-ingested-product physical-property setting unit 40 sets physical properties of, for example, a shape, a size, an elastic modulus, tension strength, a yield point, yield point stress, shear rate dependence of degree of viscosity, dynamic viscoelasticity, static viscoelasticity, compressive stress, breaking stress, breaking strain, hardness, stickiness, an aggregating property, a thermal conductivity, and a specific heat. When the orally-ingested product is a semisolid (with plasticity but without fluidity), the orally-ingested-product physical-property setting unit 40 sets physical properties of, for example, an amount, a degree of viscosity, a specific gravity, a yield point, yield point stress, shear rate dependence of degree of viscosity, dynamic viscoelasticity, static viscoelasticity, compressive stress, stickiness, and an aggregating property.

The dynamic three-dimensional model of the head-and-neck 10a is preferred to be funned in accordance with the actual movement of the oral cavity organ and temporally deform for performing accurate analysis. Therefore, the entire model is preferred be treated as particles (a rigid substance, powders, an elastic body, a plastic body, and an elasto-plastic body). However, when the number of particles is increased, the load on the computer PC that performs analysis in the three-dimensional space is increased. Accordingly, it is efficient to perform analysis while the head-and-neck organ is set as a polygon so as to simplify and facilitate the analysis.

The input unit 81 includes an input device such as the computer mouse and the keyboard. The input unit 81 injects a pseudo-orally-ingested product 20 to be injected into the oral cavity. With the computer mouse, for example, a cursor is dragged and dropped in the oral cavity, an injection position of the pseudo-orally-ingested product 20 in the oral cavity is, for example, set near the teeth in the oral cavity (for example, within twice the length of the pseudo-orally-ingested product), and time immediately after the dragging and dropping is set as injection time.

The movement analysis unit 50 analyzes a behavior of the pseudo-orally-ingested product 20 (hereinafter also referred to simply as an orally-ingested product) during swallowed in association with the movement of the head-and-neck organ. The orally-ingested product that is injected into the head and neck is moved by the traveling wave movement of a tongue 11, the rotational movement of an epiglottis 12a, the reciprocating movement of a larynx 12, and the like. The motion of the orally-ingested product is analyzed by the particle method. The orally-ingested product is treated as a polygon or particles in any forms of solid, semisolid, and liquid (sometimes treated as a polygon for reducing a computation load).

The display unit 82 displays an analysis result of the behavior of the orally-ingested product on the movement screen. One exposure of the moving image can be displayed as a still image. Tracing back the time and displaying the images while being rewound are also possible.

The storage unit 83 stores, for example, a model of a head-and-neck 10a, organ properties, a setting condition, an analysis result, and an evaluation result or a diagnosis result.

The evaluation or diagnosis is made by the evaluator or the person to diagnose viewing the movement screen on the display unit 82. "Good", "poor", a rank, a score, or the like is input to a cell in an evaluation table or a diagnosis table displayed on the display unit 82, for example. The evaluation result or the diagnosis result is recorded in the evaluation/diagnosis-result recording unit 83B. An appropriate physical property value of the orally-ingested product can be obtained by making evaluation or diagnosis while changing the physical property value of the orally-ingested product by the orally-ingested-product physical-property setting unit 40. The physical property determiner 70 automatically determines the physical property of the orally-ingested product regarded as appropriate based on the evaluation result or the diagnosis result recorded in the evaluation/diagnosis-result recording unit 83B. Here, the case where a human makes a determination is illustrated in Embodiment 4. The number of physical properties may be a single or plural. The appropriate physical property may be, for example, indicated by creating a map within an appropriate range, may be indicated by classifying an appropriate range into a plurality of levels (for example, rank A to rank C), may be indicated by plurality of points, or may be indicated by an optimum one point. When many types of physical properties are to be obtained, the appropriate physical property range may be obtained using multidimensional analysis of principal component.

The controller 90 controls the swallowing simulation apparatus 100A and each unit of the swallowing simulation apparatus 100A and make the swallowing simulation apparatus 100A and the respective units execute the respective functions of the swallowing simulation apparatus 100A. The controller 90 includes a swallowing simulator (analysis software) in a built-in memory.

(Head-and-Neck Model)

Figure 3A:
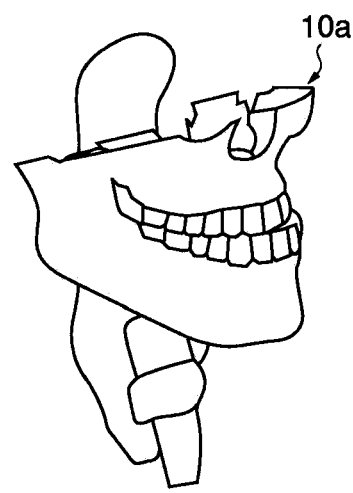
FIG. 3A is a drawing describing a perspective view of an exemplary configuration of a model of a head-and-neck according to Embodiment 1.
Figure 3B:
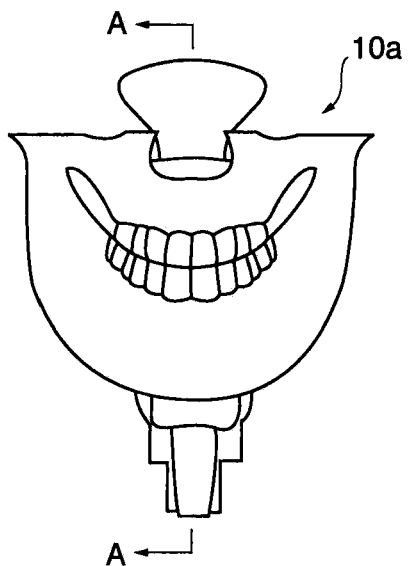
FIG. 3B is a drawing describing a front view of the exemplary configuration of the model of the head-and-neck according to Embodiment 1.
Figure 3C:
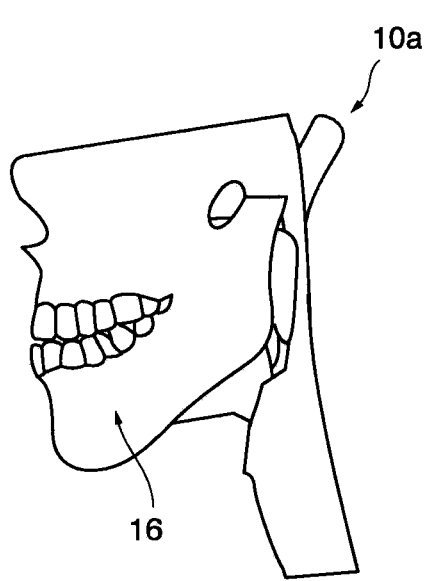
FIG. 3C is a drawing describing a side view of the exemplary configuration of he model of the head-and-neck according to Embodiment 1.
Figure 3D:
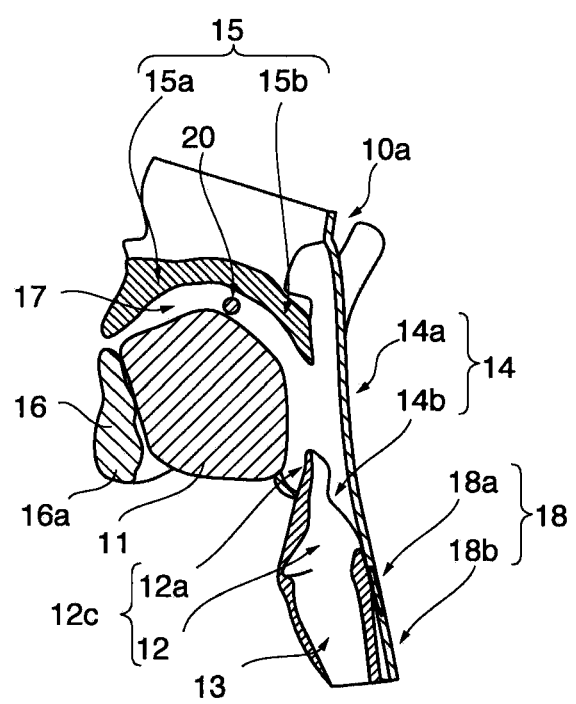
FIG. 3D is a drawing describing a cross-sectional view taken along A-A of the exemplary configuration of he model of the head-and-neck according to Embodiment 1.

FIGS. 3A to 3D describe an exemplary configuration of a model of a head-and-neck 10a according to this embodiment. FIG. 3A describes a perspective view, FIG. 3B describes a front view, FIG. 3C describes a side view, and FIG. 3D describes a cross-sectional view taken along A-A of the model of the head-and-neck 10a. In the drawings, reference numeral 11 denotes a tongue (including a genioglossus 11f (see FIGS. 4A and 4B)). Reference numeral 12 denotes a larynx. Reference numeral 12a denotes an epiglottis. Reference numeral 13 denotes a trachea. Reference numeral 14 denotes a pharynx (reference numeral 14a denotes a tube wall of the pharynx and reference numeral 14b denotes a pharyngeal mucosa). Reference numeral 15 denotes a palate (reference numeral 15a denotes a hard palate and reference numeral 15b denotes a soft palate). Reference numeral 16 denotes a jaw (including a mental region 16a). Reference numeral 17 denotes an oral cavity. Reference numeral 18 denotes a gullet (reference numeral 18a denotes an esophageal entrance and reference numeral 18b denotes a tube wall of the gullet). Reference numeral 20 denotes a ball-like bolus as the pseudo-orally-ingested product.

In the particle method, an increase in the number of particles increases the load on the computer, thus costing time for analysis. In this embodiment, the orally-ingested product is expressed as particles (fluid). The respective oral cavity organs are expressed as a wall boundary (a boundary in which a wall that is not moved by receiving an external force from fluid or the like is arranged in the space as the distance function) generated by a polygon distance function. This simplifies the model of the head-and-neck 10a, thus reducing the load on the computer. The movement (the traveling wave movement, the rotational movement, the reciprocating movement, and the like) of each head-and-neck organ is set by the organ movement setting unit 30.

When the model of the head-and-neck 10a was generated, the positions of the pharynx 14 and the esophageal entrance 18a were estimated based on knowledge of the structure understood by dissection and the forms of the soft palate 15b, the tongue 11 and the trachea 13 that can be roughly read by a computed tomography (CT) image. The structures of the tongue 11, the soft palate 15b, the pharynx 14, the esophageal entrance 18a, the epiglottis 12a and the larynx 12 were modeled using software (such as Autodesk 3ds Max) for computer graphics (CG). Subsequently, on the obtained dynamic three-dimensional model of the head-and-neck 10a, videofluoroscopic-images (in front view and in side view) during swallowing by videofluoroscopic examination of swallowing (VF) were superposed to modify the three-dimensional structure. Furthermore, as the outline of a three-dimensional change in spatial domain, the motion is given by referring to the moving images of cine magnetic resonance imaging (cine MRI) of swallowing. Here, the cine MRI is a developed method of the principle (a synchronous sampling method) of a cardiography by synchronization with heartbeat. Firstly, an input of a trigger to an MRI apparatus at a regular interval and a swallowing movement in synchronization with the trigger are repeated so as to obtain an MRI moving image with a plurality of cross sections. This moving image is three-dimensionally configured, and then arranged on the time axis so as to obtain a four-dimensional image.

Using the model of the head-and-neck 10a in FIG. 3A to 3D, the swallowing movement was simulated. For the simulation, the model of the head-and-neck 10a was expressed using the distance function. In the particle method, the organ at the shortest distance from the orally-ingested product (particle) in a spatial point (three-dimensional coordinate) has an intense action. As the distance becomes farther, the action becomes less intense. The distance function is a function defined by the shortest distance from the spatial point (three-dimensional coordinate) to the model of the head-and-neck 10a. Using the distance function can facilitate superposition of the model of the head-and-neck 10a (the minimum values of the distances from all the head-and-neck organs are defined in the spatial points). The facilitated superposition of the model of the head-and-neck 10a allows reproduction of the swallowing movement by superposition after individually setting the movement amounts of the respective divided head-and-neck organs.

(Tongue Model)

Figure 4A:
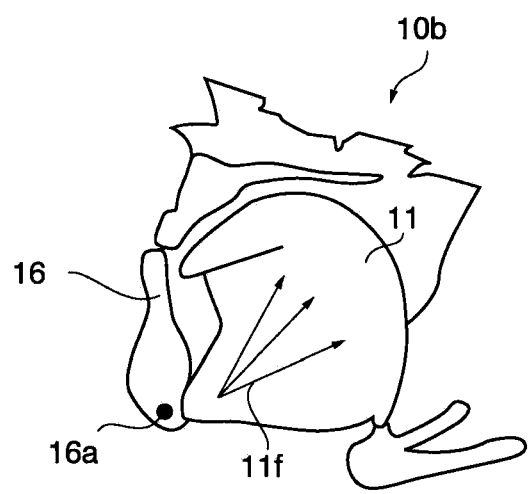
FIG. 4A is a drawing illustrating an arrangement of the muscle of a tongue in an exemplary configuration of a model of the tongue.
Figure 4B:
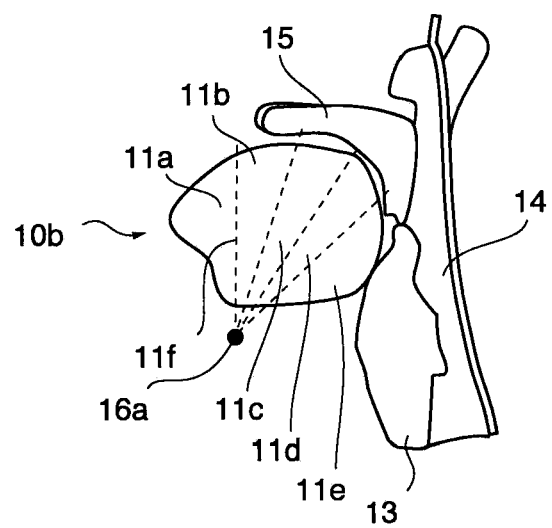
FIG. 4B is a drawing illustrating an exemplary configuration of the model of the tongue 10b sectorally divided along the genioglossus.

FIGS. 4A and 4B illustrates an exemplary configuration of a model of a tongue 10b. FIG. 4A illustrates an arrangement of the muscle (the genioglossus 11f extending from the mental region 16a of the mandible) of the tongue 11. FIG. 4B illustrates the model of the tongue 10b sectorally divided along the genioglossus 11f. The model of the tongue 10b is formed by the head-and-neck modeling unit 10, and the movement of the tongue is set by the organ movement setting unit 30. It is necessary to reproduce transportation of the bolus by the tongue 11 for the model of the tongue 10b. The model of the tongue 10b has a structure where the mental region 16a of the mandible that is the origin of the genioglossus is set to the pivot of the sector and the tongue 11 is divided into a sector shape along the genioglossus 11f extending from the origin. The division is performed, for example, by n divisions (n=5 in this embodiment) in the front-back direction assuming that the lip is the front side and the throat is the back side but the division is not performed in the lateral direction. The respective divided portions are referred to as sector portions 11a to 11e. The transportation of the orally-ingested product by the movement of the tongue 11 is achieved by vibrating the respective sector portions 11a to 11e in the radial direction and shifting the vibration phase from the front side toward the back side. For example, the vibration is set such that the vibration is generated around the genioglossus 11f with an amplitude of 5 mm at a vibration frequency of 1.1 Hz and the vibration timings (the phases) of the respective sector portions 11a to 11e are delayed from the near-side toward the far-side in series by 0.1 sec.

Figure 5A:
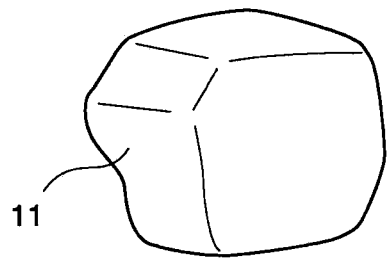
FIG. 5A is a drawing illustrating another exemplary configuration (an early exemplary configuration) of the model of the tongue before dividing.
Figure 5B:
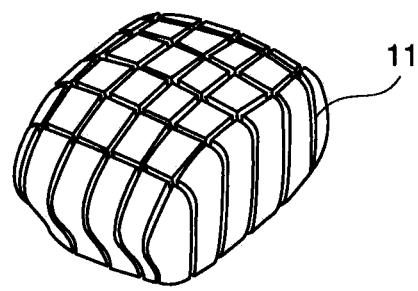
FIG. 5B is a drawing illustrating another exemplary configuration (the early exemplary configuration) of the model of the tongue after dividing.

FIGS. 5A and 5B are drawings illustrating another exemplary configuration (an early exemplary configuration) of the model of the tongue. FIG. 5A illustrates the model of the tongue before dividing, and FIG. 5B illustrates the model of the tongue after dividing. As illustrated in FIG. 5B, a model in which the tongue 11 was divided by 6×6=36 was examined in an early stage. However, it was not possible to reproduce the smooth movement of the tongue 11 as expected. Additionally, 36 divisions increased the load on a personal computer (PC). Thus, analysis was not normally performed. Accordingly, consideration on minimizing the dividing results in the model in FIGS. 4A and 4B. However, when the processing capacity of the PC is improved, there is a possibility for using a multi-division model, for example, by 36 divisions.

While in this embodiment the model by dividing the tongue 11 is used to reduce the computation load, it is possible to read the model of the tongue with a deformed shape without dividing for each calculation time so as to simulate a smoother traveling wave movement.

Figure 6A:
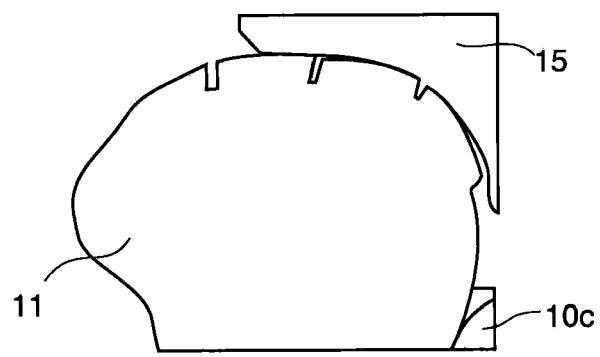
FIG. 6A is a drawing illustrating a tongue structure before an overlap of the tongue structure.
Figure 6B:
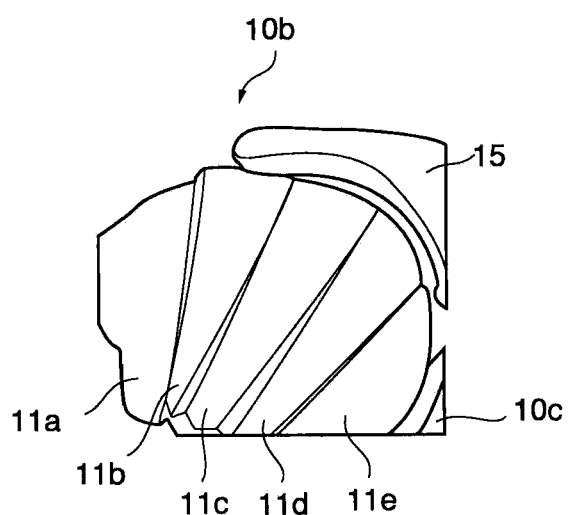
FIG. 6B is a drawing illustrating a tongue structure after the overlap of the tongue structure.
Figure 6C:
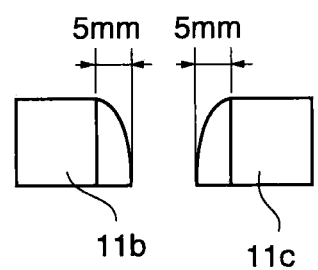
FIG. 6C is a drawing illustrating the detail of the overlap of the tongue structure.

FIGS. 6A to 6C describe an overlap of the tongue structure. FIG. 6A illustrates a tongue structure before the overlap, FIG. 6B illustrates a tongue structure after the overlap, and FIG. 6C illustrates the detail of the overlap. When vibration movements of the respective sector portions 11a to 11e of the tongue 11 are simply performed before the overlap, as illustrated in FIG. 6A, the cut surfaces appear outside at the gaps between the respective sector portions 11a to 11e. Therefore, as illustrated in FIGS. 6B and 6C, dome shapes with a height of, for example, 5 mm are formed on the cut surfaces of the respective sector portions 11a to 11e to overlap two structures such that the cuts do not appear.

Figure 7A:
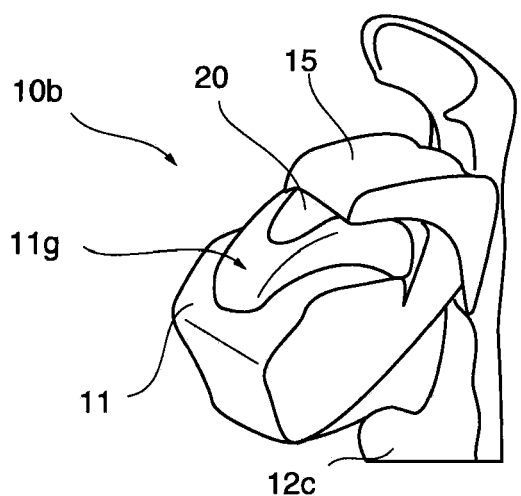
FIG. 7A is a drawing describing a perspective view for illustrating a model in which the tongue structures (sector portions) in a normal condition overlaps with a tongue structure (a tongue surface portion) having a flow passage depressed in the center.
Figure 7B:
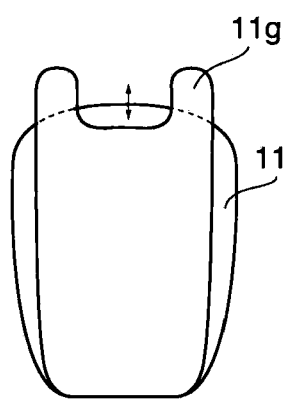
FIG. 7B is a drawing illustrating the motions of tongue structures (sector portions) in a normal condition with respect to the tongue structure (the tongue surface portion) having the flow passage depressed in the center.

FIGS. 7A and 7B are drawings for illustrating a tongue structure that has a flow passage depressed in the center. FIG. 7A is a perspective view for illustrating a model in which the tongue structure in a normal condition overlaps with a tongue structure (a tongue surface portion) 11g depressed in the center. FIG. 7B is a drawing for illustrating the motions of tongue structures (sector portions) 11a to 11e in a normal condition with respect to the tongue structure (the tongue surface portion) 11g depressed in the center. In FIG. 7B, in the portion illustrated as the tongue 11, the respective sector portions 11a to 11e overlap with one another in the front-back direction. The tongue structures 11a to 11e in a normal condition are the tongue structures in FIGS. 6B and 6C, and the tongue structure (the tongue surface portion) 11g depress in the center is the structure where both right and left sides extend in the radial direction and the central portion is depressed. This tongue structure 11g depressed in the center is overlapped with the tongue structures 11a to 11e in a normal condition. Then, both the right and left sides of the tongue structure 11g depressed in the center extend in the radial direction so as to constitute wall surfaces. The surfaces of the tongue structures (the respective sector portions) 11a to 11e in a normal condition vibrate in the radial direction in the depression of the tongue structure 11g depressed in the center (vibrate in a vertical direction in FIG. 7B). Based on the medical knowledge that the bolus 20 is gathered in the center of the tongue 11 and then flowed down by the transportation of the tongue 11, the tongue structure 11g depressed in the center immediately before swallowing is added so as to ensure a flow passage of the bolus (the pseudo-orally-ingested product) 20.

Furthermore, the amplitudes of the respective sector portions 11a to 11e in the radial direction are set to, for example, 10 to 15 mm. In addition to the vibration movement during swallowing, for example, the rotational movement (rotation by 15° in total around the pivot of the sector during vibration) by 15° is given to the far side in the circumferential direction of the respective sector portions 11a to 11e. The transportation of the bolus is performed by the vibration and the rotational movement of the sector portions 11a to 11e with the shifted phases. Here, the above-described amplitude, vibration frequency, vibration timing, overlap height, and rotation angle are examples, and can be arbitrarily set in a preferred range (for example, ±20%).

Furthermore, in the sector portion 11e on the farthest side of the tongue 11, the pseudo-orally-ingested product 20 is pushed toward the far side. For example, a specific motion of pushing by the sector portion 11e toward the far side is as follows. Until the timing of swallowing, the sector portion 11e vibrates with an amplitude of 10 mm similarly to the other sector portions 11a to 11d and rotates simultaneously. Here, while the other sector portions 11a to 11d performs a movement of rotation by 15 degrees spending 0.3 second, the sector portion 11e on the farthest side stops rotating in 0.1 second (rotates only by 5 degrees) and then inversely rotates by 15 degrees spending 0.2 second. During this inverse rotation, the vibration movement around the pivot of the sector shape shows the behavior that has the maximum amplitude at the beginning time of the inverse rotation and gradually falls down to the rotational center side. Afterward, the sector portion 11e rotates by 10 degrees in 0.2 second, and then returns to the state almost before the swallowing and waits for the next swallowing movement. During this returning, the pseudo-orally-ingested product 20 is pushed toward the far side.

The analysis performed while the gravity direction was changed using this model of the tongue 10b allowed to confirm that the transportation of the bolus (here, with the physical property of water) 20 by the movement of the tongue 11 is achieved in any gravity direction.

(Laryngeal Model)

It is necessary to reproduce the state where the entrance of the gullet 18 is closed in a normal condition and the gullet 18 opens during swallowing. A model of a laryngeal 10c realizes opening and closing of the gullet 18 and the larynx 12 by the motions of the epiglottis 12a and the larynx 12. The model of the laryngeal 10c is formed by the head-and-neck modeling unit 10, and the movement of the model of the laryngeal 10c is set by the organ movement setting unit 30.

Figure 8:
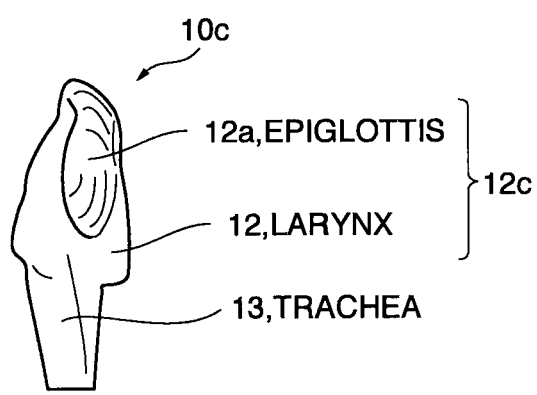
FIG. 8 is a drawing illustrating an exemplary configuration of the model of the laryngeal according to Embodiment 1.

FIG. 8 illustrates an exemplary configuration of the model of the laryngeal 10c. The model of the laryngeal 10c includes the epiglottis 12a and the larynx 12. The epiglottis 12a has a hole in communication with the larynx 12. The larynx 12 has a tube shape, and the epiglottis 12a is a bank-like raised portion in the peripheral area of the tube of the entrance (the laryngeal inlet) of the larynx 12. A reciprocating movement is performed such that the larynx 12 mounted with the epiglottis 12a moves to the direction of the mental region 16a of the mandible and to its opposite side, and a rotational movement is performed such that the epiglottis 12a rotates on the larynx 12. Here, the movement of the larynx 12 and the rotation of the epiglottis 12a progress simultaneously. During this movement, the pharynx 14 is shortened in the upper direction and the lumen contracts.

Figure 9A:
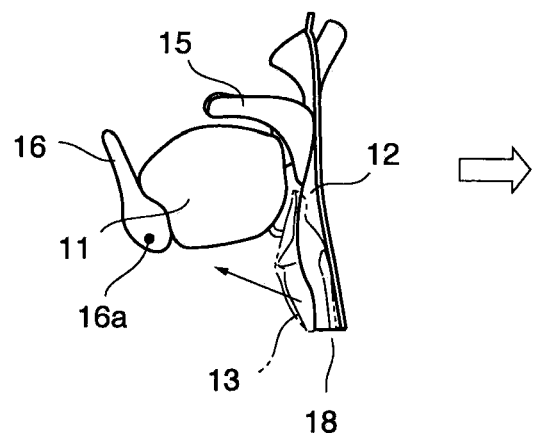
FIG. 9A is a drawing illustrating an esophageal entrance in a closed state before a larynx is moved (in a normal condition) for illustrating movement of the larynx and opening of the esophageal entrance in the dynamic three-dimensional model of the head-and-neck.
Figure 9B:
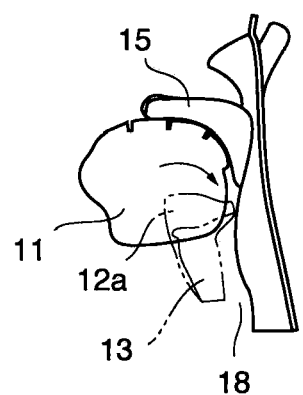
FIG. 9B is a drawing illustrating the esophageal entrance in an opening state after the larynx is moved for illustrating movement of the larynx and opening of the esophageal entrance in the dynamic three-dimensional model of the head-and-neck.
Figure 9C:
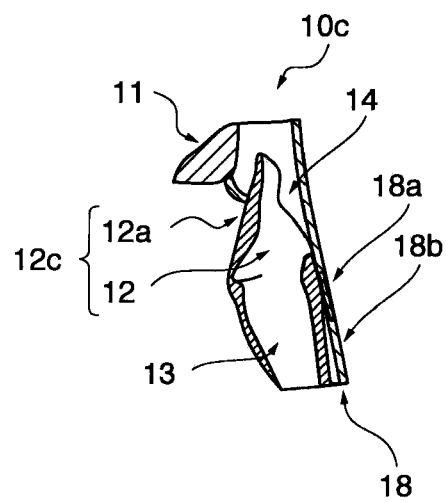
FIG. 9C is a drawing illustrating the cross section of model of a laryngeal in a normal condition (when an esophageal entrance is in the closed state) for illustrating movement of the larynx and opening of the esophageal entrance in the dynamic three-dimensional model of the head-and-neck.

FIGS. 9A to 9C illustrate the movement of the larynx 12 and opening of the esophageal entrance 18a in the dynamic three-dimensional model of the head-and-neck 10a. FIG. 9A illustrates the esophageal entrance 18a in a closed state before the larynx 12 is moved (in a normal condition). FIG. 9B illustrates the esophageal entrance 18a in an opening state after the larynx 12 is moved. FIG. 9C is a drawing illustrating the cross section of a model of the laryngeal 10c in a normal condition (when the esophageal entrance 18a is in a closed state). As illustrated in FIGS. 9A and 9B, in a normal condition, the larynx 12 is located in the obliquely downward direction of the mental region 16a of the mandible. During swallowing, the larynx 12 is moved in the direction to the mental region 16a of the mandible in the obliquely upward direction such that the esophageal entrance 18a is opened. The arrow in FIG. 9A denotes the moving direction of a larynx portion 12c. As illustrated in FIG. 9C, the esophageal entrance 18a in a normal condition is closed by the upper esophageal sphincter. The anterior wall of the gullet 18 is in contact with the posterior wall of the trachea 13.

Figure 10A:
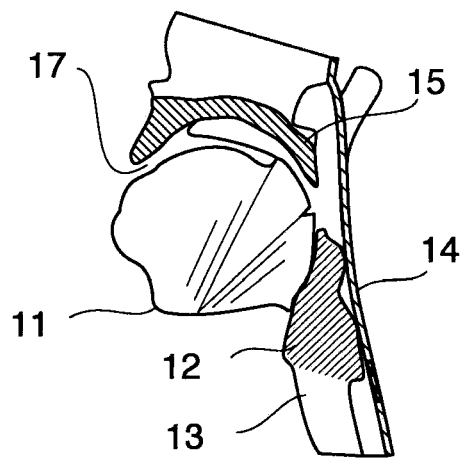
FIG. 10A is a drawing illustrating a state before a rotational movement of an epiglottis in a model of a laryngeal.
Figure 10B:
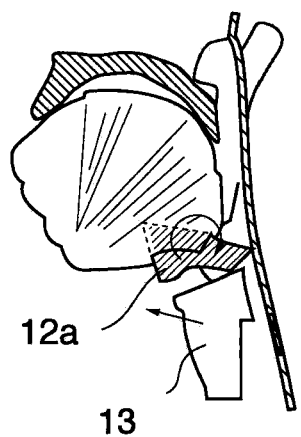
FIG. 10B is a drawing illustrating a state after the rotational movement of the epiglottis in the model of the laryngeal.

FIGS. 10A and 10B illustrate the rotational movement of the epiglottis 12a in the model of the laryngeal 10c. FIG. 10A illustrates a state before the rotation. FIG. 10B illustrates a state after the rotation. FIG. 10B illustrates the moving direction of the larynx 12 and the rotation direction of the epiglottis 12a by arrows. The angle of the rotation is set to, for example, 135 degrees in the light of the realistic motion. During swallowing, the larynx 12 moves to the mental region 16a side of the mandible such that the esophageal entrance 18a is opened, and the entrance of the larynx 12 is covered by the rotational movement of the epiglottis 12a.

Figure 11A:
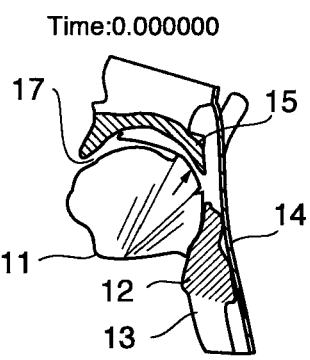
FIG. 11A is a drawing illustrating the states at 0.0 sec of an exemplary interlocking movement of the larynx and the epiglottis.
Figure 11B:
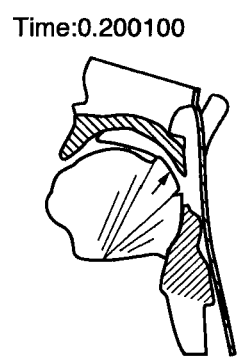
FIG. 11B is a drawing illustrating the states at 0.2 sec of the exemplary interlocking movement of the larynx and the epiglottis.
Figure 11C:
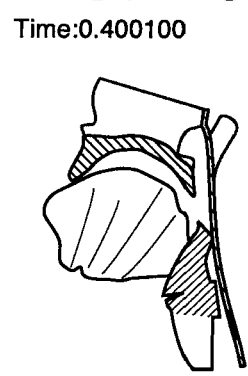
FIG. 11C is a drawing illustrating the states at 0.4 sec of the exemplary interlocking movement of the larynx and the epiglottis.
Figure 11D:
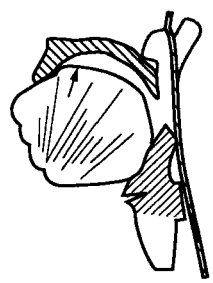
FIG. 11D is a drawing illustrating the states at 0.5 sec of the exemplary interlocking movement of the larynx and the epiglottis.
Figure 11E:
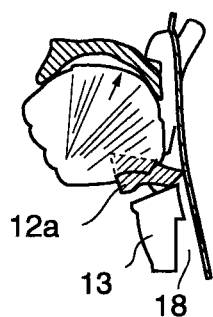
FIG. 11E is a drawing illustrating the states at 0.6 sec of the exemplary interlocking movement of the larynx and the epiglottis.
Figure 11F:
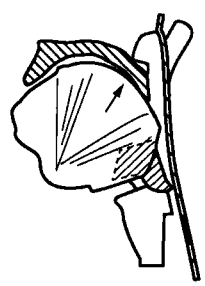
FIG. 11F is a drawing illustrating the states at 0.7 sec of the exemplary interlocking movement of the larynx and the epiglottis.
Figure 11G:
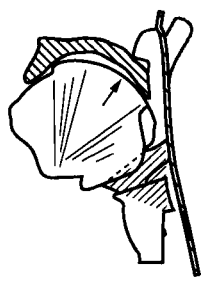
FIG. 11G is a drawing illustrating the states at 0.8 sec of the exemplary interlocking movement of the larynx and the epiglottis.
Figure 11H:
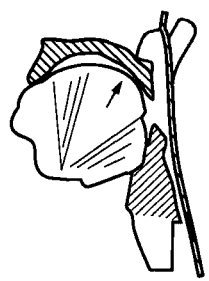
FIG. 11H is a drawing illustrating the states at 0.9 sec of the exemplary interlocking movement of the larynx and the epiglottis.
Figure 11I:
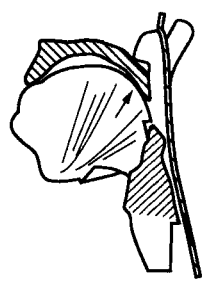
FIG. 11I is a drawing illustrating the states at 1.0 sec of the exemplary interlocking movement of the larynx and the epiglottis.

FIGS. 11A to 11I illustrate an exemplary interlocking movement of the larynx 12 and the epiglottis 12a in the model of the laryngeal 10c (in which the larynx portion is denoted by reference numeral 12c). FIG. 11A illustrates the states at 0.0 sec, FIG. 11B illustrates the states at 0.2 sec, FIG. 11C illustrates the states at 0.4 sec, FIG. 11D illustrates the states at 0.5 sec, FIG. 11E illustrates the states at 0.6, FIG. 11F illustrates the states at 0.7 sec, FIG. 11G illustrates the states at 0.8 sec, FIG. 11H illustrates the states at 0.9 sec, and FIG. 11I illustrates the states at 1.0 sec. The epiglottis 12a starts to incline at 0.2 sec, laid on its side at 0.6 sec, reaches the maximum angle of 135 degrees at 0.7 sec, then inversely rotates, and returns to the original state at 1.0 sec. The larynx 12 starts to move at 0.6 sec, reaches the maximum angle at 0.7 sec, and returns to the original state at 0.9 sec. The arrow in the drawing illustrates the topmost portion of the tongue (the sector portion) 11. Here, the movement in which the farthest portion 11e of the tongue (the sector portion) pushes an object toward the far side by 5 mm at the moment when the epiglottis 12a is laid as described above is incorporated.

(Swallowing Simulator)

A simulator (analysis software) to perform the swallowing simulation method according to this embodiment models the head-and-neck organ and analyzes the behaviors of the fluid and/or the bolus while passing through the oral cavity and the throat using the particle method.

From the analysis results using the simulator, for example, the following are performed.

(a) Estimations of risks of a swallowing, an accidental swallowing, an accidental ingestion, and choking depending on a difference in a physical property value of an orally-ingested product.

(b) Estimations of a swallowing period depending on the difference in the physical property value of the orally-ingested product.

(c) Estimations of a force and shear stress applied to the throat wall (the tube wall of the trachea or the pharynx) depending on the difference in the physical property value of the orally-ingested product.

(d) Evaluations or diagnoses on easiness of drinking, easiness of eating, difficulty of drinking, and difficulty of eating for the orally-ingested product from the correlations between the above-described data and a sensory evaluation or a sensory diagnosis.

The evaluations or diagnoses are made by the evaluator or the person to diagnose, or automatically made by the swallowing simulation apparatus. In this embodiment, these are made by the evaluator or the person to diagnose.

The swallowing simulator has been created using three-dimensional particle method analysis software. A physical property value of a fluid and time, for example, can be directly input to the analysis software as a numerical value, and physical quantities of the physical property value of the fluid and time can be appropriately changed, featuring a quantitative analysis.

(Analysis Case 1)

An orally-ingested product (a bolus) with various physical properties is adapted to the swallowing movement in the three-dimensional particle method analysis software installed in the swallowing simulator to analyze the behavior of the bolus during swallowed. Firstly, water was taken as the pseudo-orally-ingested product 20, and the physical property values of water were substituted so as to perform analysis.

Table 1 illustrates the physical property values of water used in the analysis. Unlike the two-dimensional simulator, numerical values with units are substituted into the physical property values. The particle diameter of the particles used in the analysis was set to 1 mm, and the bolus with about 3 nil was injected. Here, the particle diameter of the particles can be set to any value by the movement analysis unit 50.

TABLE 1

| Setting of Physical Property Value (Water) | |
| --- | --- |
| Density [kg/m³] | 1000 |
| Viscosity [mPa · s] | 1.00 |
| Surface Tension [mN/m] | 72.0 |

Figures 12A, 12B:
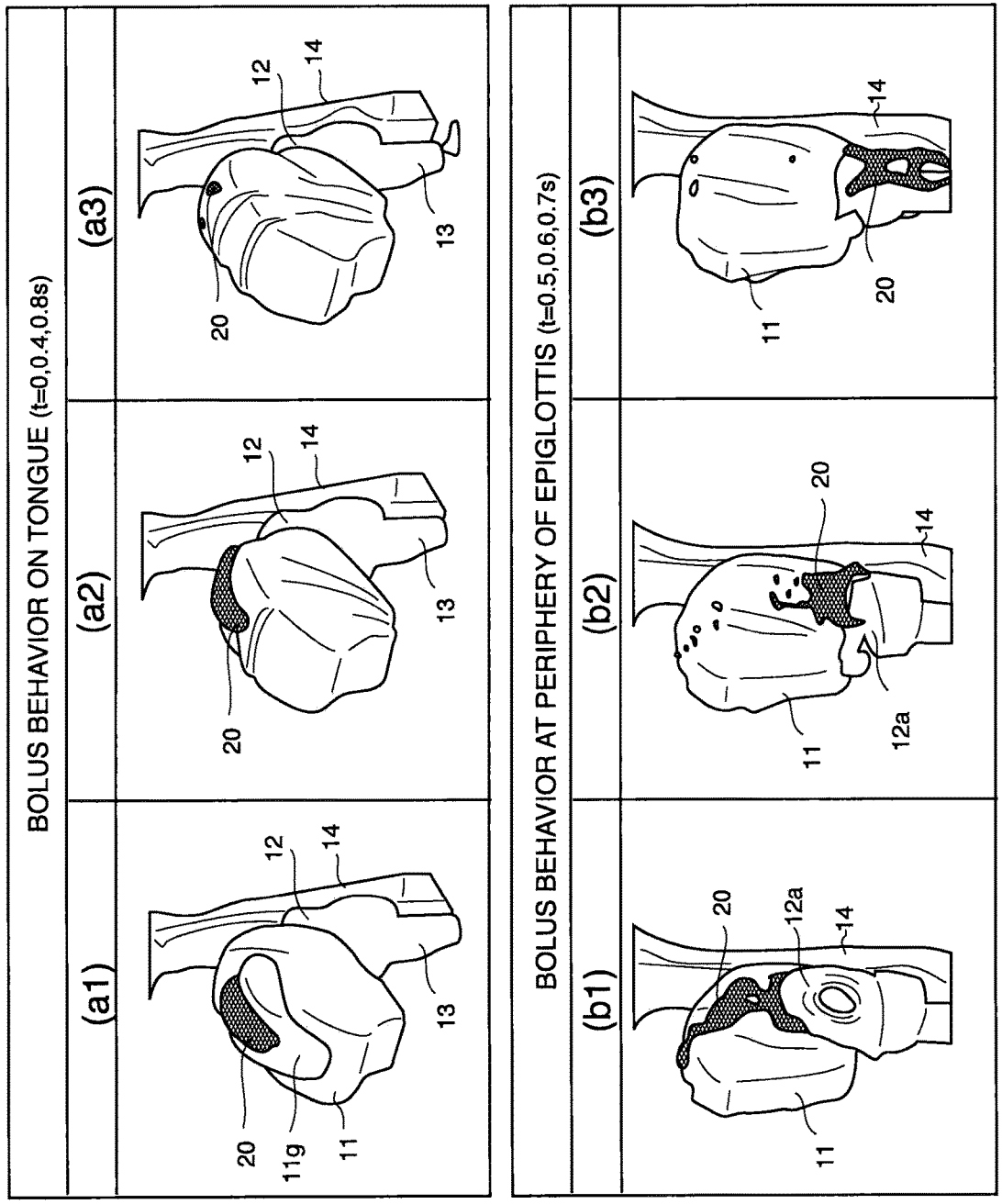
FIG. 12A is a drawing illustrating the behaviors of water on the tongue in analysis results of a three-dimensional simulation.
FIG. 12B is a drawing illustrating the behaviors of water at the periphery of the epiglottis in analysis results of the three-dimensional simulation.

FIGS. 12A and 12B illustrate analysis results of the three-dimensional simulation in the case where the bolus is water. In FIG. 12A, FIGS. (a1) to (a3) illustrate the behaviors of the bolus on the tongue 11. In FIG. 12B, FIGS. (b1) to (b3) illustrate the behaviors of the bolus at the periphery of the epiglottis 12a. In FIG. 12A, FIG. (a1) illustrates the behaviors of water at t=0 sec, (a2) illustrates the behaviors of water at t=0.4 sec, In FIG. 12B, FIG. (b1) illustrates the behaviors of water at t=0.5 sec, FIG. (b2) illustrates the behaviors of water at t=0.6 sec, FIG. (b3) illustrates the behaviors of water at t=0.7 sec. And in FIG. 12A, FIG. (a3) illustrates the behaviors of water at t=0.8 sec. By these drawings, it is apparent that the transportation by the tongue 11 and injection of the bolus into the gullet 18 by lying of the epiglottis 12a can be reproduced. A part of particles remains on the tongue 11 and at the periphery of the epiglottis 12a, and flows in the larynx 12 side without flowing down to the gullet 18. These phenomena can be quantified by the number of particles in the analysis using the particle method. It is possible to quantitatively evaluate or diagnose the residue in throat, the risk of accidental swallowing, and the like.

(Analysis Case 2)

Next, as the orally-ingested product, three types of liquid, water, milk A (ordinary milk), and milk B ("Meiji Oishii Gynnyu" made by Meiji Co., Ltd., (which is registered trademark of Meiji Co., Ltd.)) were injected, and the behaviors were analyzed.

Table 2 illustrates the physical properties of these three types of liquid.

TABLE 2

| Physical Property of Analyzed Bolus | | | |
| --- | --- | --- | --- |
|  | Water | Milk A | Milk B |
| Density [kg/m³] | 1000 | 1029.6 | 1029.6 |
| Viscosity [mPa · s] | 1.00 | 3.03 | 3.07 |
| Surface Tension [mN/m] | 72.0 | 48.6 | 47.1 |

FIGS. 13A and 13B illustrate analysis results of the three-dimensional simulation in the case where the orally-ingested product (the bolus) is water, milk A, and milk B. In FIG. 13A, FIGS. (a1) to (a3) illustrate behaviors of the bolus on the tongue 11 at t=0.5 sec (the same time). In FIG. 13B, FIGS. (b1) to (b3) illustrate behaviors of the bolus at the periphery of the epiglottis 12a at t=0.7 sec (the same time). In these figures, FIGS. (a1) and (b1) illustrate the behaviors of water, FIGS. (a2) and (b2) illustrate the behaviors of milk A, and FIGS. (a3) and (b3) illustrate the behaviors of milk B. It was found that variation of the behavior at the same time due to the difference in physical property of the orally-ingested product was able to be observed from the simulation.

(Evaluation or Diagnosis Based on Shear Stress and Flow-Down Speed)

Next, regarding the orally-ingested product (the bolus) with the physical properties on Table 2, analysis of the shear stress and the flow-down speed was performed so as to obtain a quantitative analysis result.

Figure 14:
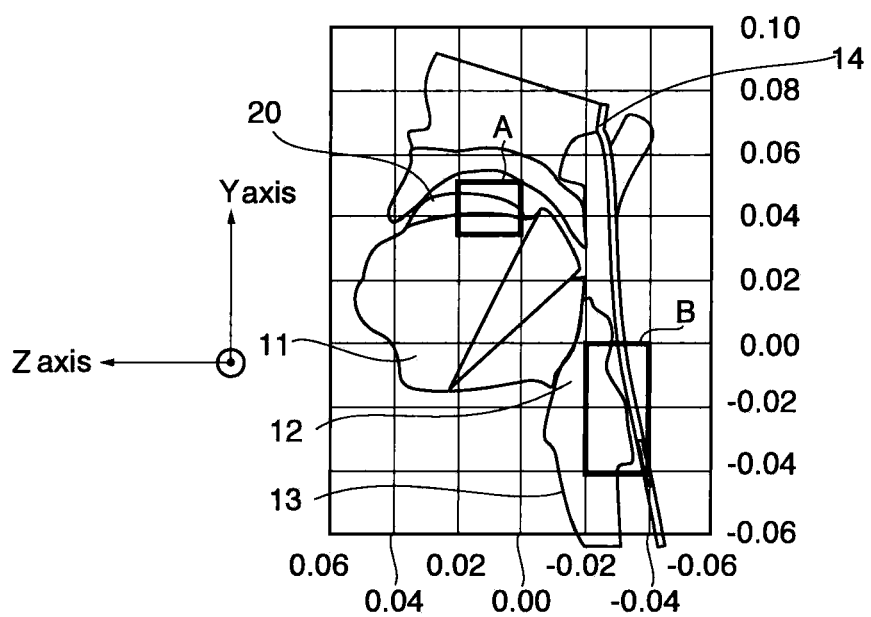
FIG. 14 is a thawing illustrating analyzing areas of the shear stress and the flow-down speed.

FIG. 14 illustrates analyzing areas of the shear stress and the flow-down speed. A shear stress was obtained in an area A on the tongue 11 inside of the oral cavity. A shear stress and a flow-down speed were obtained in an area B of the esophageal entrance 18a inside of the pharynx space.

Figure 15:
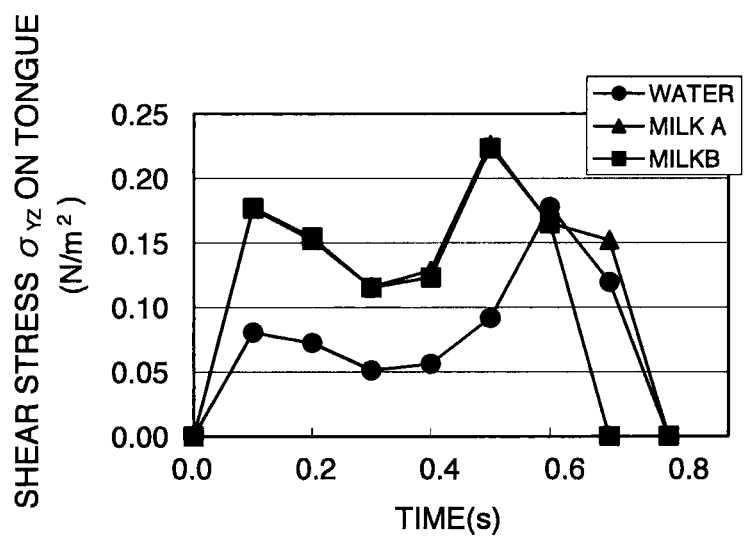
FIG. 15 is a drawing illustrating a secular change in shear stress in the area A.

FIG. 15 illustrates a secular change (output every 0.1 sec) in shear stress in the area A. The average shear stress in the area A can be obtained by the average value of the stress ($\sigma_{YZ}$ component of the stress tensor) when a force in the Z direction with respect to the plane having the normal line in the Y direction is applied to the particle within the area A. At the time when the particles within the area A become equal to or less than 15 due to the transportation of the bolus by the tongue 11, the shear stress was set to 0. This drawing shows that there are two peaks of the shear stress on the tongue 11. Here, the first peak of the shear stress is the shear stress generated when the bolus spreads within the oral cavity at the time of injection of the bolus, and is considered to be an index of the spread within the oral cavity. The second peak of the shear stress is the shear stress on the tongue 11 generated when the bolus is transported by the tongue 11 during swallowing, and is considered to be a value to be one index of feeling in the throat.

Figure 16:
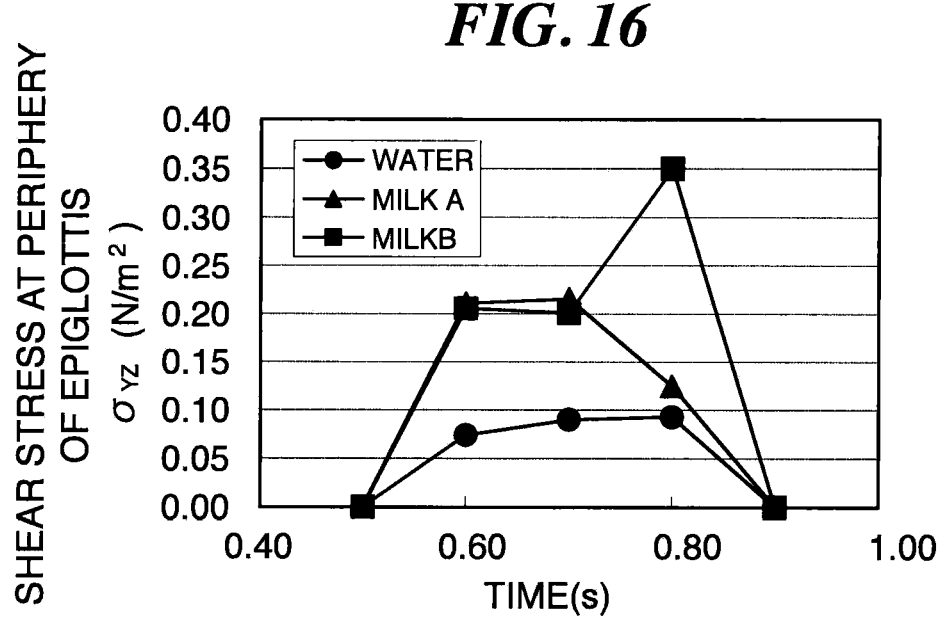
FIG. 16 is a drawing illustrating a secular change in shear stress in the area B.
Figure 17:
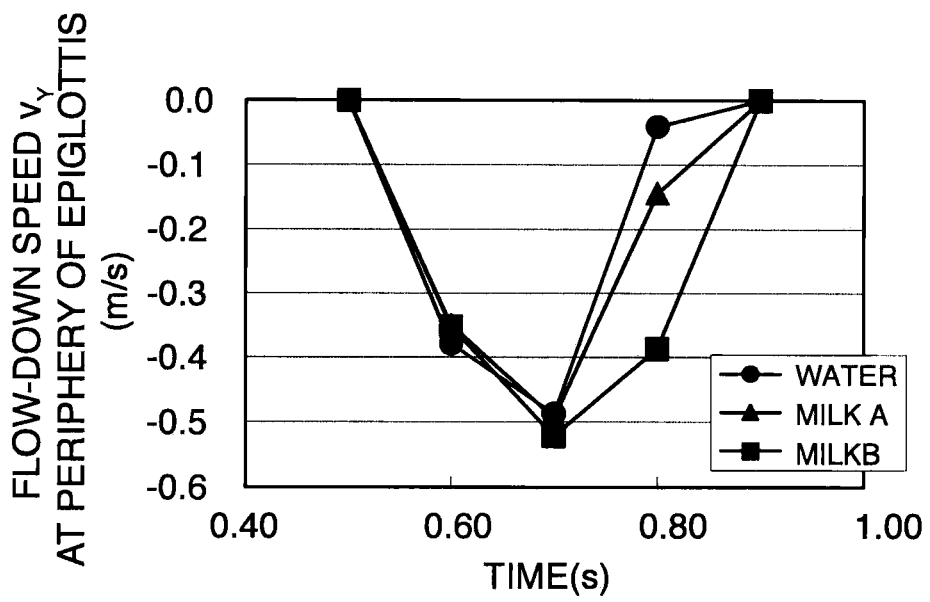
FIG. 17 is a thawing illustrating a secular change in flow-down speed in the area B.

FIG. 16 illustrates a secular change (output every 0.1 sec) in shear stress in the area B. FIG. 17 illustrates a secular change (output every 0.1 sec) in flow-down speed ($v_Y$ component of the speed) in the area B. The average shear stress within the area B can be obtained by the average value of the stress ($\sigma_{ZY}$ component of the stress tensor) when a force in the Y direction with respect to the plane having the normal line in the Z direction is applied to the particle within the area A. At the time when the particles within the area become equal to or less than 15, the shear stress and the flow-down speed were set to 0.

FIG. 16 shows that there is a difference in shear stress between water and milk. Between milk A and milk B, a large difference appeared at swallowing end timing (t=0.8 sec). This is because the flow-down speed at t=0.8 sec is considered to be larger in milk B as illustrated in FIG. 17. While there was not a large difference in physical property value between milk B and milk A, the possibility was suggested that there was a difference in behavior (draining off of liquid and swallowing of the last few drops) at timing for pouring liquid.

Thus, the swallowing simulator allows quantifying the influence to the bolus on the throat due on the slight difference in physical property value. Comparing these with a result of a sensory test or the like allows considering the cause affecting the senses. Further, from a view point of a shear stress, a flow rate, or the like, the influence by the physical properties of an existing product can be mapped.

(Evaluation or Diagnosis Based on Residual Rate and Accidental Swallowing Rate)

Next, regarding the orally-ingested product (the bolus) of the physical properties on Table 2, analysis of the residual rate and the accidental swallowing rate was performed and then a quantitative analysis result was able to be obtained.

Figure 18:
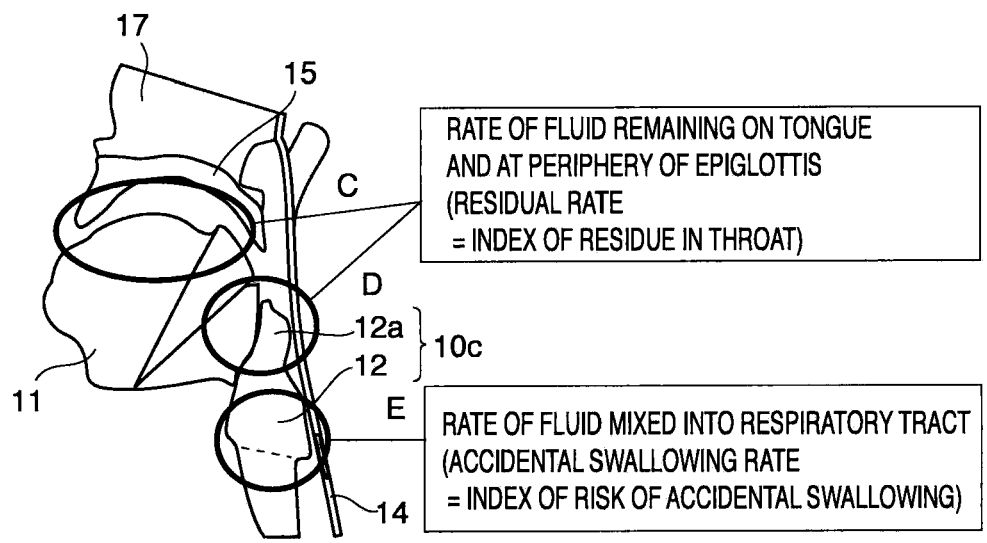
FIG. 18 is a drawing illustrating analyzing areas of the residual rate and the accidental swallowing rate.

FIG. 18 illustrates analyzing areas of the residual rate and the accidental swallowing rate. For an area C, a residual rate was obtained in an area on the tongue 11 inside of the oral cavity 17. For an area D, a residual rate was obtained in an area at the periphery of the epiglottis 12a. For an area E, an accidental swallowing rate was obtained in an area of the outlet of the larynx 12.

Figure 19:
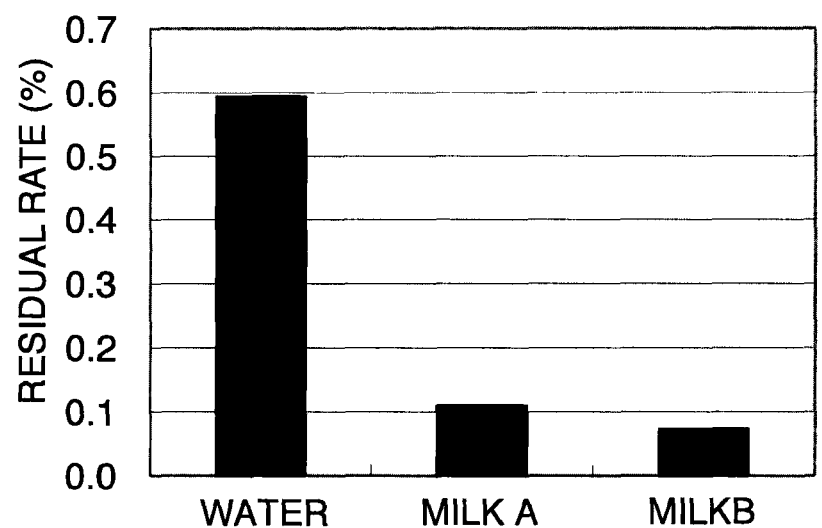
FIG. 19 is a drawing illustrating the residual rates in the area C and the area D (total of both areas).
Figure 20:
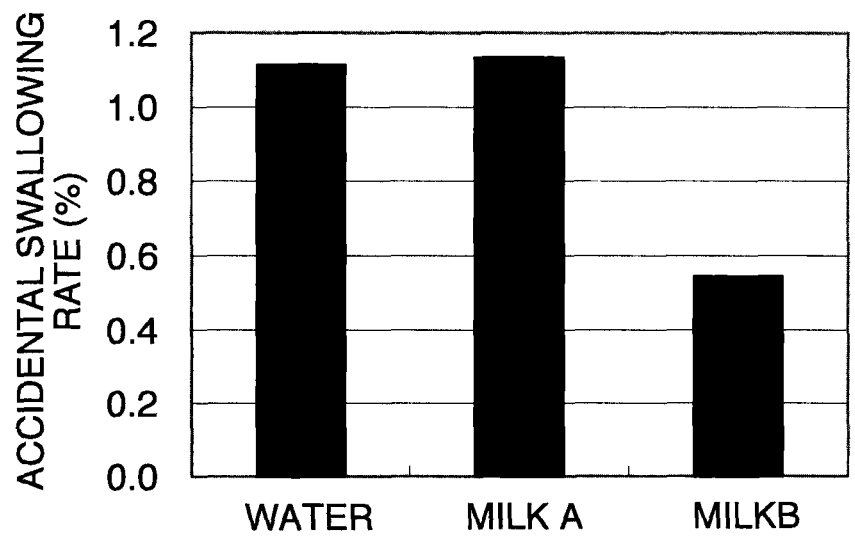
FIG. 20 is a drawing illustrating the accidental swallowing rates in the area E.

FIG. 19 illustrates the residual rates in the area C and the area D (total of both areas). FIG. 20 illustrates the accidental swallowing rates in the area E. The particle method tracks the position of the particle one by one, and thus has an advantage that can easily obtain the amount of particles present in the space. Therefore, the number of particles remaining on the tongue 11 and at the periphery of the epiglottis 12a after the swallowing action was counted as an index (the residual rate) of residue in throat, and then evaluation or diagnosis was made. Furthermore, the outlet (illustrated by a dashed line in FIG. 18) of the larynx 12 was covered to also count the particles mixed into the larynx 12 side, and then evaluation or diagnosis of the risk (the accidental swallowing rate) of the accidental swallowing was also made. However, the evaluation method or diagnosis method by counting particles is a method that can be also performed with the two-dimensional swallowing simulator. Thus, the advantage of the three-dimension is that the physical property values of the bolus to be injected can be defined as numerical values.

As seen in FIG. 19, the result showed that milk had a lower proportion remaining within the oral cavity than that of water. The reason for this was mainly considered that the high viscosity was likely to form a lump. While in FIG. 20 the result showed a low accidental swallowing rate in milk B, the cause for this had not been able to be specified yet.

(Analysis of Non-Newtonian Fluid)

FIGS. 21A and 21B illustrate analysis results of the three-dimensional simulation in the case where the bolus is a non-Newtonian fluid. In FIG. 21A, FIGS. (a1) to (a3) illustrate behaviors of the bolus on the tongue 11 at t=0.5 sec (the same time at 3 cases). IN FIG. 21B, (b1) to (b3) illustrate behaviors of the bolus at the periphery of the epiglottis 12a at t=0.7 sec (the same time at 3 cases). In these figures, FIGS. (a1) and (b1) illustrate the behaviors of the bolus at a concentration (concentration of a thickness adjusting food product in a water solution) of C=1%, FIGS. (a2) and (b2) illustrate the behaviors of the bolus at a concentration of C=2% and FIGS. (a3) and (b3) illustrate the behaviors of the bolus at a concentration of C=3%.

When the accidental swallowing rate or the like can be measured, evaluation or diagnosis of the thickness adjusting food product can be performed. Like the thickness adjusting food product, an object with rheologic properties of the non-Newtonian fluid can be also analyzed by the three-dimensional swallowing simulator. Here, the rheologic properties and the surface tension for water solutions at concentrations of 1.0, 1.5, 2.0, 3.0, and 3.5% (% by weight) regarding the thickness adjusting food product (Toro make (which is registered trademark of Meiji Co., Ltd.) SP (made by Meiji Co., Ltd.)) were measured so as to perform analysis with these physical property values.

(Interaction Analysis)

Figure 22A:
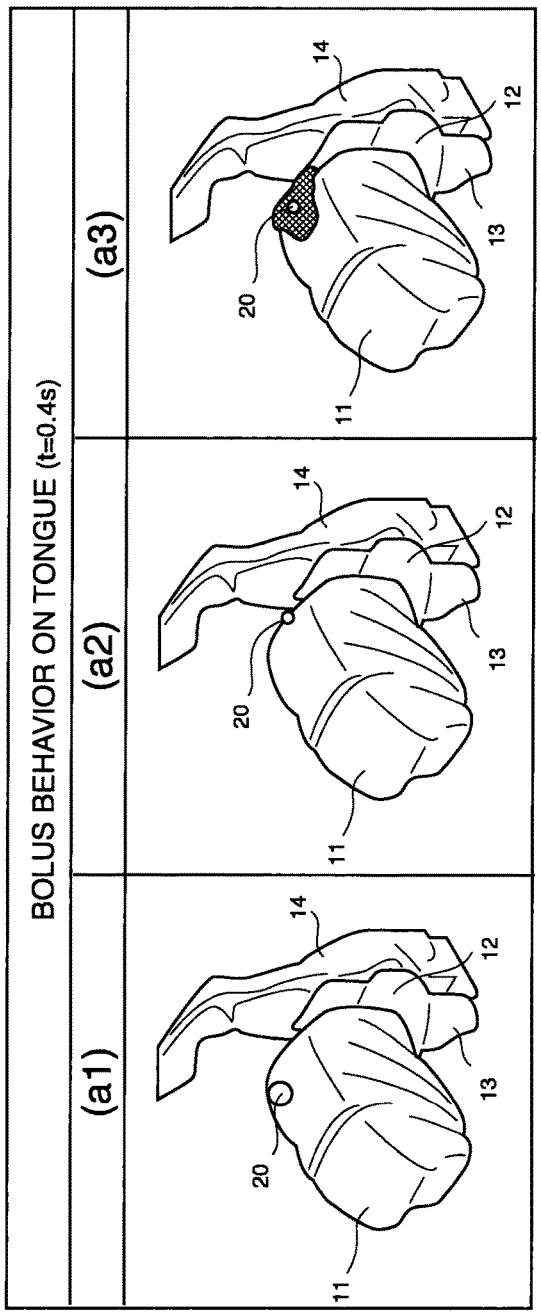
FIG. 22A is a drawing illustrating a behavior of a solid (8 mm sphere) alone, a behavior of the solid (4 mm sphere) alone, and a behavior when a solid (4 mm sphere) and the water are coupled on the tongue 11 at t=0.4 sec in exemplary interaction analysis of solid and fluid.
Figure 22B:
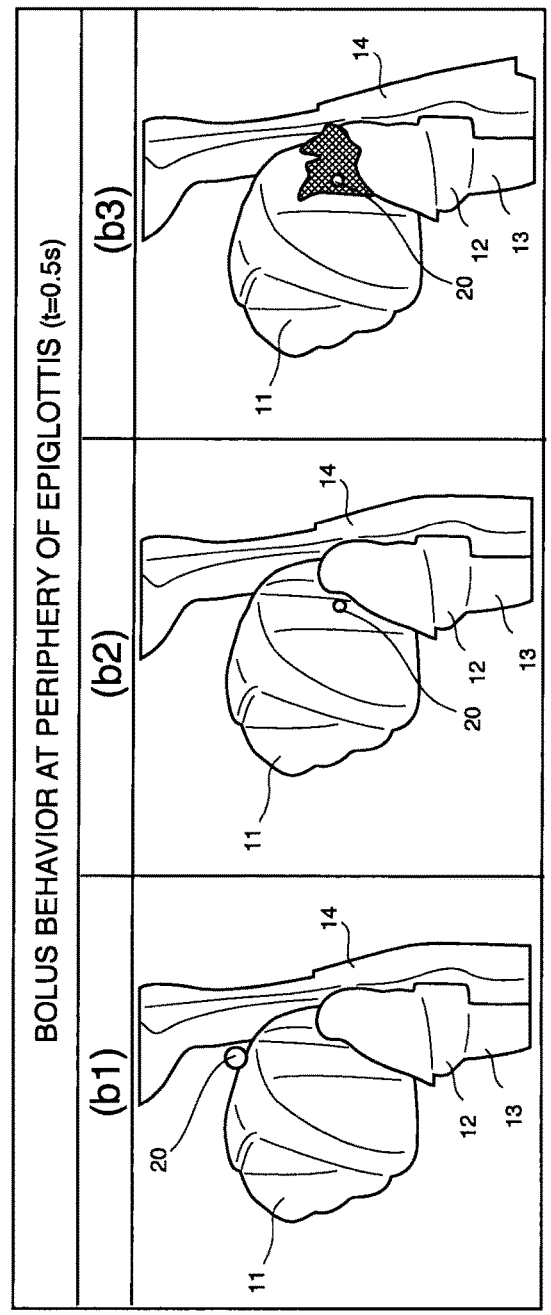
FIG. 22B is a drawing illustrating a behavior of the solid (8 mm sphere) alone, a behavior of the solid (4 mm sphere) alone, and a behavior when the solid (4 mm sphere) and the water are coupled at the periphery of the epiglottis 12a at t=0.5 sec in exemplary interaction analysis of solid and fluid.

FIGS. 22A and 22B illustrate the exemplary interaction analysis of solid and fluid (water). In FIG. 22A, FIGS. (a1) to (a3) illustrate behaviors of the bolus on the tongue 11 at t=0.4 sec (the same time), and in FIG. 22B, FIGS. (b1) to (b3) illustrate behaviors of the bolus at the periphery of the epiglottis 12a at t=0.5 sec (the same time). In these figures, FIGS. (a1) and (b1) illustrate the behavior of the solid (8 mm sphere) alone, FIGS. (a2) and (b2) illustrate the behavior of the solid (4 mm sphere) alone, and FIGS. (a3) and (b3) illustrate the behavior when the solid (4 mm sphere) and the water are coupled.

It is possible to inject the solid and the fluid into the simulator so as to perform an interaction analysis similarly to the two-dimensional simulator. Here, calculation when solid was the 8-mm sphere, calculation when solid was the 4-mm sphere, and interaction calculation when solid and fluid were the 4-mm sphere-water were performed. The density of the hard sphere was set to 11.00 kg/m$^3$, and the friction coefficient between the throat wall surface and the hard sphere was set to 0.

As seen in FIG. 22B (b1), the solid sphere of 8 mm was excessively large, and thus was not able to be transported from the tongue 11 to the pharynx 14 side. The actual human body might swallow the solid sphere in a forcible manner. However, it is considered that an object in a size of approximately 8 mm cannot be smoothly transported according to the structure within the oral cavity 17. Additionally, it was confirmed that the 4-mm sphere was able to be transported with no problem as seen in FIG. 22B (b2) and that the interaction calculation with water was able to be performed with no problem as seen in FIG. 22B (b3). Also in the interaction analysis of the solid and the fluid, the physical properties of the solid and the fluid was able to be set as numerical values.

Figure 23:
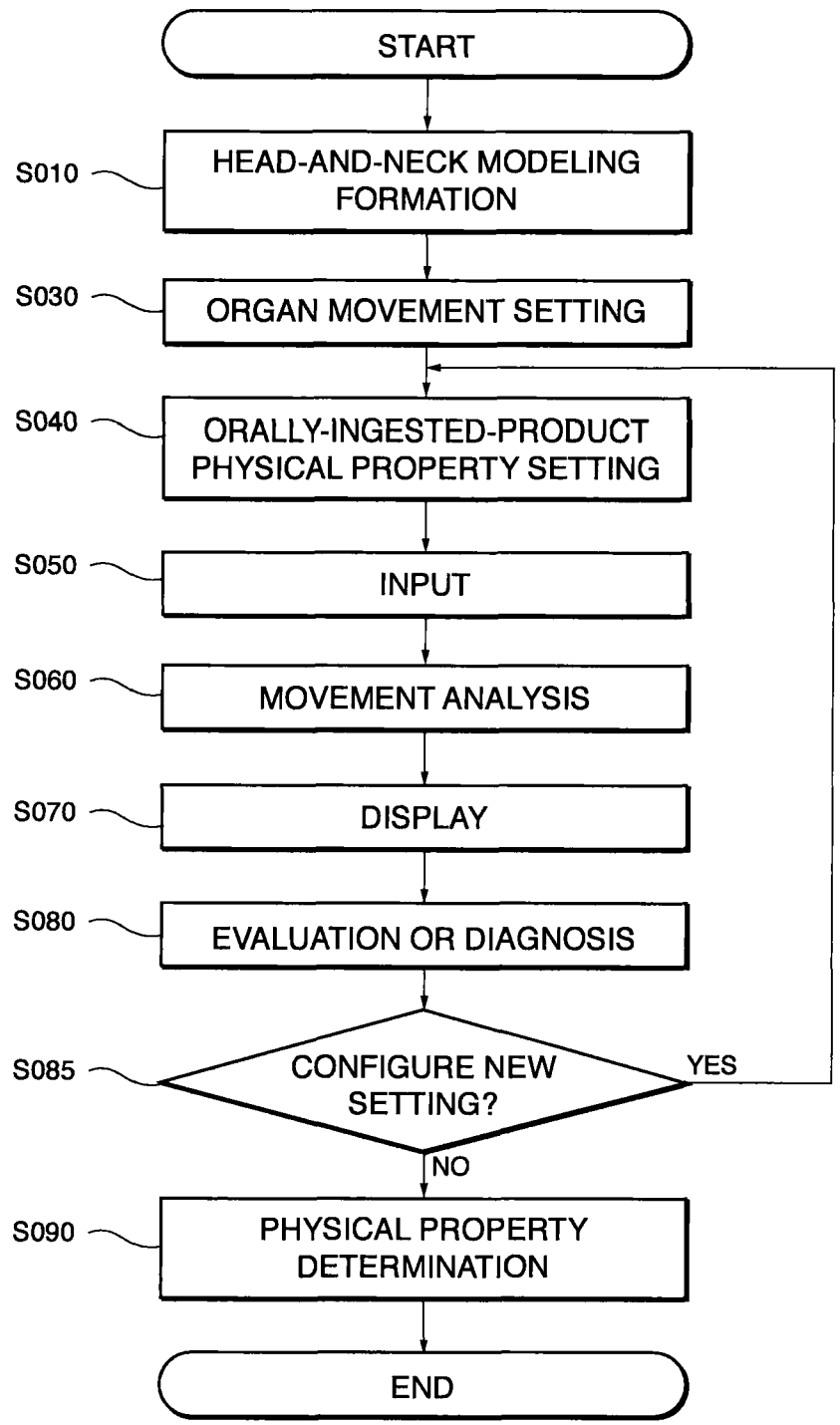
FIG. 23 is a drawing illustrating an exemplary processing flow of a swallowing simulation method according to Embodiment 1.

FIG. 23 illustrates an exemplary processing flow of a swallowing simulation method according to Embodiment 1. Firstly, the dynamic three-dimensional model of the head-and-neck 10a including the head-and-neck organs is formed (S010: a head-and-neck modeling step). Subsequently, the movement of each of the head-and-neck organs are set in the model of the head-and-neck 10a (S030: an organ-movement setting step). Subsequently, an orally-ingested product as an analysis target and physical properties of the orally-ingested product (types of the physical properties and physical property values) are set (S040: an orally-ingested-product physical-property setting step). The contents of these settings can be arbitrarily selected depending on the situation. The contents of the settings are stored in the storage unit 83. Subsequently, the pseudo-orally-ingested product 20 obtained by modeling the orally-ingested product is input to the oral cavity (S050: an input step). The input is performed such that, for example, the evaluator or the person to diagnose drags and drops a cursor to the oral cavity using a computer mouse. Subsequently, the movement of each of the head-and-neck organs in the model of the head-and-neck 10a and the behavior related to swallowing of the pseudo-orally-ingested product 20 are analyzed in the three-dimensional space using the particle method (S060: a movement analyzing step). For example, an MPS method can be used. Subsequently, the analysis result obtained in the movement analyzing step (S060) is displayed (S070: a display step).

Subsequently, based on the analysis result of the behavior of the pseudo-orally-ingested product 20 during swallowed, easiness of eating and/or easiness of drinking of the orally-ingested product is evaluated or diagnosed (S080: an evaluation/diagnosis step, for one process, an evaluation step or a diagnosis step). The evaluation or diagnosis is made by the evaluator or the person to diagnose viewing the movement screen on the display unit 82. "Good", "poor", a rank, a score, or the like is input to a cell in an evaluation table or a diagnosis table displayed on the display unit 82, for example. After the evaluation or diagnosis is made, the process returns to the orally-ingested-product physical-property setting step (S040), the physical property values of the orally-ingested product are changed and set, and then the subsequent process up to the evaluation/diagnosis step is repeatedly performed. The physical property value to be changed can be arbitrarily selected by determination of the evaluator or the person to diagnose. Note that if proper physical properties are found in the first time, the subsequent setting and evaluation or diagnosis may be omitted. Subsequently, the physical properties of the orally-ingested product regarded as appropriate in the evaluation/diagnosis step (S080) are determined (S090: a physical property determination step). Here, the range of the appropriate physical property may be indicated, the appropriate physical property may be ranked, or the optimal value may be selected.

Evaluation items or diagnosis items are, for example, as follows.

(a) Whether risks of the swallowing, the accidental swallowing, accidental ingestion, and choking (the orally-ingested product sticks to, for example, the palate wall and difficult to be peeled off, obstructs the throat or the gullet 18, or enters the larynx 12) exists or not (b) How long is the swallowing period? Is the threshold exceeded?

(c) How much are stress and shear stress applied to the pharynx wall? Is the threshold exceeded?

(d) Based on (a) to (c), considering correlativity with a sensory evaluation or a sensory diagnosis (tasty, exhilarating feeling, or the like) whose data has been obtained separately, easiness of drinking, easiness of eating, difficulty of drinking, and difficulty of eating are evaluated or diagnosed comprehensively The sensory evaluation or the sensory diagnosis is saved in the evaluation/diagnosis-result recording unit 83B in association with the orally-ingested product and the physical properties of the orally-ingested product. This sensory evaluation or sensory diagnosis of the orally-ingested product is read out to consider, for example, the correlativity with the swallowing period, the shear stress, or the like.

As described above, with this embodiment, for the model of the head-and-neck 10a, the organ properties, the movements of the head-and-neck organs, and the physical properties of the orally-ingested product are set to analyze the behavior of the orally-ingested product using the particle method. This allows providing the swallowing simulation apparatus and the swallowing simulation method that facilitate approximately reproducing the actual phenomenon of swallowing, that is, the behaviors of the head-and-neck organs and the orally-ingested product. Additionally, quantifying the physical properties and the physical quantities of the bolus using the swallowing simulator for analysis allows providing the swallowing simulation apparatus and the swallowing simulation method that can accurately express the behaviors of the head-and-neck organs and the orally-ingested product during swallowed and that can quantify the physical quantities related to the behavior and the physical properties of the orally-ingested product.

Second Embodiment

In Embodiment 1, an exemplary swallowing evaluation or swallowing diagnosis made by inputting the orally-ingested product and viewing the moving image by the evaluator or the person to diagnose is described. In Embodiment 2, an example where the swallowing simulation apparatus automatically inputs the orally-ingested product or similar product based on the setting and automatically performs the swallowing evaluation or the swallowing diagnosis is described. The following mainly describes the points different from Embodiment 1 (similarly, in the following embodiments, the points different from the Embodiments described there before are mainly described).

Figure 24:
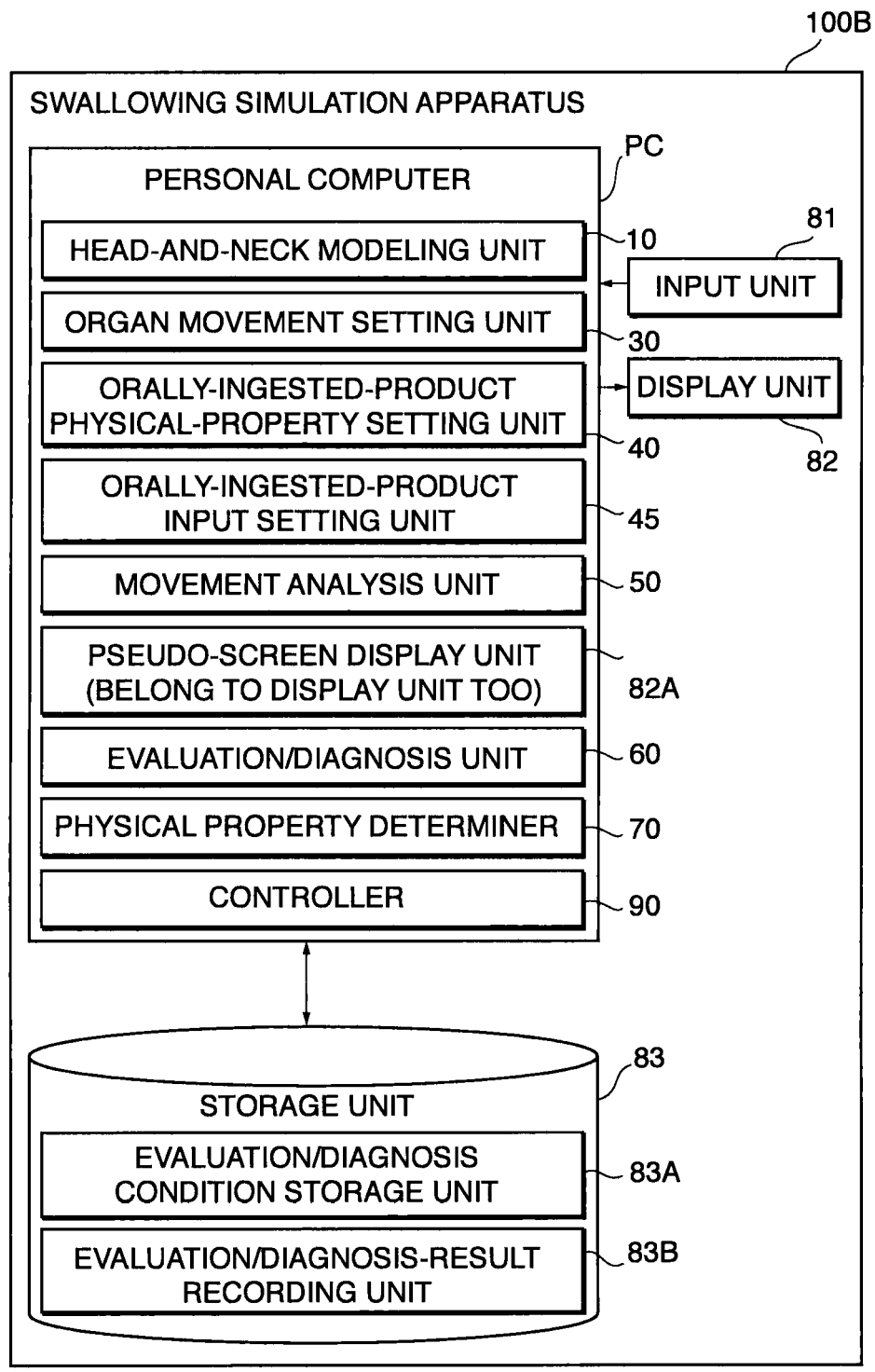
FIG. 24 is a drawing illustrating an exemplary configuration of a swallowing simulation apparatus according to Embodiment 2.

FIG. 24 illustrates an exemplary configuration of a swallowing simulation apparatus 100B according to Embodiment 2. A pseudo-screen display unit 82A and an orally-ingested-product input setting unit 45 are added in the personal computer (PC) compared with Embodiment 1 (see FIG. 2). The pseudo-screen display unit 82A displays the analysis result of the behavior of the pseudo-orally-ingested product during swallowed on a virtual movement screen. The orally-ingested-product input setting unit 45 sets an input condition of the pseudo-orally-ingested product. Furthermore, an evaluation/diagnosis unit 60 (for one process, an evaluation unit or a diagnosis unit) is added. The evaluation/diagnosis unit 60 refers to the evaluation condition or the diagnosis condition stored in an evaluation/diagnosis condition storage unit 83A to automatically evaluate or diagnose easiness of eating and/or easiness of drinking of the orally-ingested product. Other configurations are similar to Embodiment 1.

Figure 25:
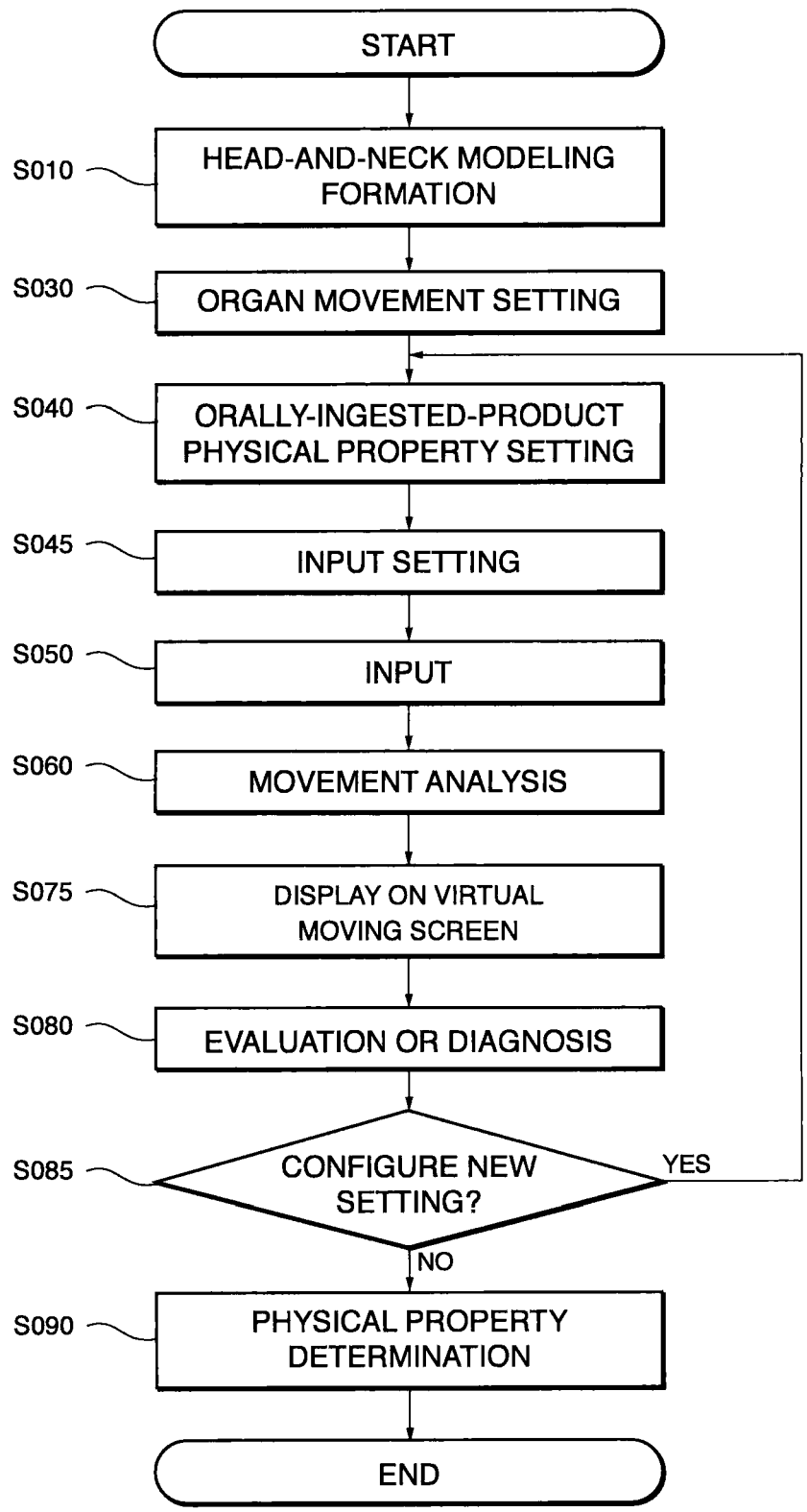
FIG. 25 is a drawing illustrating an exemplary processing flow of a swallowing simulation method according to Embodiment 2.

FIG. 25 illustrates an exemplary processing flow of a swallowing simulation method. An orally-ingested-product input setting step (S045) is added before the input step (S050) compared with Embodiment 1 (see FIG. 23). The orally-ingested-product input setting step (S045) sets the input condition of the orally-ingested-product. The display step (S070) for displaying the movement screen on the display unit 82 is replaced by the step for displaying the virtual movement screen on the pseudo-screen display unit 82A (S075). In the evaluation/diagnosis step (S080), the evaluation/diagnosis unit 60 makes an automatic evaluation or diagnosis. Other steps are similar to Embodiment 1.

In Embodiment 2, an injection position and injection timing of the orally-ingested product are preset to the orally-ingested-product input setting unit 45 (S045: the orally-ingested-product input setting step). The injection position of the pseudo-orally-ingested product in the oral cavity is, for example, set near the teeth in the oral cavity (for example, within twice the length of the pseudo-orally-ingested product). Next, the pseudo-orally-ingested product 20 is injected into the oral cavity in accordance with the setting conditions (position and timing) (S050: an orally-ingested-product input step). For automatic evaluation or automatic diagnosis, the evaluation condition or the diagnosis condition is preliminary stored in the evaluation/diagnosis condition storage unit 83A. The behaviors of the model of the head-and-neck 10a and the pseudo-orally-ingested product 20 as the analysis results of the simulations are displayed on the virtual movement screen of the pseudo-screen display unit 82A in the personal computer PC. The display of the pseudo-screen display unit 82A is collated with the evaluation condition or the diagnosis condition of the evaluation/diagnosis condition storage unit 83A by the evaluation/diagnosis unit 60. Thus, evaluation or diagnosis is performed.

Evaluation items or diagnosis items are, for example, as follows.

(a) Whether risks of the swallowing, the accidental swallowing, accidental ingestion, and choking (the orally-ingested product sticks to, for example, the palate wall and difficult to be peeled off, obstructs the throat and the gullet 18, or enters the larynx 12) exists or not.

(b) How long is the swallowing period? Is the threshold exceeded?

(c) How much are stress and shear stress applied to the pharynx wall? Is the threshold exceeded?

(d) Based on (a) to (c), considering correlativity with a sensory evaluation or a sensory diagnosis (tasty, exhilarating feeling, or the like) whose data has been obtained separately, easiness of drinking, easiness of eating, difficulty of drinking, and difficulty of eating are evaluated or diagnosed comprehensively.

(a) to (c) and the sensory evaluations or the sensory diagnoses are preliminary converted into values, respectively. Then, the values are multiplied by a weighting factor. The total is automatically and comprehensively evaluated or diagnosed. (c) and/or (d) may be omitted.

Other configurations and processing flows are similar to Embodiment 1. Similarly to Embodiment 1, this allows providing the swallowing simulation apparatus and the swallowing simulation method that facilitate reproducing the actual phenomenon of swallowing.

Additionally, even the case where one of the input and the evaluation or the diagnosis is performed by the human and the other is performed by the computer is similarly applicable and achieves similar effects.

Third Embodiment

While in the above-described embodiments, an example of evaluation or diagnosis by the evaluator or the person to diagnose and an example of automatic evaluation or automatic diagnosis by the swallowing simulation apparatus are described, the evaluation result or the diagnosis result (partial or overall result) by the swallowing simulation apparatus may be displayed, and an evaluation or a diagnosis may be requested to the evaluator or the person to diagnose. In this case, regarding a processing flow, in the evaluation/diagnosis step (S080) of Embodiment 2, the evaluation result or the diagnosis result (partial or overall result) by the swallowing simulation apparatus is displayed on the display unit 82 together with the evaluation table or the diagnosis table. With reference to the evaluation result or the diagnosis result from the swallowing simulation apparatus, the evaluator or the person to diagnose inputs his/her evaluation result or diagnosis result to the evaluation table or the diagnosis table. The orally-ingested-product input step (S050) may be manually input by the human or may be automatically input. Other apparatus configurations and processing flows are similar to Embodiment 2. Similarly to Embodiment 2, this allows providing the swallowing simulation apparatus and the swallowing simulation method that facilitate reproducing the actual phenomenon of swallowing.

Fourth Embodiment

In the above-described embodiments, the physical property of the orally-ingested product automatically determined as appropriate by the physical property determiner 70 is described as an example. In this embodiment, an exemplary determination made by the human is described. In the apparatus configuration of this embodiment, typically, the physical property determiner 70 in FIG. 2 of Embodiment 1 is removed. FIG. 23 can be used as an exemplary processing flow. The physical property determiner 70 may be present. In this case, the physical property determiner 70 is not used or a determination result by the physical property determiner 70 is shown to a decider (for example, the evaluator or the person to diagnose) as a reference. The physical property of the orally-ingested product is determined as appropriate by the human. However, there is no difference in that the determination is made based on the evaluation result or the diagnosis result. Although, the determination is possibly slightly changed in an intellectual process, almost similar results are predicted. Other apparatus configurations and processing flows are similar to Embodiment 1. Similarly to Embodiment 1, this allows providing the swallowing simulation apparatus and the swallowing simulation method that facilitate reproducing the actual phenomenon of swallowing. When a determination is made by the human, this applies to Embodiment 2 and Embodiment 3 similarly to Embodiment 1.

Fifth Embodiment (Development of Orally-Ingested Product)

Next, a description will be given of examples where simulations are performed while a physical property value is changed, and the simulation results are led to development of an orally-ingested product.

Figure 26:
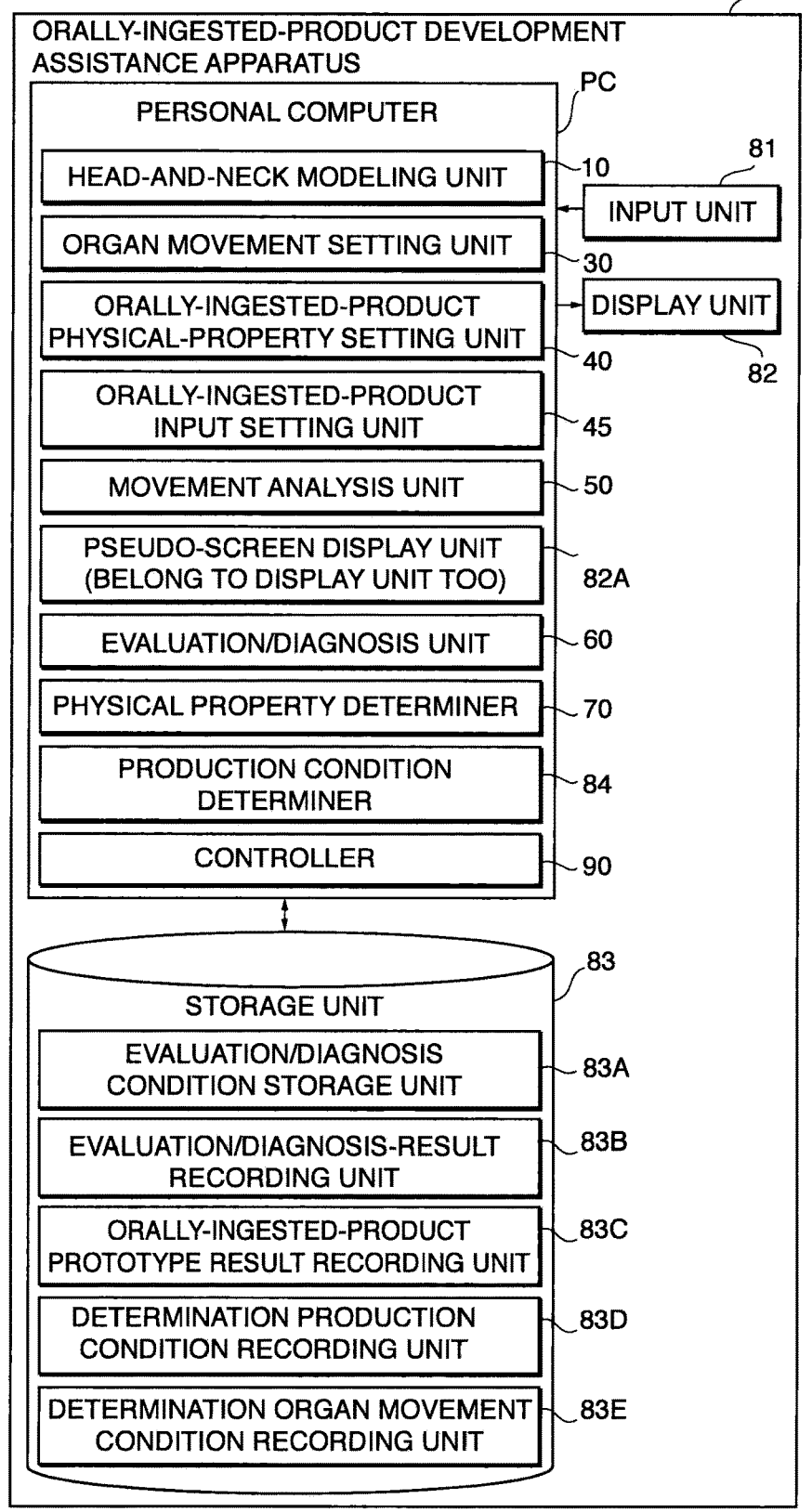
FIG. 26 is a drawing illustrating an exemplary configuration of an orally-ingested-product development assistance apparatus according to Embodiment 5.

FIG. 26 illustrates an exemplary configuration of an orally-ingested-product development assistance apparatus 200A. An orally-ingested-product prototype result recording unit 83C, a determination production condition recording unit 83D, and a production condition determiner 84 are added to the swallowing simulation apparatus 100A in FIG. 2. The orally-ingested-product prototype result recording unit 83C belongs to the storage unit 83. The orally-ingested-product prototype result recording unit 83C records a result (including the physical property values) of an experimental production performed under an appropriately-set production condition that allows the prototype to have a physical property determined as appropriate by the physical property determiner 70. The production condition determiner 84 is disposed in the personal computer PC. The production condition determiner 84 determines a production condition that sets a physical property of the orally-ingested product to the physical property determined as appropriate by the physical property determiner 70 based on the prototype result recorded in the orally-ingested-product prototype result recording unit 83C. The determined production condition is recorded in the determination production condition recording unit 83D of the storage unit 83. This clarifies the production condition that sets a physical property to the physical property determined as appropriate by the physical property determiner 70, thus reliably developing an orally-ingested product with easy-to-eat and/or easy-to-drink physical property.

Figure 27:
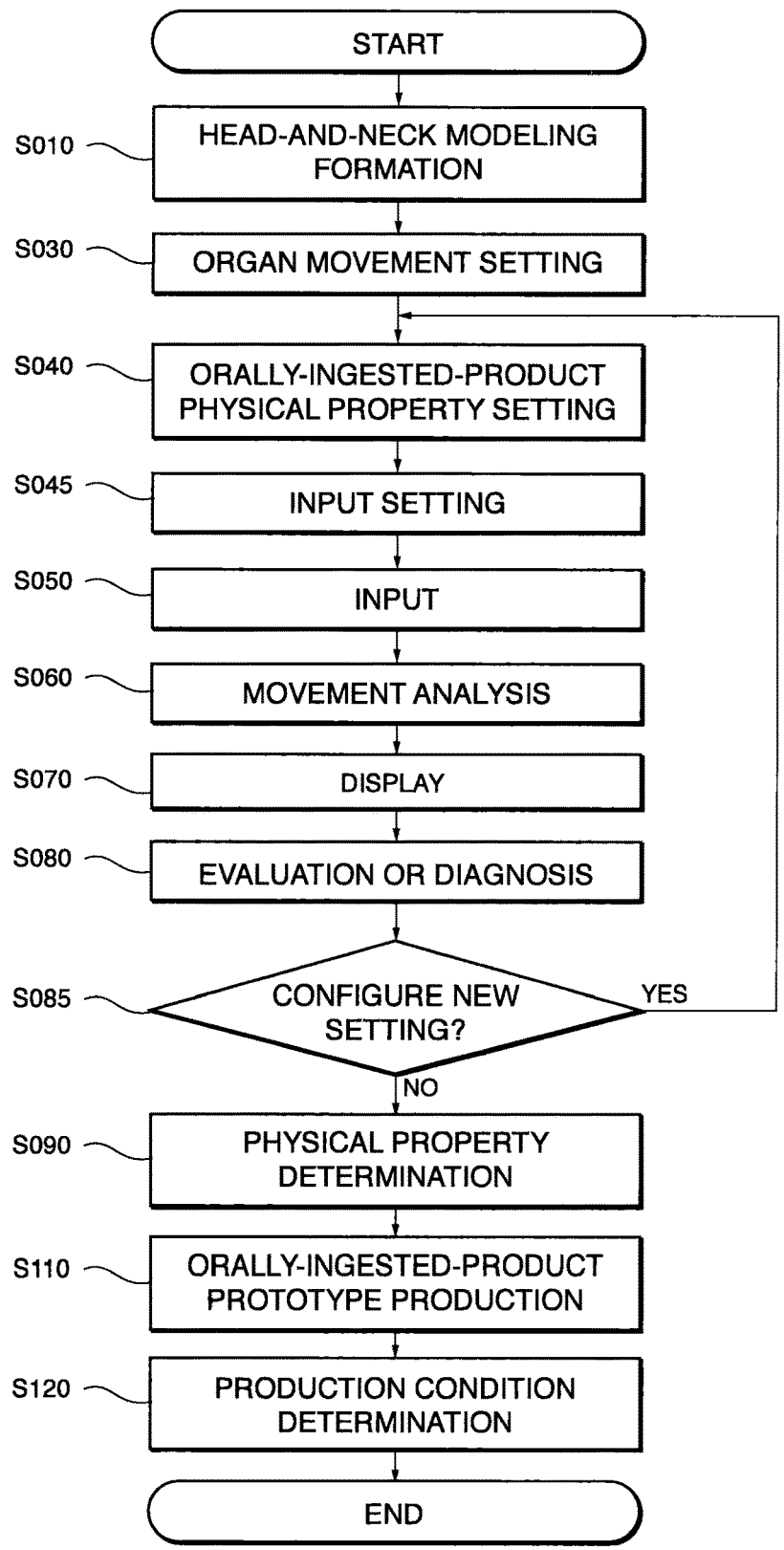
FIG. 27 is a drawing illustrating an exemplary processing flow of an orally-ingested-product development method according to Embodiment 5.

FIG. 27 illustrates an exemplary processing flow of an orally-ingested-product development method. After the exemplary processing flow of the swallowing simulation method in FIG. 23, an orally-ingested-product prototype production step (S110) and a production condition determination step (S120) are added. The orally-ingested-product prototype production step (S110) produces a prototype under an appropriately-set production condition so as to allow the prototype to have the physical property determined as appropriate in the physical property determination step (S090). A prototype of, for example, confectionery is produced while combination conditions of raw materials (such as a combination ratio and a stir), baking conditions (such as a temperature, a period, and atmosphere), cooling conditions (such as a temperature, a period, and atmosphere), dimensions, and the like are appropriately set. A result of the experimental production where the obtained physical property is associated with the production condition is recorded in the orally-ingested-product prototype result recording unit 83C of the storage unit 83.

The production condition determination step (S120) determines a production condition that sets the physical property of the orally-ingested product to the physical property determined as appropriate in the physical property determination step (S090) based on the experimental production result in the orally-ingested-product prototype production step (S110), that is, the experimental production result recorded in the orally-ingested-product prototype result recording unit 83C. In the orally-ingested-product prototype production step (S110), for example, if a result where the physical property determined as appropriate has been obtained with a combination ratio A of raw materials and a baking temperature B, the combination ratio A of raw materials and the baking temperature B are determined as production conditions that sets the physical property to the physical property determined as appropriate. The production condition may be one point or may specify a range. The production condition may determine the optimum value or may classify an appropriate range into ranks. This determination may be made by a human, or may by automatically made by the production condition determiner 84 based on the prototype result recorded in the orally-ingested-product prototype result recording unit 83C. The result determined in the production condition determination step (S120) is, for example, recorded in the determination production condition recording unit 83D of the storage unit 83. When the determination is made by a human, the result may be recorded in a notebook.

(Orally-Ingested-Product Production Method)

Figure 28:
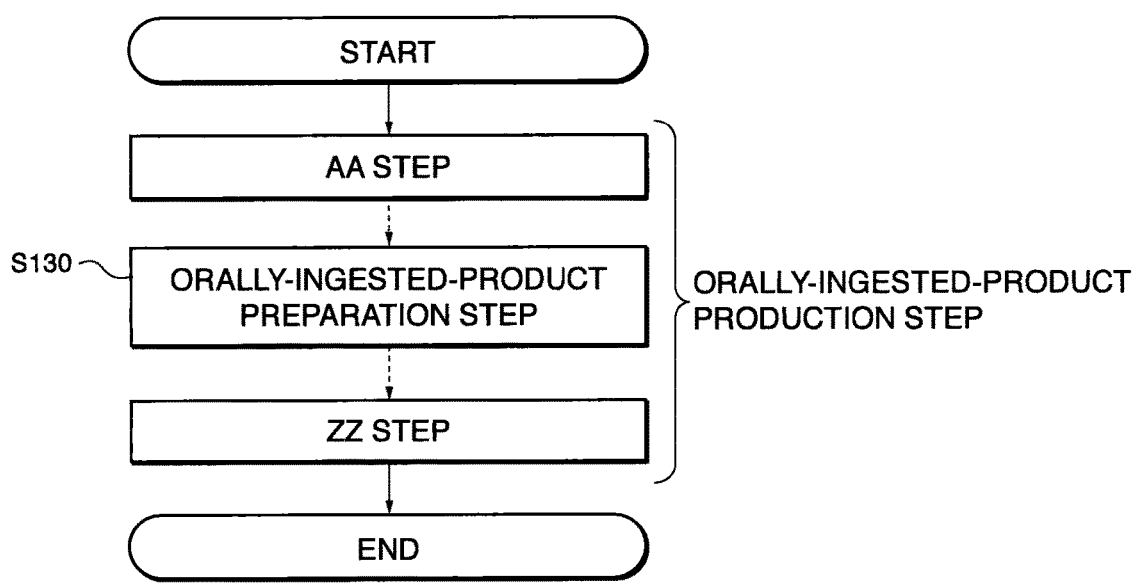
FIG. 28 is a drawing illustrating an exemplary processing flow of an orally-ingested-product production method according to Embodiment 5.

FIG. 28 illustrates an exemplary processing flow of an orally-ingested-product production method. An orally-ingested-product production step includes an orally-ingested-product preparation step (S130). Assume that the first step is an AA step and the last step is a ZZ step. The orally-ingested-product preparation step (S130) prepares an orally-ingested product using the production condition determined as the production condition that sets the physical property determined as appropriate in the physical property determination step (S090) in the production condition determination step (S120) of the orally-ingested-product development method in FIG. 27. The orally-ingested-product preparation step (S130) may be performed in any step in the production steps. For example, in production of confectionery, the orally-ingested product can be prepared in a raw material combination step, a baking step, or the like. Two or more steps may be combined for the preparation. Then, in the case where the production condition in this orally-ingested-product preparation step (S130) is determined in the production condition determination step (S120), this corresponds to the embodiment. The result determined in the production condition determination step (S120) is recorded, for example, in the determination production condition recording unit 83D of the storage unit 83. This reliably produces a development orally-ingested product with easy-to-eat and/or easy-to-drink physical property.

As described above, with this embodiment, for the model of the head-and-neck 10a, the organ properties, the movements of the head-and-neck organs, and the physical properties of the orally-ingested product are set to analyze the behavior of the orally-ingested product using the particle method. This allows analyzing the swallowing phenomenon using the swallowing simulation method that facilitates reproducing the actual phenomenon of swallowing so as to develop an easy-to-eat or easy-to-drink orally-ingested product.

Sixth Embodiment (Dietary Education Apparatus and Dietary Education Method)

This embodiment describes an example of applying the swallowing simulator according to the present invention to dietary education.

Figure 29:
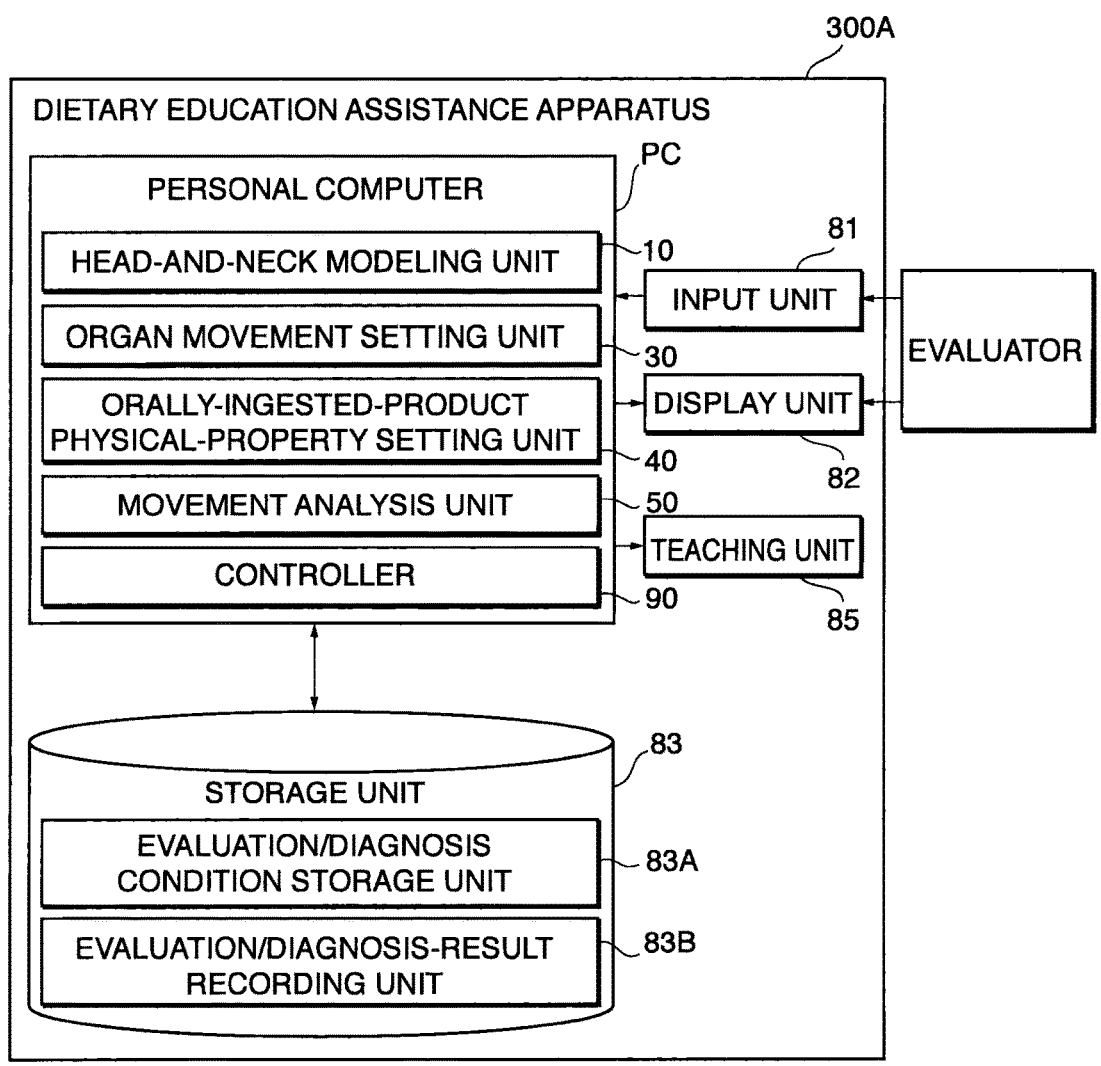
FIG. 29 is a drawing illustrating an exemplary configuration of a dietary education assistance apparatus according to Embodiment 6.

FIG. 29 illustrates an exemplary configuration of a dietary education assistance apparatus 300A according to this embodiment. Compared with the simulation apparatus 100A in Embodiment 1 (see FIG. 2), a teaching unit 85 is added while the physical property determiner 70 is removed. The teaching unit 85 teaches a behavior of the pseudo-orally-ingested product 20 during swallowed displayed on the movement screen by the display unit 82 associating with the evaluation result or the diagnosis result of the orally-ingested product recorded in the evaluation/diagnosis-result recording unit 83B. In this embodiment, the teaching contents are based on the evaluation result or the diagnosis result of the orally-ingested product recorded in the evaluation/diagnosis-result recording unit 83B. The explanation contents are preliminary created and recorded. The teaching unit 85 may automatically create the explanation contents based on the evaluation result or the diagnosis result. However, it is preferred that the explanation contents be edited and supplemented for easier understanding by an educator. Additionally, in this embodiment, the physical property determiner 70 is removed. However, the physical property determiner 70 may be included so that the educator explains determination of a physical property. The teaching unit 85 stores the explanation contents (teaching contents). The teaching unit 85 also displays analysis results of movement of each head-and-neck organ and the behavior of the pseudo-orally-ingested product 20 while being swallowed analyzed by the movement analysis unit 50 on the movement screen of the display unit 82. The explanation contents are phonetically output to, for example, a speaker of the display unit 82.

Figure 30:
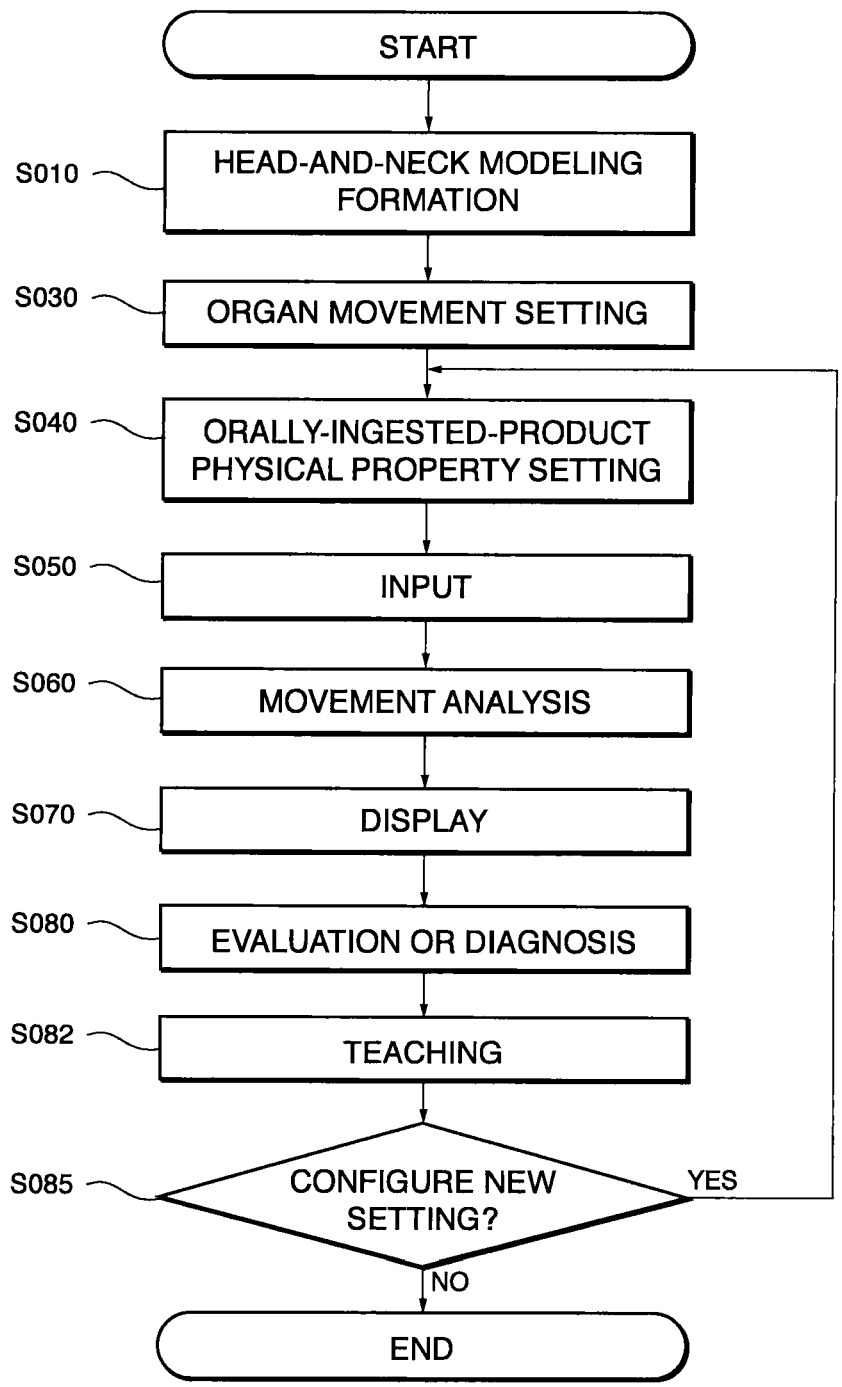
FIG. 30 is a drawing illustrating an exemplary processing flow of a dietary education method according to Embodiment 6.

FIG. 30 illustrates an exemplary processing flow of a dietary education method according to this embodiment. Compared with the simulation method in Embodiment 1 (see FIG. 23), the teaching step (S082) is added after the evaluation/diagnosis step (S080), and the physical property determination step (S090) is removed. The teaching step (S082) teaches a behavior of the pseudo-orally-ingested product while being swallowed displayed on the movement screen in the display step (S070) associating with the evaluation result or the diagnosis result of the orally-ingested product evaluated or diagnosed in the evaluation/diagnosis step (S080). In this embodiment, the physical property determiner 70 and the physical property determination step (S090) are removed. However, the physical property determiner 70 and the physical property determination step (S090) may be included so that the educator explains determination of a physical property. Accordingly, the swallowing phenomenon is displayed using the swallowing simulation method that facilitates reproducing actual phenomenon of swallowing. Accordingly, easiness of eating and easiness of drinking of the orally-ingested product are easily understood, effective in dietary education.

Seventh Embodiment (Diagnosis Assistance)

In this embodiment, an exemplary application of the swallowing simulator according to the present invention to assistance for swallowing diagnosis is described.

Figure 31:
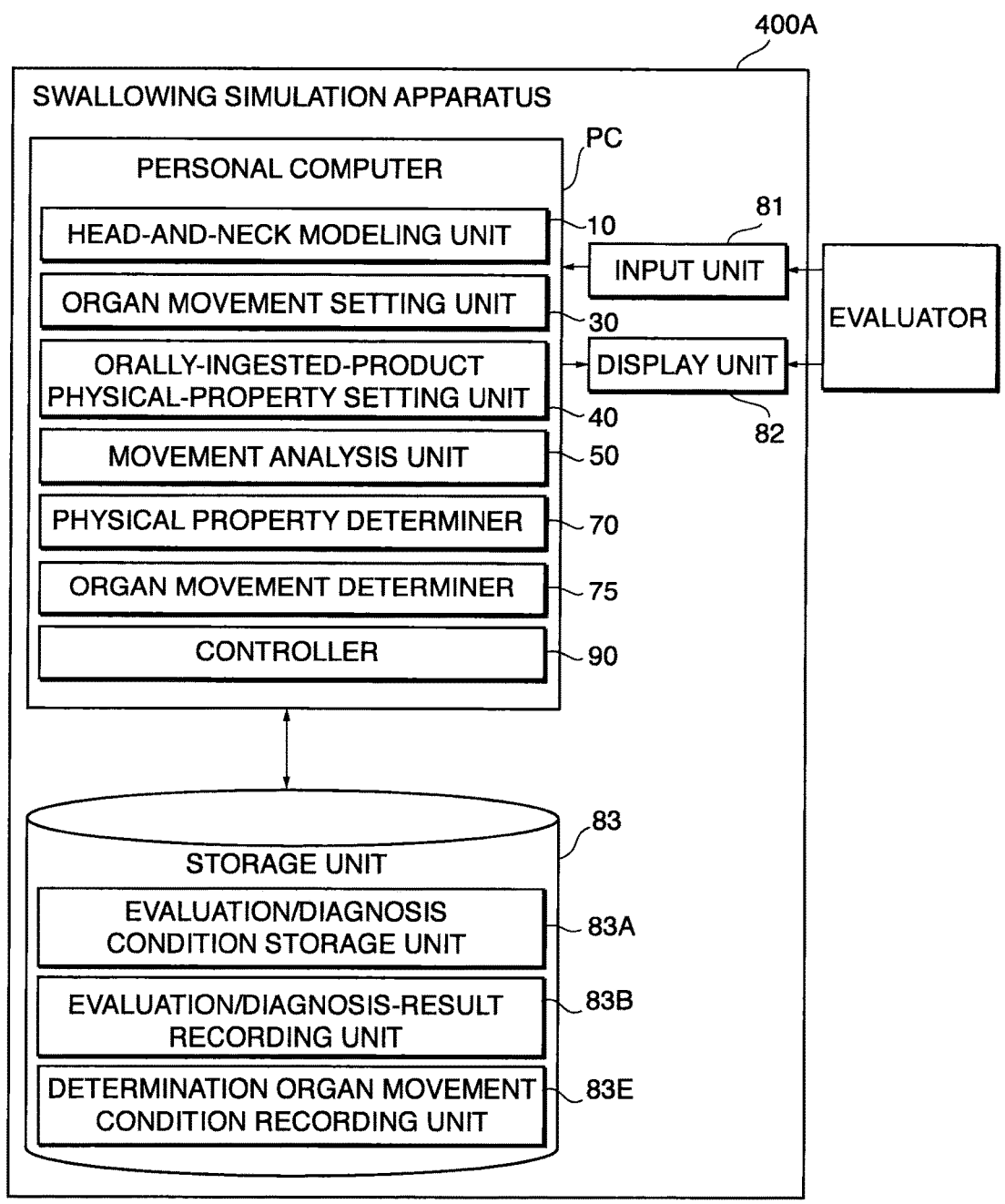
FIG. 31 is a drawing describing an exemplary configuration of a swallowing simulation apparatus according to Embodiment 7.

FIG. 31 illustrates a configuration of a swallowing simulation apparatus 400A according to this embodiment. An organ movement determiner 75 and a determination organ movement condition recording unit 83E are added to the swallowing simulation apparatus 100A according to Embodiment 1 (see FIG. 2). Additionally, the organ movement setting unit 30 is more frequently used. The organ movement setting unit 30 sets movement properties of each of the head-and-neck organs related to the swallowing movement. However, for example, a reaction velocity, timing of contract and relax, contract distance, and elasticity (flexibility) of the genioglossus 11f and other muscles related to the swallowing, or similar property are set as movement parameters. Then, the organ movement determiner 75 determines an organ movement parameter of each of the head-and-neck organs from simulation results, that is, the analysis results analyzed by the movement analysis unit 50. A slow traveling-wave motion of the tongue, for example, takes time to reach the swallowing. A slow reaction of the epiglottis 12a possibly causes the orally-ingested product to enter the trachea 13 through the larynx 12, resulting in accidental swallowing. This allows obtaining the organ movement parameters for each of the head-and-neck organs finely fitting a behavior or a symptom of each head-and-neck organ of a patient or a person to be diagnosed for checkup. The determination organ movement condition recording unit 83E records the organ movement parameter obtained by the organ movement determiner 75.

Then, from the results of the swallowing simulation based on the model of the head-and-neck 10a, for example, whether muscles of the patient or the person subject to checkup are functionally deteriorated in the swallowing or not is determined, useful in treatment. Since the organ function is put more importance than the physical property of the orally-ingested product in diagnosis, a loop process may not be performed on the physical property and the physical property may be fixed. Such simulation apparatus can also be incorporated into the swallowing diagnosis assistance apparatus. The swallowing diagnosis assistance apparatus with medical treatment diagnosis result database that records diagnosis results on the patient or the person subject to checkup is configured, for example. The diagnosis result is compared with the evaluation/diagnosis result recorded in the evaluation/diagnosis-result recording unit 83B of the swallowing simulation apparatus 400A. This allows finding a functionally-deteriorated portion of each head-and-neck organ, thus ensuring prompt diagnosis.

Figure 32:
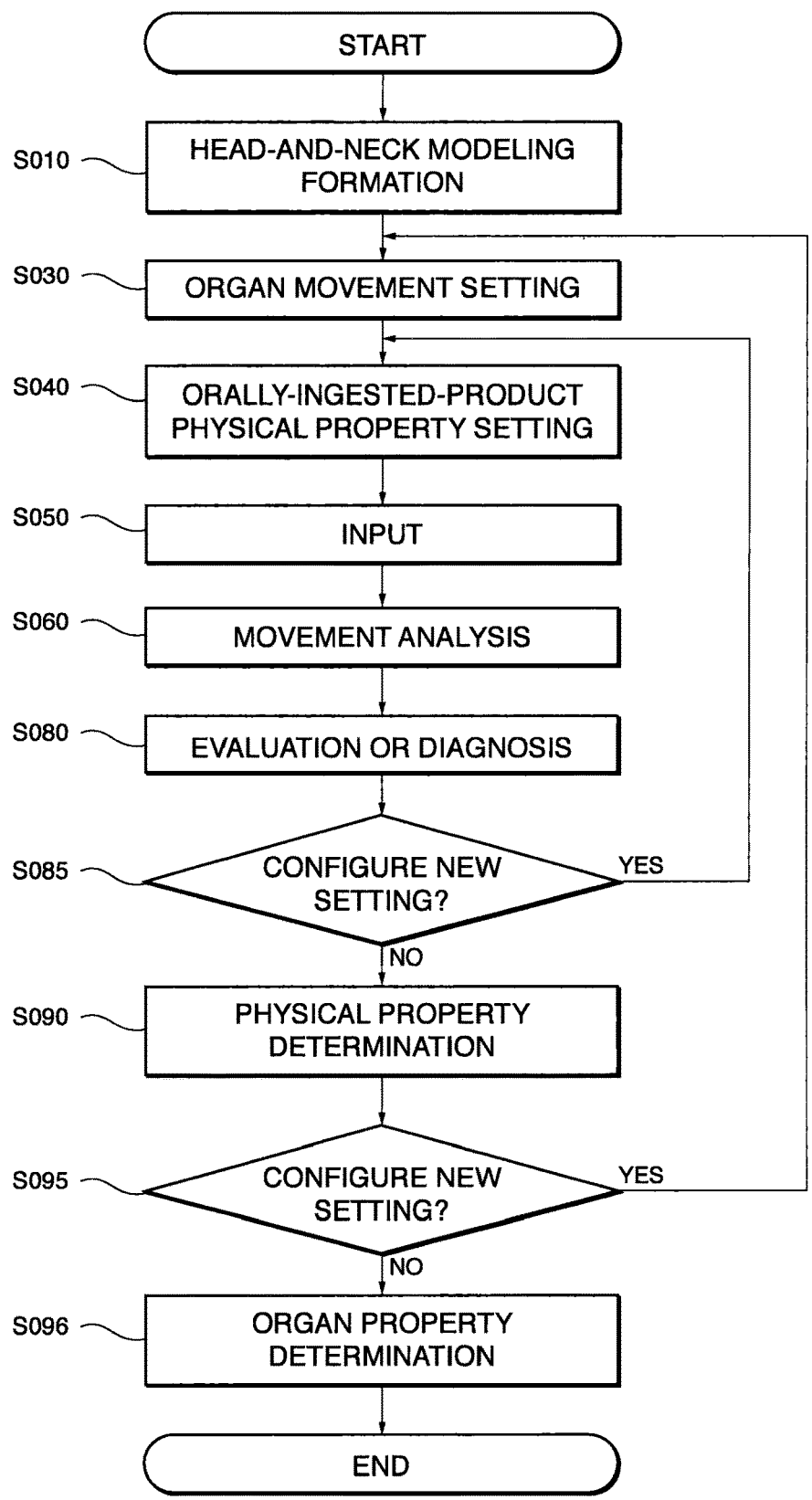
FIG. 32 is a drawing describing an exemplary processing flow of diagnosis assistance according to Embodiment 7.

FIG. 32 illustrates an exemplary processing flow of the simulation method according to this embodiment. A loop that changes the organ movement parameter is added to the swallowing simulation method according to Embodiment 1 (see FIG. 23). That is, after the loop process where the parameter of the physical property is changed, a loop process that changes the organ movement parameter is performed. Here, the physical property determination and the organ property determination do not find a physical property and an organ movement appropriate for swallowing, but are used for looking for the organ movement parameter fitting to the symptom of the patient or the person to be diagnosed for checkup using loops. The processing flows are terminated at the time when simulations are performed with sequentially changed parameters and the physical property or the organ properties fitting to the behavior or the symptom of each head-and-neck organ of the patient or the person to be diagnosed for checkup are found.

It is also possible to predict the parameter after the treatment, continue the simulation, and obtain an improvement effect of treatment.

(Program)

The present invention is also applicable also as a program readable by the computer to make the computer execute the above-described swallowing simulation methods. Additionally, the present invention can be achieved also as a storage medium to store the program. The program may be stored into the controller 90 of the swallowing simulation apparatus for use, may be stored to the built-in or external storage device for use, or may be downloaded from the Internet for use.

The preferred embodiments of the present invention are described above. However, the present invention should not be limited to these embodiments. Various variations are possible without departing from the spirit of the present invention.

For example, while in the above-described embodiments examples of the model of the tongue and the model of the epiglottis have been described, the models are not limited to these examples and various models can be used. For example, the shapes of the respective organs changing with time can be read for each analyzing time so as to simulate a smoother movement. Further the parameters such as the division number and the vibration frequency can be arbitrarily changed in the analysis. Furthermore, these respective organs can be moved while interlocking with the associated muscle. Regarding the development and the production method of the orally-ingested product in Embodiment 5 and the dietary education apparatus and the dietary education method in Embodiment 6, the examples mainly in combination with the simulation apparatus in Embodiment 2 have been described. However, the simulation apparatuses in Embodiment 1, Embodiment 3, and Embodiment 4 may be combined.

Regarding the diagnosis assistance in Embodiment 7, the example mainly in combination with the simulation apparatus in Embodiment 1 has been described. However, the simulation apparatuses in Embodiment 2 to Embodiment 4 may be combined. The exemplary orally-ingested products have been shown up to two. However, the three or more orally-ingested products can be operated together and the behavior can be analyzed. Further, an interaction analysis of solids with mutually different physical property values, for example, chocolate covering peanuts (solid-solid), an interaction analysis of chocolate incorporating liqueur (solid-liquid), and also an interaction analysis of mixed liquid of liquids (oil and vinegar) with mutually different physical property values, for example, dressing (liquid-liquid) are possible. In the case where saliva is added, for example, an analysis can be performed by preliminarily setting the period (a plurality of times) and the amount regarding the addition and importing dissolution of the orally-ingested product by the saliva. Additionally, the number of divisions of the model of the tongue, the dimensions of the overlap portion, the movement amount and the movement period of each portion, or the like can be changed in appropriate ranges.

INDUSTRIAL APPLICABILITY

The present invention is used for analyzing a swallowing condition of an orally-ingested product.

Use of the terms "a," "an," "the" and similar referents used in the context in explanation of the invention (particularly in the context of claims as described below) is to be construed to cover both the singular form and the plural form, unless otherwise indicated herein or clearly contradicted by context. The terms "comprising," "having," "including" and "containing" are to be construed as open-ended terms (more specifically, meaning "including, but not limited to") unless otherwise noted. Recitation of ranges of values herein are merely intended to serve as a shorthand method of referring individually to each separate value falling within the range, unless otherwise indicated herein, and each separate value is incorporated herein as if it were individually recited herein. All methods described herein can be performed in any suitable order unless otherwise indicated herein or otherwise clearly contradicted by context. The use of any and all examples, or exemplary language ("such as") provided herein, is intended merely to better illuminate the invention and does not pose a limitation on the scope of the invention unless otherwise claimed. No language herein should be construed as indicating any non-claimed element as essential to the practice of the invention.

Preferred embodiments of the invention are described herein, including the best mode known to the present inventors for carrying out the present invention. Variations of the preferred embodiments may become apparent to those skilled in the art upon reading the foregoing description. The present inventors expect skilled artisans to employ such variations as appropriate, and the present inventors intend for the invention to be practiced otherwise than as specifically described herein. Accordingly, the invention includes all modifications and equivalents of the subject matter recited in the claims appended hereto as permitted by applicable law. Moreover, any combination of the elements in all possible variations thereof is encompassed by the invention unless otherwise indicated herein or otherwise clearly contradicted by context.

DESCRIPTION OF REFERENCE NUMERALS AND SYMBOLS 10 head-and-neck modeling unit
10a dynamic three-dimensional model of head-and-neck
10b model of tongue
10c model of laryngeal
11 tongue
11a to 11e sector portion of tongue
11f genioglossus
11g tongue surface portion
12 larynx
12a epiglottis
12c larynx portion
13 trachea
14 pharynx
14a pharyngeal wall
14b pharyngeal mucosa
15 palate
15a hard palate
15b soft palate
16 jaw
16a mental region
17 oral cavity
18 gullet
18a esophageal entrance
20 pseudo-orally-ingested product
30 organ movement setting unit
40 orally-ingested-product physical-property setting unit
45 orally-ingested-product input setting unit
50 movement analysis unit
60 evaluation/diagnosis unit 70 physical property determiner
75 organ movement determiner
81 input unit
82 display unit
82A pseudo-screen display unit
83 storage unit
83A evaluation/diagnosis condition storage unit
83B evaluation/diagnosis-result recording unit
83C orally-ingested-product prototype result recording unit
83D determination production condition recording unit
83E determination organ movement condition recording unit
84 production condition determiner
85 teaching unit
90 controller
100A, 100B swallowing simulation apparatus
200A orally-ingested-product development assistance apparatus
300A dietary education assistance apparatus
400A swallowing simulation apparatus
PC personal computer

The invention claimed is:

1. A swallowing simulation apparatus, comprising:
an input unit;
a display unit;
a storage unit; and
a computer storing, in a non-transitory computer readable medium, a swallowing simulator software including instructions which, when executed by the computer, causes the computer to control a head-and-neck modeling unit, an organ movement setting unit, an orally-ingested-product physical-property setting unit, and a movement analysis unit, and causes the computer to control:
the head-and-neck modeling unit to form a dynamic three-dimensional model of a head-and-neck that includes head-and-neck organs;
the organ movement setting unit to set a movement of each of the head-and-neck organs in the dynamic three-dimensional model of the head-and-neck;
the orally-ingested-product physical-property setting unit to set an orally-ingested product as an analysis target and a physical property of the orally-ingested product;
the input unit to input a pseudo-orally-ingested product formed by modeling the orally-ingested product to an oral cavity;
the movement analysis unit to analyze the movement of each of the head-and-neck organs in the dynamic three-dimensional model of the head-and-neck and a behavior of the pseudo-orally-ingested product during swallowed, in a three-dimensional space using a particle method; and
the display unit to display an analysis result of the movement of each of the head-and-neck organs and the behavior of the pseudo-orally-ingested product during swallowed that are analyzed by the movement analysis unit, on a movement screen wherein:
the storage unit stores, in a non-transitory computer readable medium, the dynamic three-dimensional model of the head-and-neck and the analysis result,
the computer controls the head-and-neck modeling unit to set the head-and-neck organ as a polygon or as a polygon and particles, and
the computer controls the movement analysis unit to treat the pseudo-orally-ingested product as particles,
the computer controls the head-and-neck modeling unit to set a model of a tongue as one of the head-and-neck organs to have a structure divided into n pieces of sector portions in a near-far direction, wherein n is an integer from 3 to 7, while a mental region of a mandible as an origin of a genioglossus is set to a pivot of sector, and
the computer controls the organ movement setting unit to set movements of organs such that each of the sector portions is configured to vibrate in cooperation with one another while vibrations of different sector portions have predetermined phase differences in a radial direction so as to perform a traveling wave movement by movements of organs to transport the pseudo-orally-ingested product toward a far-side direction.

2. The swallowing simulation apparatus according to claim 1, wherein
the head-and-neck modeling unit is configured to form the model of the tongue having a structure where dome shape portions of each of the sector portions overlaps with a dome shape portion of another such that a gap is not formed between the sector portions when each of the sector portions vibrates, the dome shape portion being for forming a surface of the tongue, further the head-and-neck modeling unit is configured to form the model of the tongue having the structure where a tongue surface portion that has both right and left sides extending in the radial direction and has a depression in a central portion between the right and left sides is overlapped with each of the sector portions, and each of the sector portions vibrates in a radial direction in the depression of the tongue surface portion in a static condition; and
the organ movement setting unit is configured to set movements of organs such that each of the sector portions rotates by a predetermined angle toward a far side in a circumferential direction during swallowing and then the pseudo-orally-ingested product is pushed toward a far side by the sector portion at a farthest side of the tongue at an end of swallowing.

3. The swallowing simulation apparatus according to claim 1, wherein
the head-and-neck modeling unit is configured to set the model of the head-and-neck having a structure where the head-and-neck includes a tongue, a palate, a pharynx, a larynx portion, a trachea and a gullet, the larynx portion is divided into an epiglottis and a larynx, an esophageal entrance of the gullet is configured to be closed before swallowing is started, and the esophageal entrance is configured to extend and the pharynx is configured to contract during swallowing; and
the organ movement setting unit is configured to set movements of organs such that the larynx is configured to be moved in a direction to the mental region of the mandible to open the esophageal entrance, the pharynx is configured to contract, and then the epiglottis is configured to be rotated by a predetermined angle toward the far side during swallowing so as to close an entrance of the larynx.

4. The swallowing simulation apparatus according to claim 1, wherein
the orally-ingested-product physical-property setting unit is configured to set a plurality of pseudo-orally-ingested products of liquid, semisolid, or solid as the analysis target, the pseudo-orally-ingested products having different physical properties; and the movement analysis unit is configured to determine free surfaces of the plurality of pseudo-orally-ingested products and boundaries between the plurality of pseudo-orally-ingested products so as to analyze an interlocking behavior of the plurality of pseudo-orally-ingested products.

5. The swallowing simulation apparatus according to claim 1, further comprising
an evaluation/diagnosis unit configured to evaluate or diagnose easiness of eating and/or easiness of drinking of the orally-ingested product based on the behavior of the pseudo-orally-ingested product during swallowed on the movement screen, wherein
the movement screen is a virtual movement screen formed in a virtual space by the swallowing simulation apparatus to simulatively display the analysis result of the movement of each of the head-and-neck organs and the behavior of the pseudo-orally-ingested product during swallowed that are analyzed by the movement analysis unit, and
the evaluation/diagnosis unit is configured to make evaluation or diagnosis based on whether or not a behavior of the pseudo-orally-ingested product in the virtual movement screen satisfies a predetermined condition.

6. The swallowing simulation apparatus according to claim 1, further comprising:
an evaluation/diagnosis-result recording unit configured to record an evaluation result or a diagnosis result related to easiness of eating and/or easiness of drinking of the orally-ingested product based on the analysis result of the behavior of the pseudo-orally-ingested product during swallowed; and
a physical property determiner configured to determine a physical property of the orally-ingested product regarded as appropriate based on the evaluation or diagnosis result recorded in the evaluation/diagnosis-result recording unit.

7. An orally-ingested-product development assistance apparatus, comprising:
the swallowing simulation apparatus according to claim 6;
an orally-ingested-product prototype result recording unit configured to record a result of an experimental production performed under an appropriately-set production condition to have the physical property determined as appropriate by the physical property determiner; and
a production condition determiner configured to determine a production condition that sets a physical property of the orally-ingested product to the physical property determined as appropriate by the physical property determiner based on a prototype result recorded in the orally-ingested-product prototype result recording unit.

8. The orally-ingested-product development assistance apparatus according to claim 7, further comprising
an evaluation/diagnosis unit configured to evaluate or diagnose easiness of eating and/or easiness of drinking of the orally-ingested product based on the behavior of the pseudo-orally-ingested product during swallowed, on the movement screen, wherein
the movement screen is a virtual movement screen formed in a virtual space by the swallowing simulation apparatus to simulatively display the analysis result of the movement of each of the head-and-neck organs and the behavior of the pseudo-orally-ingested product during swallowed that are analyzed by the movement analysis unit, and
the evaluation/diagnosis unit is configured to make evaluation or diagnosis based on whether or not a behavior of the pseudo-orally-ingested product in the virtual movement screen satisfies a predetermined condition.

9. The dynamic three-dimensional model formed by the head-and-neck modeling unit according to claim 1 and comprising
a model of a tongue as one of the head-and-neck organs, the model of the tongue having a structure divided into n pieces of sector portions in a near-far direction, wherein n is an integer equal to or more than 2, while a mental region of a mandible as an origin of a genioglossus is set to a pivot of sector;
wherein each of the sector portions is configured to vibrate in cooperation with one another while having a predetermined phase difference in a radial direction so as to perform a traveling wave movement by movements of organs to transport the pseudo-orally-ingested product toward a far-side direction.

10. The dynamic three-dimensional model of the head-and-neck according to claim 9,
wherein the model of the tongue has a structure where a dome shape portion of each of the sector portions overlaps with a dome shape portion of another such that a gap is not formed between the sector portions when each of the sector portions vibrates, the dome shape portion being for forming a surface of the tongue, the model of the tongue further has a structure where a tongue surface portion that has both right and left sides extending in the radial direction and has a depression in a central portion between the right and left sides is overlapped with each of the sector portions, and each of the sector portions vibrates in a circumferential direction in the depression of the tongue surface portion in a static state;
wherein the model of the tongue is configured to be set such that the sector portions rotate by a predetermined angle toward a far side in a circumferential direction during swallowing and then the pseudo-orally-ingested product is pushed toward the far side by the sector portion at a farthest side of the tongue;
wherein the dynamic three-dimensional model of the head-and-neck has a structure where the head-and-neck includes a tongue, a palate, a pharynx, a larynx portion, a trachea and a gullet, the larynx portion is divided into an epiglottis and a larynx, an esophageal entrance of the gullet is configured to be closed before swallowing is started, and the esophageal entrance is configured to extend and the pharynx is configured to contract during swallowing; and
wherein the dynamic three-dimensional model of the head-and-neck is configured to be set such that the larynx is configured to be moved in a direction to the mental region of the mandible to open the esophageal entrance, the pharynx is configured to contract, and then the epiglottis is configured to be rotated by a predetermined angle toward the far side so as to close an esophageal entrance during swallowing.

11. A swallowing simulation method using the swallowing simulation apparatus according to claim 1, comprising:
a head-and-neck modeling step of forming a dynamic three-dimensional model of head-and-neck that includes head-and-neck organs, the head-and-neck modeling step performed by the head-and-neck modeling unit;
an organ-movement setting step of setting a movement of each of the head-and-neck organs in the dynamic three-dimensional model of the head-and-neck, the organ-movement setting step performed by the organ-movement setting unit;

an orally-ingested-product physical-property setting step of setting an orally-ingested product as an analysis target and a physical property of the orally-ingested product, orally-ingested-product physical-property setting step performed by the orally-ingested-product physical-property setting unit;

an input step of inputting, via the input unit, a pseudo-orally-ingested product formed by modeling the orally-ingested product to an oral cavity;

a movement analyzing step of analyzing the movement of each of the head-and-neck organs in the dynamic three-dimensional model of the head-and-neck and a behavior of the pseudo-orally-ingested product during swallowed using a particle method, the movement analyzing step performed by the movement analyzing unit; and a display step of displaying, on the display unit, the analysis result of the movement of each of the head-and-neck organs and the behavior of the pseudo-orally-ingested product during swallowed that are analyzed in a three-dimensional space in the movement analyzing step, on a movement screen.

12. The swallowing simulation method according to claim 11, wherein the swallowing simulation apparatus further comprises an evaluation/diagnosis unit, a physical property determination unit, an evaluation/diagnosis-result recording unit, and a physical property determiner, and the method further comprises:

an evaluation/diagnosis step of evaluating or diagnosing easiness of eating and/or easiness of drinking of the orally-ingested product based on the analysis result of the behavior of the pseudo-orally-ingested product during swallowed, the evaluation/diagnosis step performed by the evaluation/diagnosis unit;

a physical property determination step of determining a physical property of the orally-ingested product regarded as appropriate based on an evaluation result evaluated or diagnosis result diagnosed in the evaluation/diagnosis step, the physical property determination step performed by the physical property determination unit;

recording, in the evaluation/diagnosis-result recording unit, an evaluation result or a diagnosis result related to easiness of eating and/or easiness of drinking of the orally-ingested product based on the analysis result of the behavior of the pseudo-orally-ingested product during swallowed; and determining, by the physical property determiner, a physical property of the orally-ingested product regarded as appropriate based on the evaluation or diagnosis result recorded in the evaluation/diagnosis-result recording unit.

13. An orally-ingested-product development method, comprising the swallowing simulation method according to claim 12, wherein the orally-ingested-product physical-property setting step includes a step of changing the physical property of the orally-ingested product to set, and a step of repeatedly performing a subsequent process up to the physical property determination step, or a step of changing the physical property of the orally-ingested product to set, a step of repeatedly performing a subsequent process up to the evaluation/diagnosis step, and then collectively performing the physical property determination step, further comprising:

an orally-ingested-product prototype production step of performing an experimental production under an appropriately-set production condition to have the physical property determined as appropriate in the physical property determination step; and a production condition determination step of determining a production condition that gives a physical property of the orally-ingested product to the physical property determined as appropriate in the physical property determination step based on the result in the orally-ingested-product prototype production step.

14. The orally-ingested-product development method according to claim 13, wherein the movement screen is a virtual movement screen formed at a virtual space by a swallowing simulation apparatus to simulatively display an analysis result of a movement of each of the head-and-neck organs and a behavior of the pseudo-orally-ingested product during swallowed, the analysis result being analyzed in the movement analysis unit, the display step is a virtual display step to simulatively display the analysis result on the virtual movement screen, and the evaluation/diagnosis step is configured to evaluate whether the behavior of the pseudo-orally-ingested product on the virtual movement screen simulatively displayed in the virtual display step meets a predetermined condition or not.

15. An orally-ingested-product production method, comprising a step of producing the orally-ingested product using a production condition determined in the production condition determination step of the orally-ingested-product development method according to claim 13.

16. A diagnosis method, wherein the diagnosis step determines whether muscles of a patient or a person subject to checkup are functionally deteriorated in the swallowing or not from the results of the swallowing simulation in the swallowing simulation method according to claim 12.

17. A dietary education method, comprising:

the swallowing simulation method according to claim 11;

an evaluation step of evaluating easiness of eating and/or easiness of drinking of the orally-ingested product based on the analysis result of the behavior of the pseudo-orally-ingested product during swallowed; and a teaching step of explaining the behavior of the pseudo-orally-ingested product during swallowed displayed on the movement screen in the display step associating with the evaluation result of the orally-ingested product evaluated in the evaluation step.

18. A non-transitory computer readable medium containing program instructions for making a computer to execute the swallowing simulation method according to claim 11.

19. A dietary education assistance apparatus, comprising:

the swallowing simulation apparatus according to claim 1;

an evaluation/diagnosis-result recording unit configured to record an evaluation result or a diagnosis result of easiness of eating and easiness of drinking of the orally-ingested product based on the analysis result of the behavior of the pseudo-orally-ingested product during swallowed; and a teaching unit configured to explain the behavior of the pseudo-orally-ingested product during swallowed displayed on the movement screen by the display unit associating with the evaluation result or the diagnosis result of the orally-ingested product recorded in the evaluation/diagnosis-result recording unit.

20. The swallowing simulation apparatus according to claim 1, further comprising
an organ movement determiner configured to determine an organ movement parameter fitting to a behavior or a symptom of an organ of a diagnosed person based on the analysis result analyzed in the movement analysis unit in the organ movement parameters set in the organ movement setting unit.

21. A diagnosis assistance apparatus; comprising
the swallowing simulation apparatus according to claim 20.

* * * * *